(12) United States Patent
Suddaby

(10) Patent No.: US 11,701,239 B2
(45) Date of Patent: Jul. 18, 2023

(54) STAND-ALONE EXPANDABLE INTERBODY SPINAL FUSION DEVICE WITH INTEGRATED FIXATION MECHANISM

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 225 days.

(21) Appl. No.: 17/030,487

(22) Filed: Sep. 24, 2020

(65) Prior Publication Data

US 2021/0015626 A1    Jan. 21, 2021

Related U.S. Application Data

(63) Continuation-in-part of application No. 15/416,270, filed on Jan. 26, 2017, now Pat. No. 11,207,192.

(51) Int. Cl.
*A61F 2/44* (2006.01)
*A61F 2/30* (2006.01)

(52) U.S. Cl.
CPC .......... *A61F 2/447* (2013.01); *A61F 2/4405* (2013.01); *A61F 2002/3085* (2013.01); *A61F 2002/30525* (2013.01); *A61F 2002/30579* (2013.01)

(58) Field of Classification Search
CPC ...... A61F 2/4455; A61F 2/446; A61F 2/4465; A61F 2/447; A61F 2/4405
See application file for complete search history.

(56) References Cited

U.S. PATENT DOCUMENTS

| | | | |
|---|---|---|---|
| 5,505,732 A | 4/1996 | Michelson |
| 5,653,762 A | 8/1997 | Pisharodi |
| 5,665,122 A | 9/1997 | Kambin |
| 5,683,463 A | 11/1997 | Godefroy et al. |
| 5,827,328 A | 10/1998 | Buttermann |
| 6,176,881 B1 | 1/2001 | Schär et al. |
| 6,190,414 B1 | 2/2001 | Young et al. |
| 6,395,034 B1 | 5/2002 | Suddaby |
| 6,524,341 B2 | 2/2003 | Läng et al. |
| 6,837,850 B2 | 1/2005 | Suddaby |
| 6,958,077 B2 | 10/2005 | Suddaby |
| 6,969,405 B2 | 11/2005 | Suddaby |
| 6,991,653 B2 | 1/2006 | White et al. |
| 7,309,358 B2 | 12/2007 | Berry et al. |

(Continued)

OTHER PUBLICATIONS

Sahara Al Expandable Stabilization System; Advertisement flyer; Available from K2M, Inc. Leesburg, Virginia; Published as early as Oct. 20, 2015.

(Continued)

*Primary Examiner* — Si Ming Ku
(74) *Attorney, Agent, or Firm* — Harter Secrest & Emery LLP; Michael Nicholas Vranjes

(57) ABSTRACT

A stand-alone expandable interbody spinal fusion device, including a superior component, an inferior component, and an expansion mechanism operatively arranged to displace the superior component relative to the inferior component, the expansion mechanism including a threaded rod including a first end engaged with the superior component and a second end engaged with the inferior component, wherein when the threaded rod is rotated in a first circumferential direction, the superior component is displaced in a first direction relative to the inferior component.

20 Claims, 42 Drawing Sheets

(56) References Cited

U.S. PATENT DOCUMENTS

| | | |
|---|---|---|
| 7,597,714 B2 | 10/2009 | Suddaby |
| 7,615,078 B2 | 11/2009 | White et al. |
| 7,628,800 B2 | 12/2009 | Sherman et al. |
| 7,648,529 B2 | 1/2010 | An et al. |
| 7,731,752 B2 | 6/2010 | Edie et al. |
| 8,007,535 B2 | 8/2011 | Hudgins et al. |
| 8,057,549 B2 | 11/2011 | Butterman et al. |
| 8,187,328 B2 | 5/2012 | Melkent |
| 8,246,630 B2 | 8/2012 | Manzi et al. |
| 8,273,126 B2 | 9/2012 | Lindner |
| 8,303,663 B2 | 11/2012 | Jimenez et al. |
| 8,435,296 B2 | 5/2013 | Kadaba et al. |
| 8,480,738 B2 | 7/2013 | Edie et al. |
| 8,512,406 B2 | 8/2013 | White et al. |
| 8,568,481 B2 | 10/2013 | Olmos et al. |
| 8,696,751 B2 | 4/2014 | Ashley et al. |
| 8,900,312 B2 | 12/2014 | McLean et al. |
| 8,932,302 B2 | 1/2015 | Jimenez et al. |
| 8,956,413 B2 | 2/2015 | Ashley et al. |
| 8,992,620 B2 | 3/2015 | Ashley et al. |
| 9,011,499 B1 | 4/2015 | Kiester |
| 9,066,760 B2 | 6/2015 | Taber et al. |
| 9,078,767 B1 | 7/2015 | McLean |
| 9,084,686 B1 | 7/2015 | McLean et al. |
| 9,889,019 B2 | 2/2018 | Rogers et al. |
| 2003/0191531 A1 | 10/2003 | Berry et al. |
| 2005/0049590 A1 | 3/2005 | Alleyne et al. |
| 2006/0149385 A1 | 7/2006 | Mckay |
| 2006/0241621 A1 | 10/2006 | Moskowitz et al. |
| 2007/0049943 A1 | 3/2007 | Moskowitz et al. |
| 2007/0250172 A1 | 10/2007 | Moskowitz et al. |
| 2008/0058930 A1 | 3/2008 | Edie et al. |
| 2008/0140207 A1 | 6/2008 | Olmos et al. |
| 2008/0215153 A1 | 9/2008 | Butterman et al. |
| 2010/0004752 A1 | 1/2010 | White et al. |
| 2010/0057204 A1 | 3/2010 | Kadaba et al. |
| 2010/0076559 A1 | 3/2010 | Bagga et al. |
| 2010/0168862 A1* | 7/2010 | Edie .................. A61F 2/44 623/17.16 |
| 2010/0198352 A1 | 8/2010 | Edie et al. |
| 2011/0054616 A1 | 3/2011 | Kamran et al. |
| 2011/0130835 A1 | 6/2011 | Ashley et al. |
| 2012/0059479 A1 | 3/2012 | Buttermann et al. |
| 2012/0116518 A1 | 5/2012 | Grotz et al. |
| 2013/0131808 A1 | 5/2013 | Suh et al. |
| 2013/0231747 A1 | 9/2013 | Olmos et al. |
| 2013/0253650 A1 | 9/2013 | Ashley et al. |
| 2013/0261748 A1 | 10/2013 | Ashley et al. |
| 2014/0012383 A1 | 1/2014 | Triplett et al. |
| 2014/0207236 A1 | 7/2014 | Prevost et al. |
| 2014/0277471 A1 | 9/2014 | Gray et al. |
| 2014/0277476 A1 | 9/2014 | McLean et al. |
| 2014/0277480 A1 | 9/2014 | Prevost et al. |
| 2015/0012098 A1 | 1/2015 | Eastlack et al. |
| 2015/0081022 A1 | 3/2015 | McLean et al. |
| 2015/0148907 A1 | 5/2015 | Kleiner et al. |
| 2016/0089247 A1* | 3/2016 | Nichols ............... A61F 2/30767 623/17.16 |
| 2016/0100951 A1 | 4/2016 | Suddaby et al. |
| 2017/0165082 A1 | 6/2017 | Faulhaber |
| 2018/0116818 A1 | 5/2018 | Rogers et al. |
| 2018/0303626 A1 | 10/2018 | Rogers et al. |

OTHER PUBLICATIONS

Loubert S. Suddaby; Unpublished U.S. Appl. No. 15/273,032; Expandable Intervertebral Fusion Implant; filed Sep. 22, 2016.

\* cited by examiner

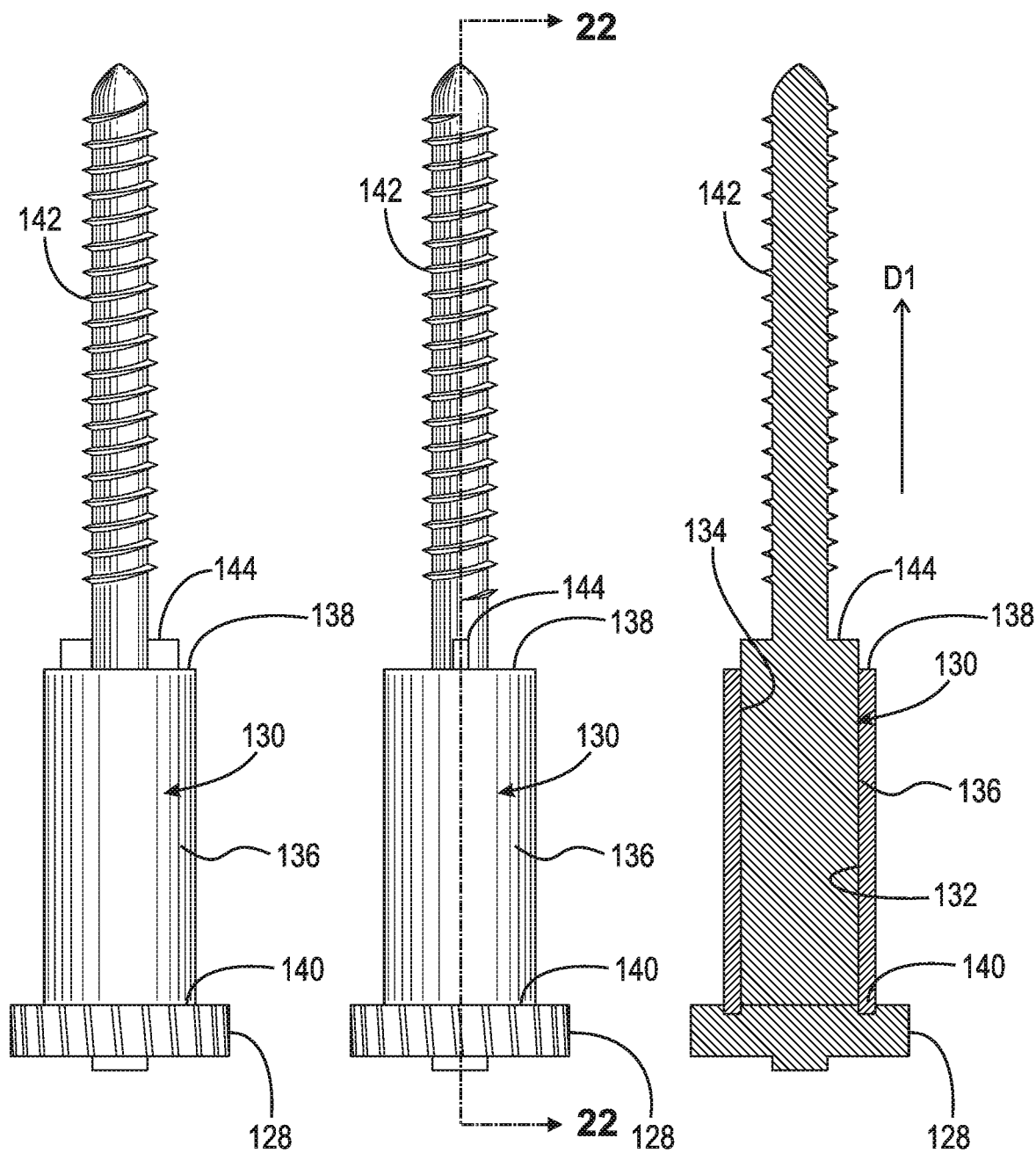

STAND-ALONE EXPANDABLE INTERBODY SPINAL FUSION DEVICE WITH INTEGRATED FIXATION MECHANISM

CROSS-REFERENCE TO RELATED APPLICATIONS

This application is filed under 35 U.S.C. § 120 as a continuation-in-part of U.S. patent application Ser. No. 15/416,270, filed on Jan. 26, 2017, which reference is hereby incorporated by reference in its entirety.

FIELD

The invention relates to spinal surgery, more particularly to intervertebral prosthesis, and, even more specifically, to a stand-alone expandable interbody spinal fusion device with integrated fixation mechanism.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae (C1-C7) form the neck, support the head and neck, and allow nodding and shaking of the head. The thoracic vertebrae (T1-T12) join with the ribs to form the rib cage. The five lumbar vertebrae (L1-L5) carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal, or neuro canal. The spinal cord and spinal nerves pass through the spinal canal, which protects them from injury. The spinal cord is the major column of nerve tissue that is connected to the brain and serves as an information superhighway between the brain and the body. The nerves in the spinal cord branch off to form pairs of nerve roots that travel through the small openings between the vertebrae and the intervertebral foramens.

The repetitive forces which act on these intervertebral discs during repetitive day-to-day activities of bending, lifting and twisting cause them to break down or degenerate over time. Overt trauma, or covert trauma occurring in the course of repetitive activities disproportionately affect the more highly mobile areas of the spine. Disruption of a disc's internal architecture leads to bulging, herniation or protrusion of pieces of the disc and eventual disc space collapse. Resulting mechanical and chemical irritation of surrounding neural elements cause pain, attended by varying degrees of disability. In addition, loss of disc space height relaxes tension on the longitudinal ligaments, thereby contributing to varying degrees of spinal instability such as spinal curvature.

Neural irritation and instability resulting from severe disc damage has been treated by removing the damaged disc and fusing adjacent vertebral elements. Removal of the disc relieves the mechanical and chemical irritation of neural elements, while osseous union solves the problem of instability. For example, in one surgical procedure, known as a discectomy (or diskectomy) with interbody fusion, the surgeon removes the nucleus of the disk and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, but with vertebra L3 in place atop disc $D_{L3-L4}$.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union.

Intervertebral prosthesis in various forms have therefore been used to provide immediate stability and to protect and preserve an environment that fosters growth of grafted bone such that a structurally significant bony fusion can occur.

Limitations of most present day intervertebral implants is their tendency to migrate after implantation, necessitating the use of supplemental fixation such as an anterior or lateral plating system or posterior pedicle screw or lateral mass fixation to prevent unexpected device dislodgement.

Other interbody devices have been designed with orifices through which screws, blades, or other metallic fixation devices are placed after device insertion to mitigate unwanted slippage of the device after implementation. In addition, these devices may require additional placement of hardware anteriorly or laterally at the time of surgery, or, require a second surgery so that hardware such as pedicle screws can be added posteriorly so that the device is held securely.

Thus, there is a long-felt need for a stand-alone expandable interbody spinal fusion device with integrated fixation mechanism that would obviate the need for supplemental fixation such that the device could be simply implanted between vertebral bodies and fixated using the insertion device such that it is easily inserted and could function in a stand-alone capacity.

SUMMARY

According to aspects illustrated herein, there is provided a stand-alone expandable interbody spinal fusion device, comprising a superior component, an inferior component, and an expansion mechanism operatively arranged to displace the superior component relative to the inferior component, the expansion mechanism including a threaded rod including a first end engaged with the superior component and a second end engaged with the inferior component, wherein when the threaded rod is rotated in a first circumferential direction, the superior component is displaced in a first direction relative to the inferior component.

In some embodiments, the expansion mechanism further comprises a gear rotatably connected to the inferior component, and the second end is fixedly secured to the gear. In some embodiments, the superior component comprises a threaded hole and the threaded rod is threadably engaged with the threaded hole. In some embodiments, the expansion mechanism further comprises a threaded collar threadably engaged with the threaded rod. In some embodiments, the threaded collar abuts against the superior component. In some embodiments, the expansion mechanism further comprises a worm rotatably connected to the inferior component and engaged with the gear. In some embodiments, the superior component comprises at least one aperture and the inferior component comprises at least one aperture. In some embodiments, when the threaded rod is rotated in a second circumferential direction, opposite the first circumferential direction, the superior component is displaced in a second direction relative to the inferior component.

According to aspects illustrated herein, there is provided a stand-alone expandable interbody spinal fusion device, comprising an inferior component including a first inward facing surface and a first outward facing surface, a superior component including a second inward facing surface and a second outward facing surface, and an expansion mechanism, including a gear rotatably connected to the inferior component, and a threaded rod including a first end engaged with the superior component and a second end fixedly secured to the gear, wherein when the threaded rod is rotated in a first circumferential direction, the superior component is displaced in a first direction relative to the inferior component.

In some embodiments, the superior component comprises a threaded hole and the threaded rod is threadably engaged with the threaded hole. In some embodiments, the expansion mechanism further comprises a threaded collar threadably engaged with the threaded rod. In some embodiments, the threaded collar abuts against the superior component. In some embodiments, the threaded collar is at least partially embedded in the superior component. In some embodiments, the expansion mechanism further comprises a worm rotatably connected to the inferior component and engaged with the gear. In some embodiments, the inferior component comprises at least one aperture extending from the first inner surface to the first outer surface and the superior component comprises at least one aperture extending from the second inner surface to the second outer surface. In some embodiments, when the threaded rod is rotated in a second circumferential direction, opposite the first circumferential direction, the superior component is displaced in a second direction relative to the inferior component.

According to aspects illustrated herein, there is provided a stand-alone expandable interbody spinal fusion device, comprising an inferior component including a first inward facing surface and a first outward facing surface, a superior component including a second inward facing surface and a second outward facing surface, and an expansion mechanism, including a gear rotatably connected to the inferior component, and a threaded rod including a first end threadably engaged with the superior component and a second end fixedly secured to the gear, wherein when the threaded rod is rotated the superior component is displaced relative to the inferior component.

In some embodiments, the threaded rod is threadably engaged with the superior component via a threaded collar, the threaded collar operatively arranged to abut against the second inward facing surface. In some embodiments, the expansion mechanism further comprises a worm engaged with the gear. In some embodiments, the superior component comprises a threaded hole extending from the second inward facing surface and the threaded rod is threadably engaged with the threaded hole.

According to aspects illustrated herein, there is provided a stand-alone expandable interbody spinal fusion device with an integrated fixation mechanism including a superior component, an inferior component, an expansion mechanism operatively arranged to displace the superior component in a first direction relative to the inferior component, and a first screw mechanism arranged within the superior component or inferior component.

According to aspects illustrated herein, there is provided a stand-alone expandable interbody spinal fusion device with integrated fixation mechanism including a body having a proximate end and a distal end, the body further includes a superior component, an inferior component, a first gear shaft operatively arranged to engage a first plurality of expansion mechanisms, where the first plurality of expansion mechanisms are operatively arranged to displace the superior component in a first direction relative to the inferior component, a first screw mechanism operatively arranged within the proximate end of the superior component, a second screw mechanism operatively arranged within the proximate end of the inferior component, and a first aperture operatively arranged on the superior or inferior components.

According to aspects illustrated herein, there is provided a stand-alone expandable interbody spinal fusion device with integrated fixation mechanism including a superior component, an inferior component, and a first screw mechanism arranged within the superior component or inferior component, where the superior component is operatively arranged to be displaced in a first direction relative to the inferior component.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 20 is a side view of a first embodiment of a self-piercing screw mechanism in an unexpanded state;

FIG. 21 is a side view of a first embodiment of a self-piercing screw mechanism in an unexpanded state;

FIG. 22 is a cross-sectional view of a first embodiment of a self-piercing screw mechanism is an unexpanded state, taken generally along line 22-22 in FIG. 21;

DETAILED DESCRIPTION

Figure 1:
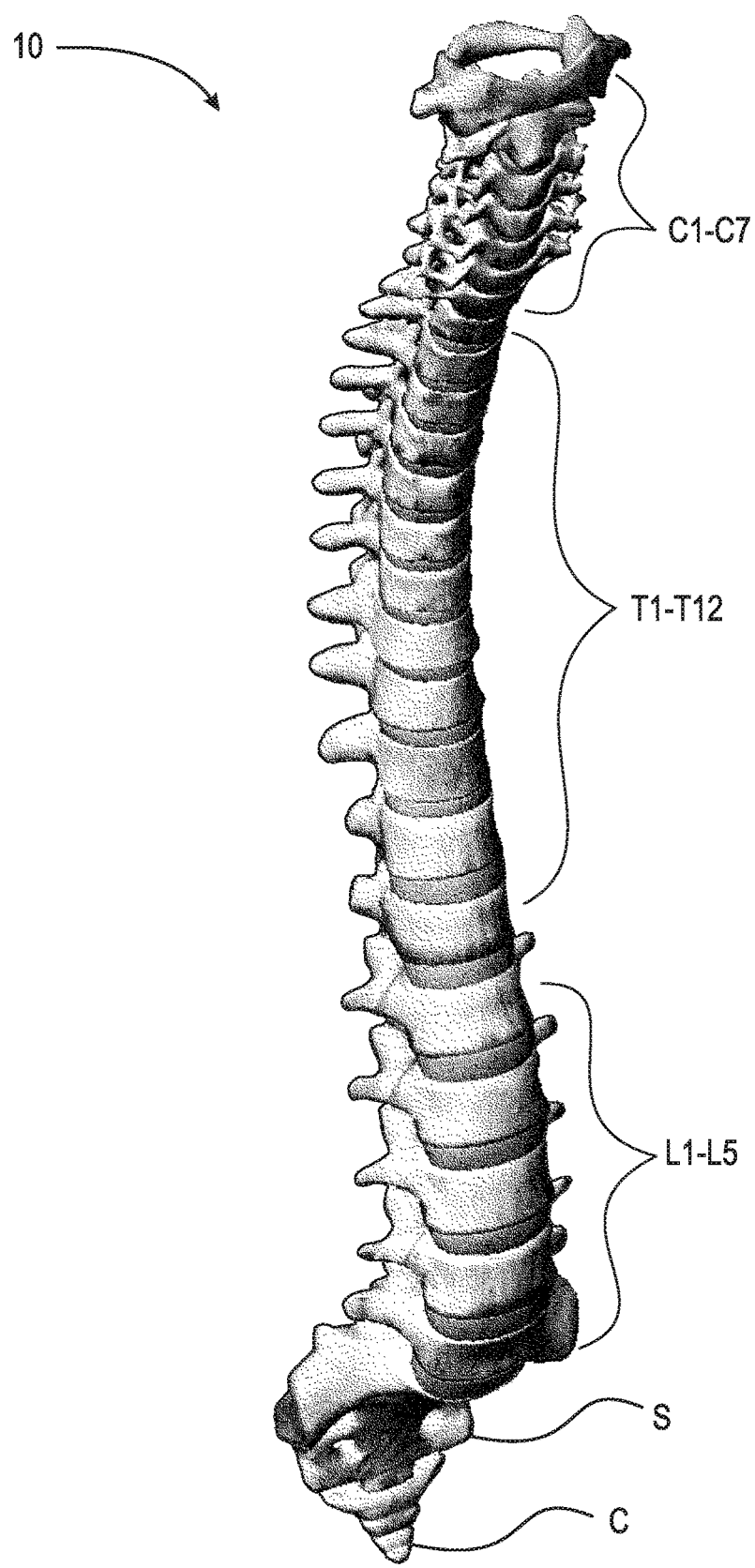
FIG. 1 is an anterior perspective view of spinal column 10.
Figure 2:
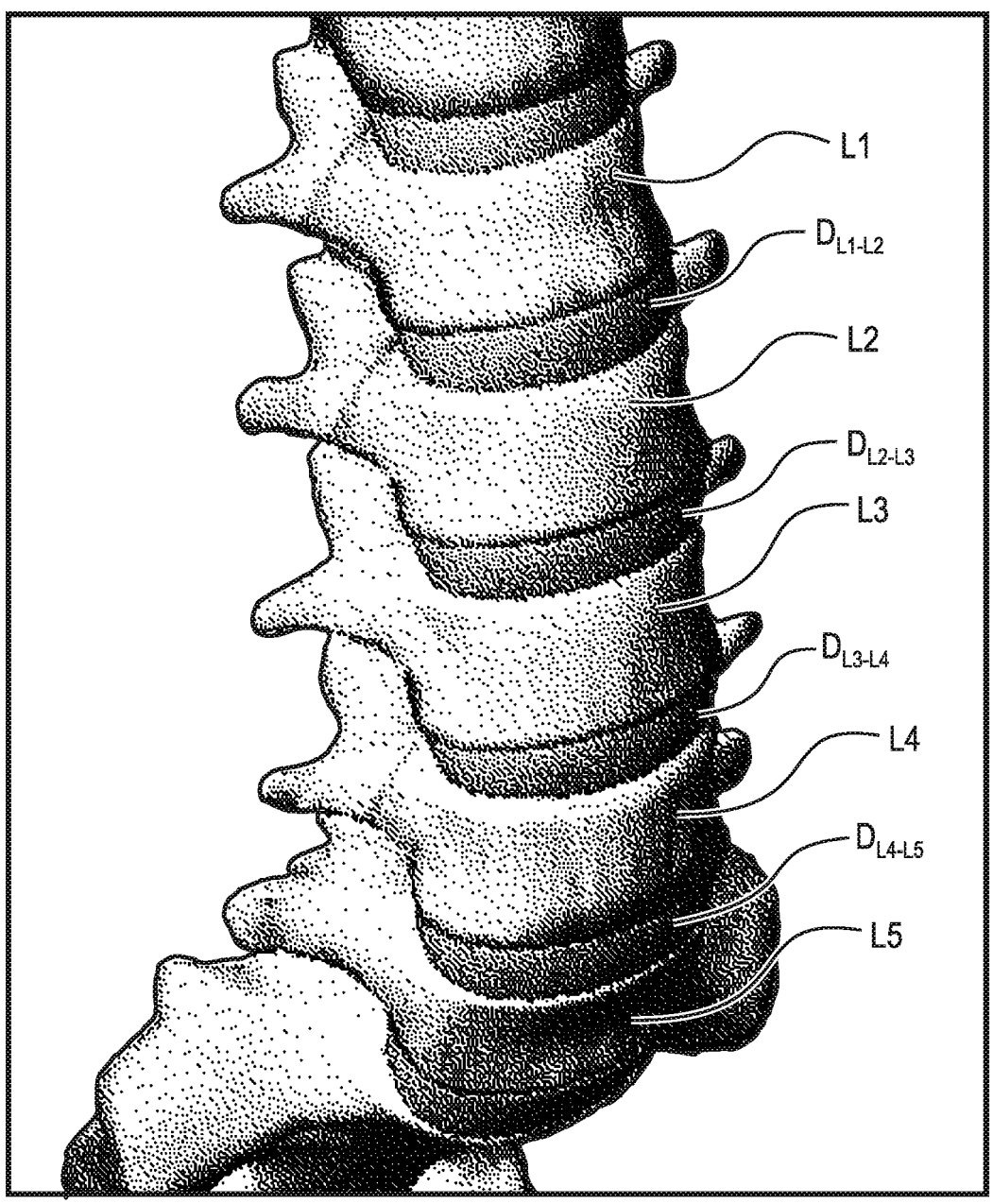
FIG. 2 is an anterior perspective view of the lumbar section of spinal column 10.
Figure 3:
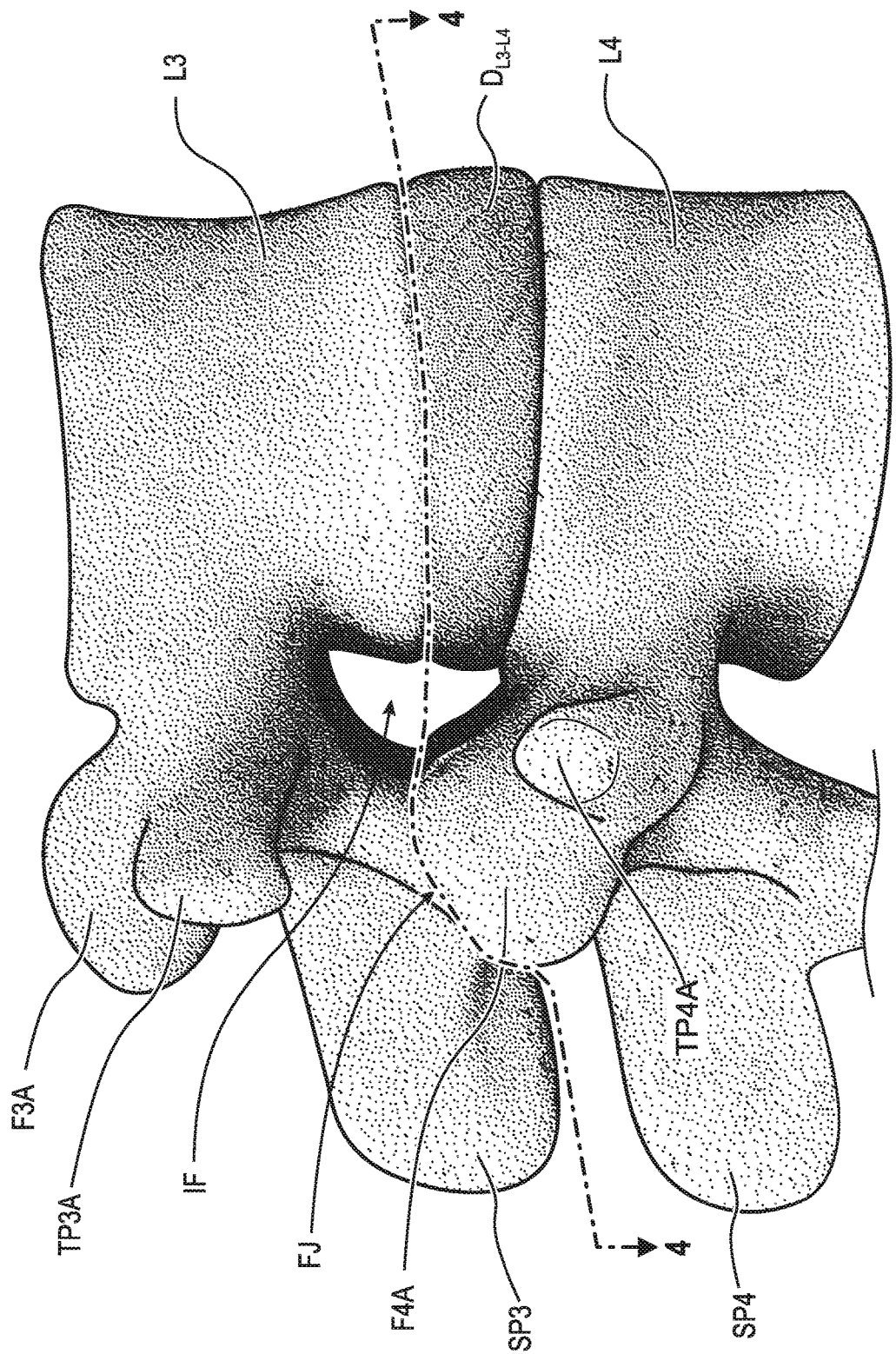
FIG. 3 is a lateral perspective view of L3, L4 vertebrae and disc $D_{L3-L4}$ and related spinal anatomy.
Figure 4:
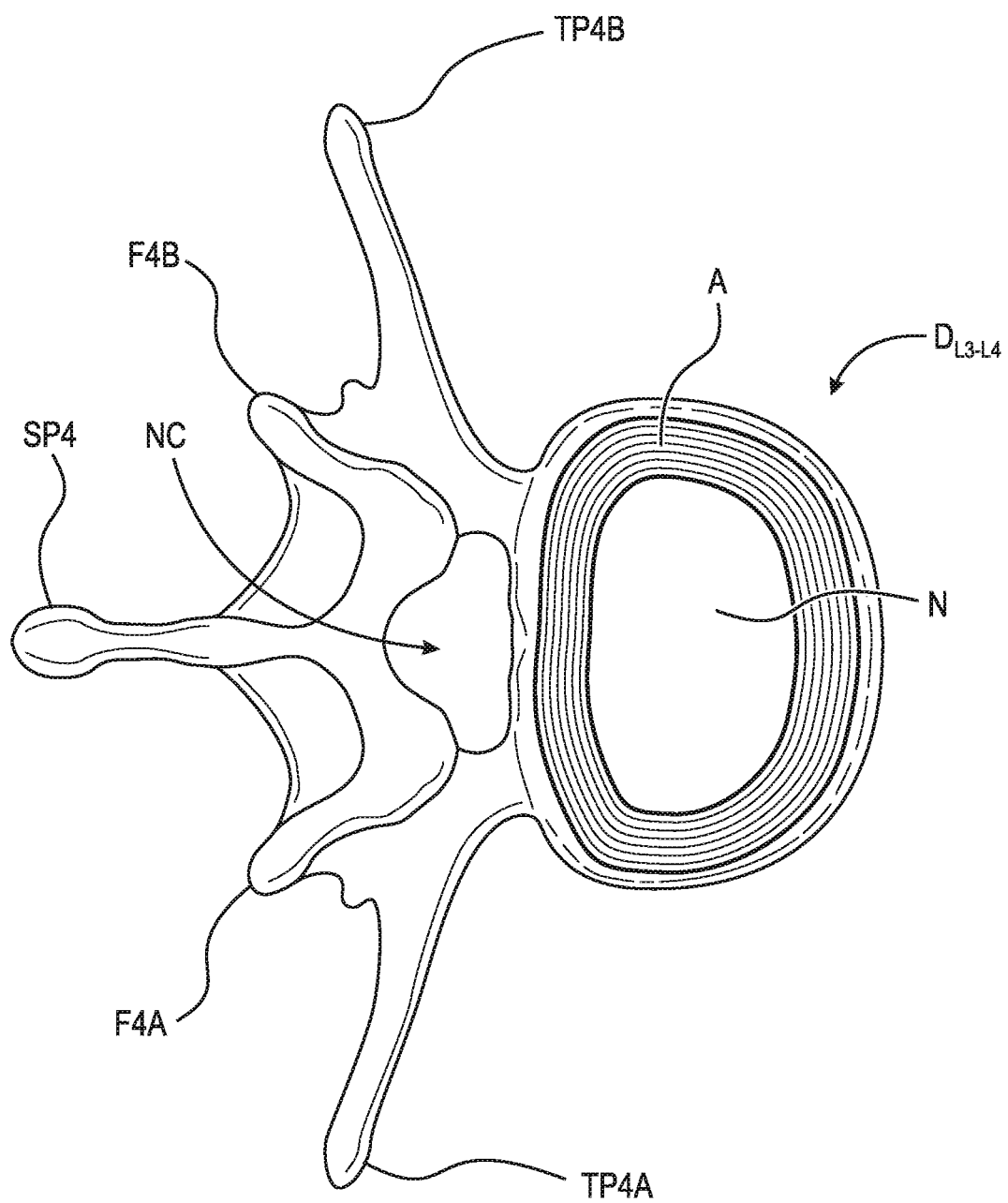
FIG. 4 is a top view of a section of the spinal column, taken generally along line 4-4 in FIG. 3.
Figure 5:
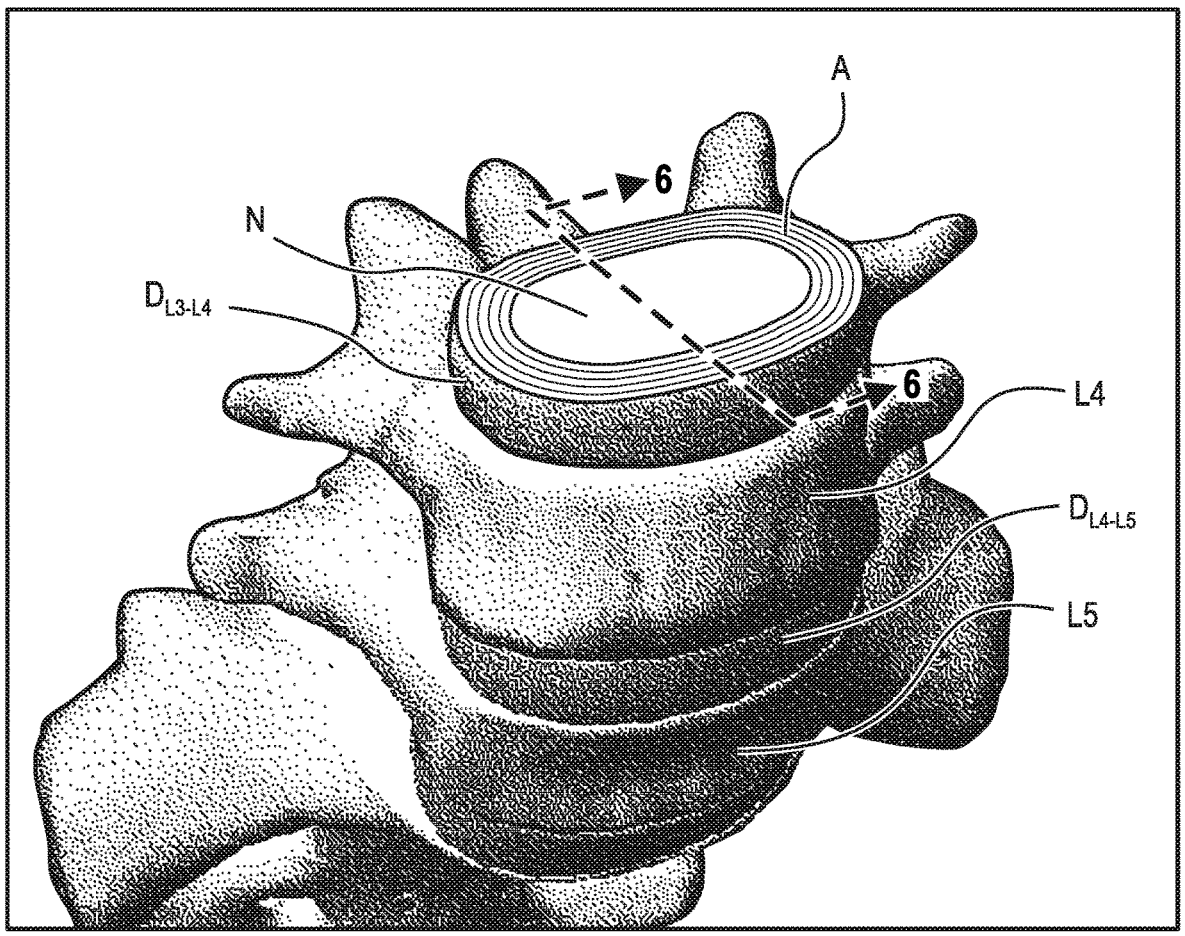
FIG. 5 is an enlarged anterior perspective view of the spinal column shown in FIG. 2, except with vertebra L3 and all other structure above L3 removed.
Figure 6:
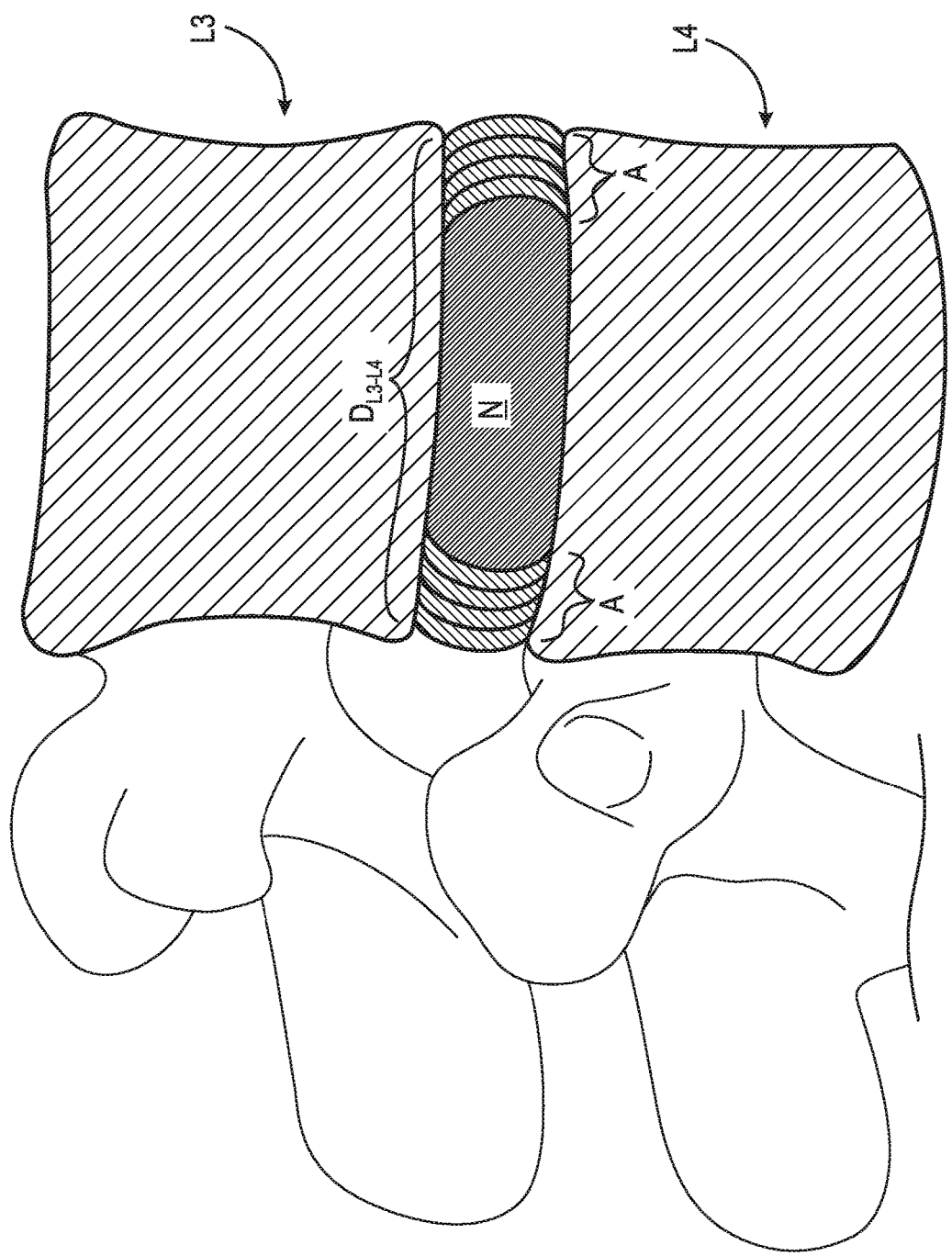
FIG. 6 is a partial cross-sectional view of the L4 vertebra and $D_{L3-L4}$ disc shown in FIG. 5, including L3 in cross-section.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

The term "Superior Component" as used in the present disclosure is intended to mean the component of the body of the implant located in the highest position relative to the other components in the first direction D1.

The term "Inferior Component" as used in the present disclosure is intended to mean the component of the body of the implant located in the lowest position relative to the other components in the first direction D1.

The term "screw body" as used in the present disclosure is intended to mean a sharp-pointed metal pin with a raised helical thread running around it (either left-handed or right-handed threads can be used) and can be used to join objects together by being rotated so that it pierces the surface of the material (e.g., wood, bone, or any other material less dense than the screw body material). The pitch of threading could be varied to allow for changes in bone density and the thread could be various threads known in the art such as V-thread, American, British, Square, Buttress, Knuckle, or any suitable threading that would engage with bone material. It should also be appreciated that, throughout this disclosure, a self-piercing screw is illustrated as a non-limiting example, and in the alternative a self-drilling, or a self-tapping screw could be used.

The term "gear shaft" as used in the present disclosure is intended to mean any gear currently understood in the art that has been elongated such that it is substantially cylindrical in shape.

The term "anchor layer" as used in the present disclosure is intended to mean a thin layer of material fixed within or on the superior and inferior components and creates a fixed point for a screw body to engage with and achieve the required leverage to engage the bone material of the adjacent vertebra. It should be appreciated that the anchor layer could be made out of ceramic, carbon fiber, high density plastic, polymer, or any suitable metal more dense than the metal of the screw body, such as titanium.

Figure 7:
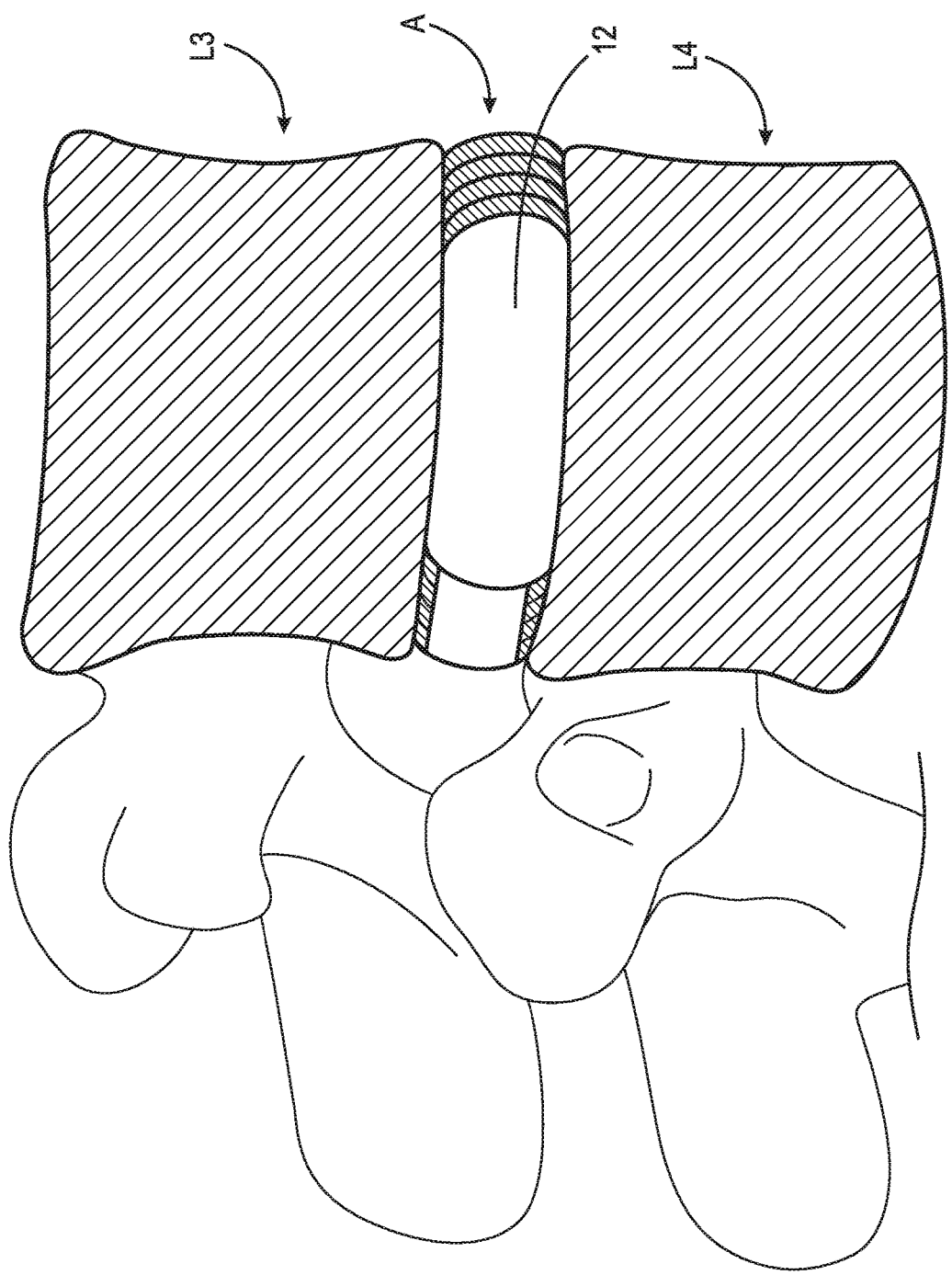
FIG. 7 is a partial cross-sectional view of the L4 vertebra and $D_{L3-L4}$ disc shown in FIG. 5, showing the removal of the disc nucleus post-discectomy.

Adverting now to the Figures, and as described previously, FIGS. 1-6 depict various parts and sections of spinal anatomy. FIG. 7 illustrates a partial cross-sectional view of the L3 and L4 vertebra with disc $D_{L3-L4}$ removed (post discectomy) able to receive stand-alone expandable interbody spinal fusion device 100.

Figure 8:
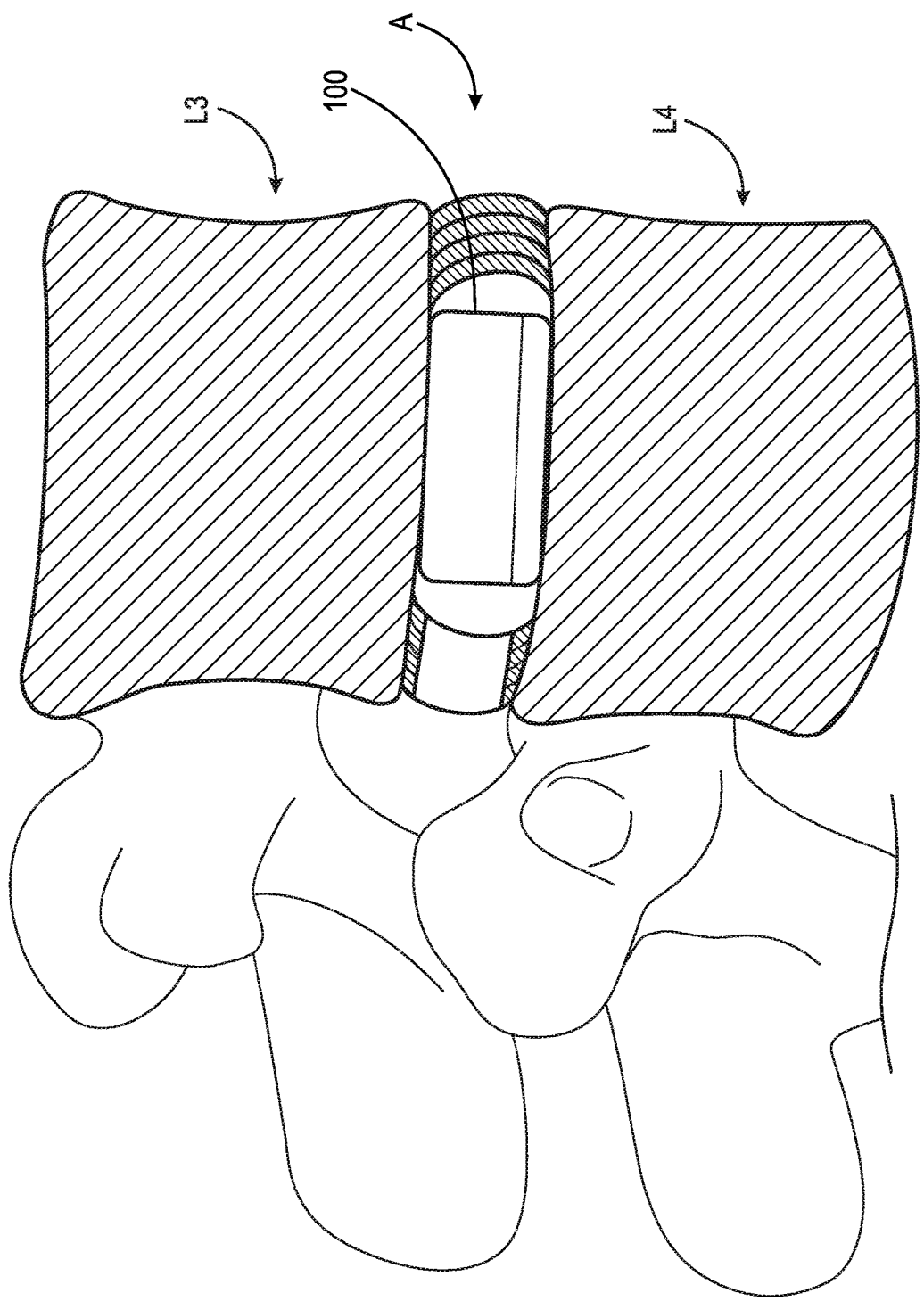
FIG. 8 illustrates the introduction of the stand-alone expandable interbody spinal fusion device into the disc space in an unexpanded state.

FIG. 8 illustrates a partial cross-sectional view of the L3 and L4 vertebra with stand-alone expandable interbody spinal fusion device 100 in place within disc space 12 in an unexpanded state.

Figure 9:
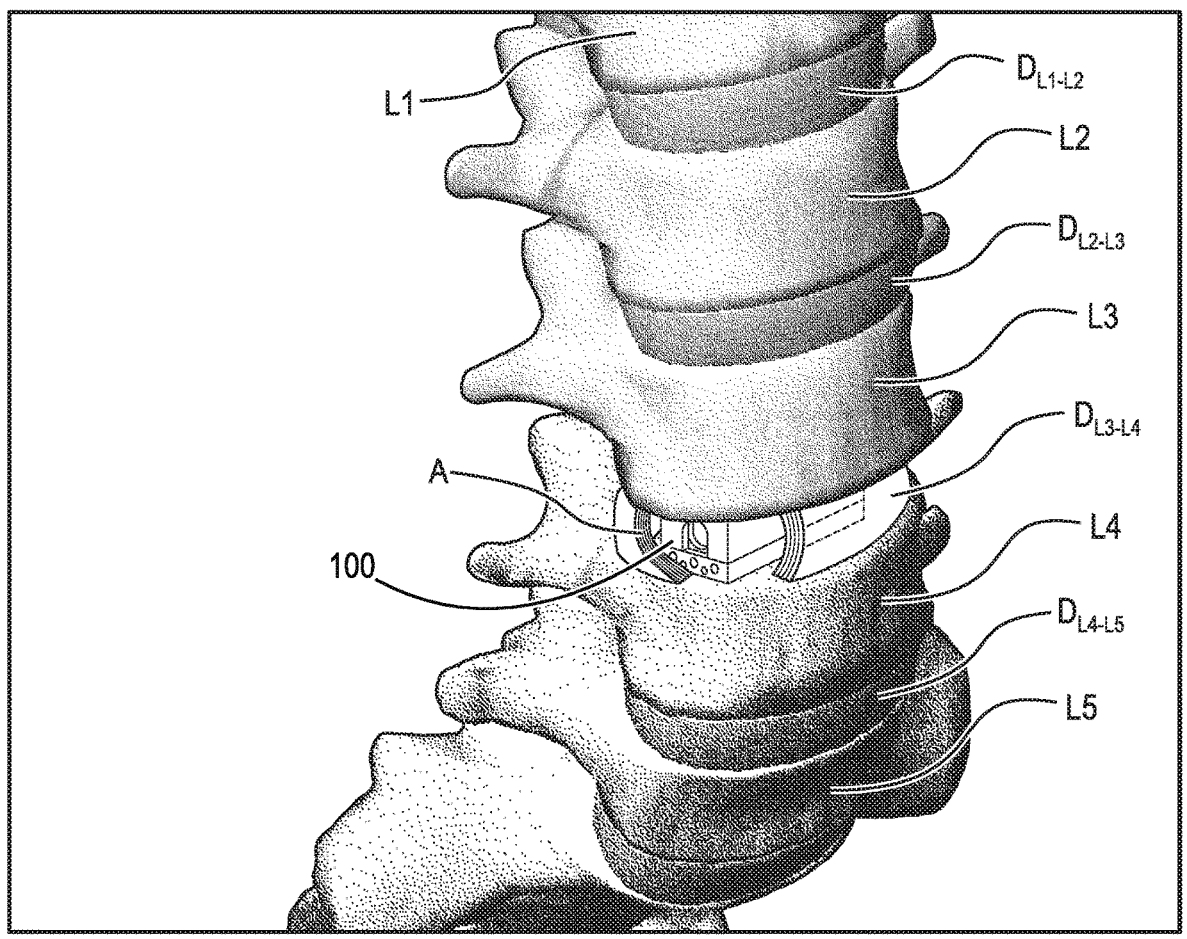
FIG. 9 is an anterior perspective view of spinal column 10 including the stand-alone expandable interbody spinal fusion device in an unexpanded state.

FIG. 9 is an anterior perspective view of spinal column 10 including stand-alone expandable interbody spinal fusion device 100.

Figure 10:
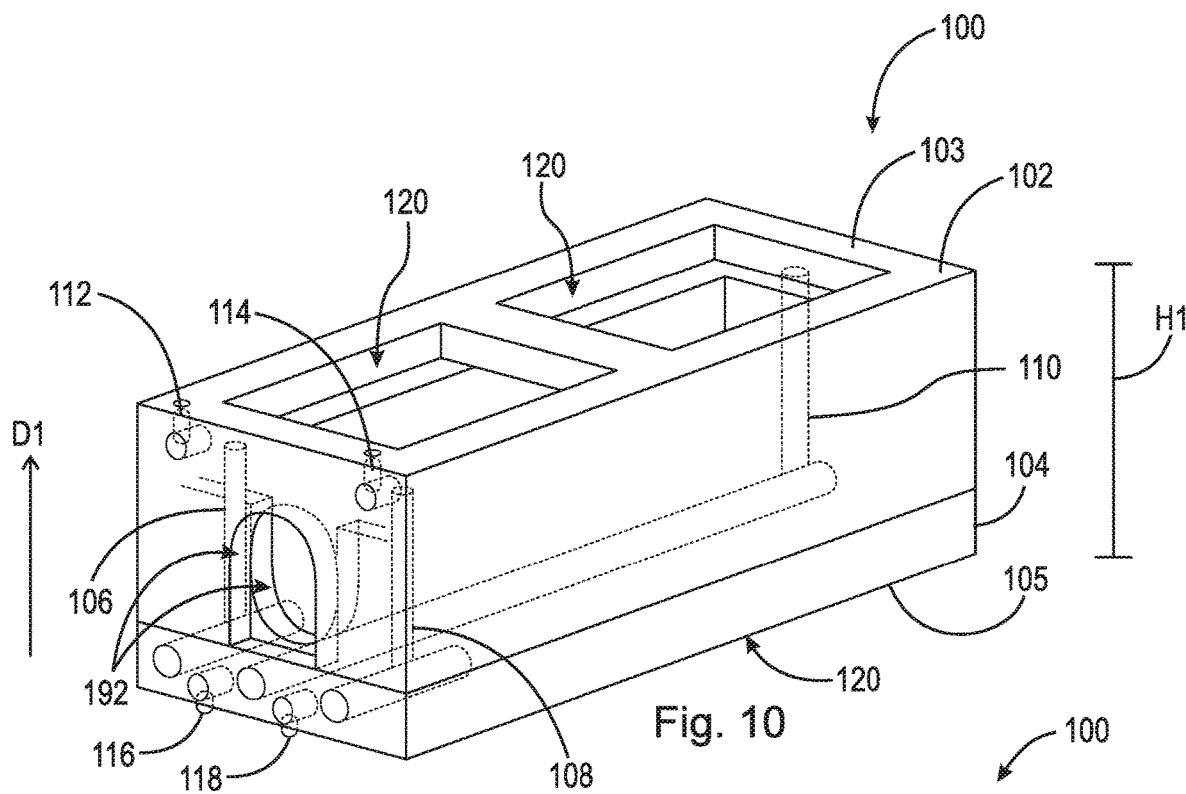
FIG. 10 is a perspective view of a first embodiment of the stand-alone expandable interbody spinal fusion device, in an unexpanded state.

FIG. 10 is a perspective view of stand-alone expandable interbody spinal fusion device 100, in an unexpanded state.

Device 100 comprises superior component 102, inferior component 104, and expansion mechanisms 106, 108, and 110 arranged to displace superior component 102 in a first direction D1 relative to inferior component 104 giving device 100 an expanded height $H_2$ greater than unexpanded height $H_1$, and self-piercing screw mechanisms 112, 114, 116, and 118, arranged to engage the bone material of the surrounding vertebra (i.e., L3 and L4). Superior component 102 and inferior component 104 further comprise at least one first aperture 120 arranged to allow fusion between bone fusing material and the adjacent vertebra, and a second aperture 192 located on the front face of device 100 and arranged to allow the introduction of bone fusing material into device 100. Second aperture 192 is illustrated as an arched slot as a non-limiting example, however, it should be appreciated that second aperture 192 could be any suitable aperture that would allow for the introduction of bone fusing material into device 100. Superior component 102 has a first surface 103 and inferior component 104 has a first surface 105. Embedded within the superior component, beneath surface 103, or above surface 103 (not depicted in FIG. 10), there is an anchor layer 107 (depicted in FIGS. 13 and 15). Embedded within the inferior component, beneath surface 105, or above surface 105 (not depicted in FIG. 10), there is an anchor layer 109 (depicted in FIGS. 13 and 15). Self-piercing screw mechanisms 112, 114, 116, and 118 can comprise the embodiment of either self-piercing screw mechanism 122 (as described infra) or self-piercing screw mechanism 146 (as described infra). Expansion mechanisms 106, 108, and 110 can comprise the embodiment of either expansion mechanism 166 or 178 (as described infra).

Figure 11:
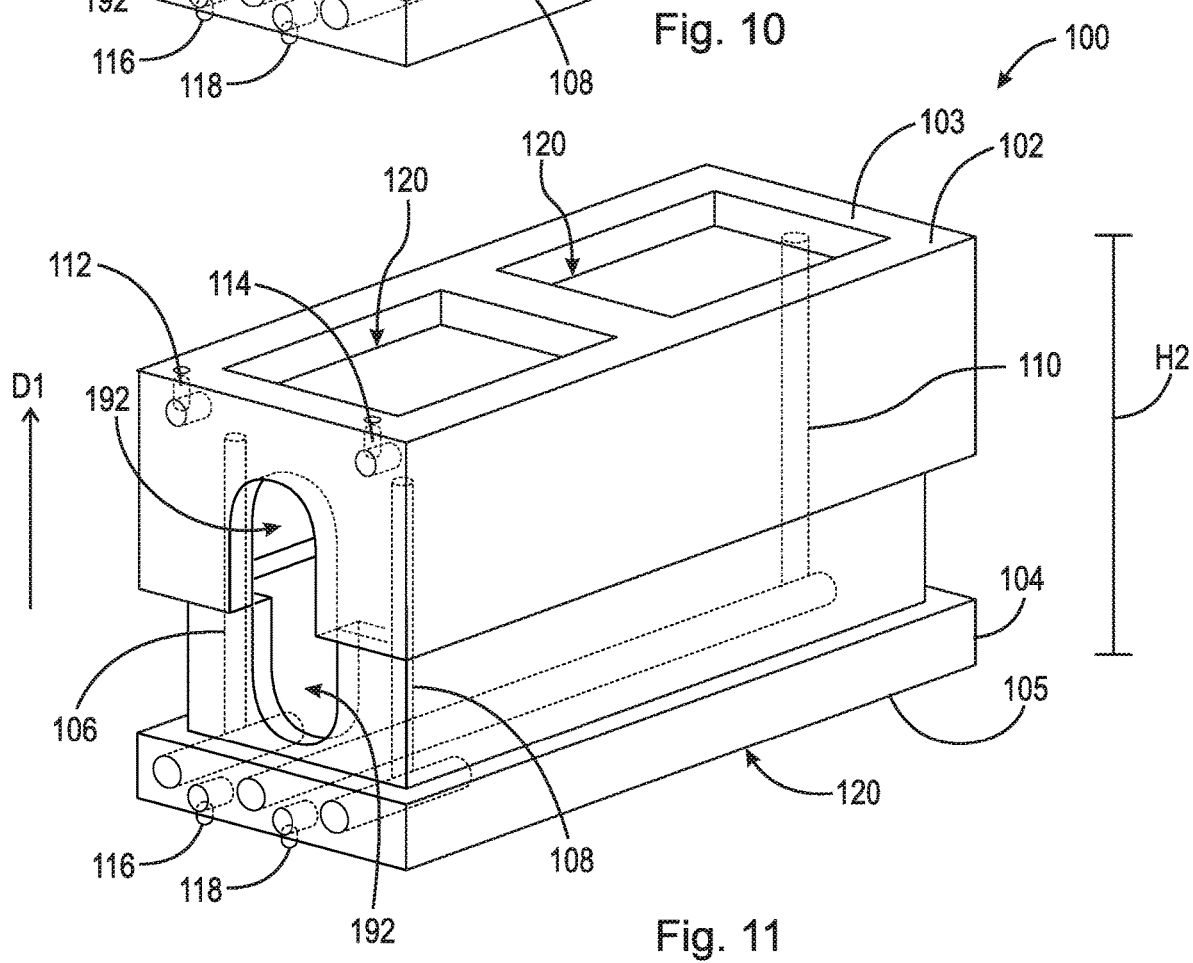
FIG. 11 is a perspective view of a first embodiment of the stand-alone expandable interbody spinal fusion device, in an expanded state.

FIG. 11 is a perspective view of stand-alone expandable interbody spinal fusion device 100, in an expanded state. During surgery and after device 100 is implanted in disc space 12, a surgeon can apply torque to expansion mechanisms 106, 108, and 110 via any device that imparts rotational force upon expansion mechanisms 106, 108, and 110 (e.g., a screw driver or impact driver). This rotational force causes expansion mechanisms 106, 108, and 110, to displace superior component 102 in direction D1 relative to inferior component 104 giving device 100 an expanded height $H_2$, greater than $H_1$. It should be appreciated that expansion mechanisms 106, 108, and 110, can be expanded to any height between unexpanded height $H_1$ and expanded height $H_2$.

Figure 12:
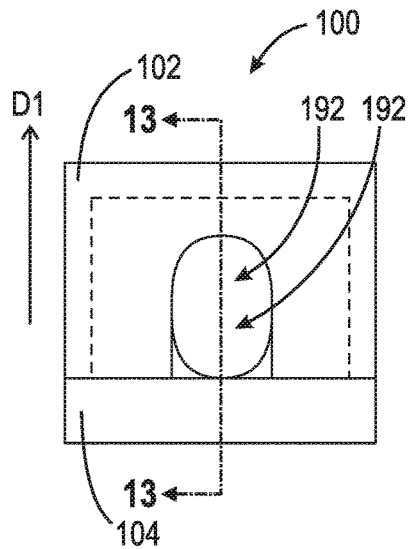
FIG. 12 is a front view of a first embodiment of the stand-alone expandable interbody spinal fusion device, in an unexpanded state.
Figure 13:
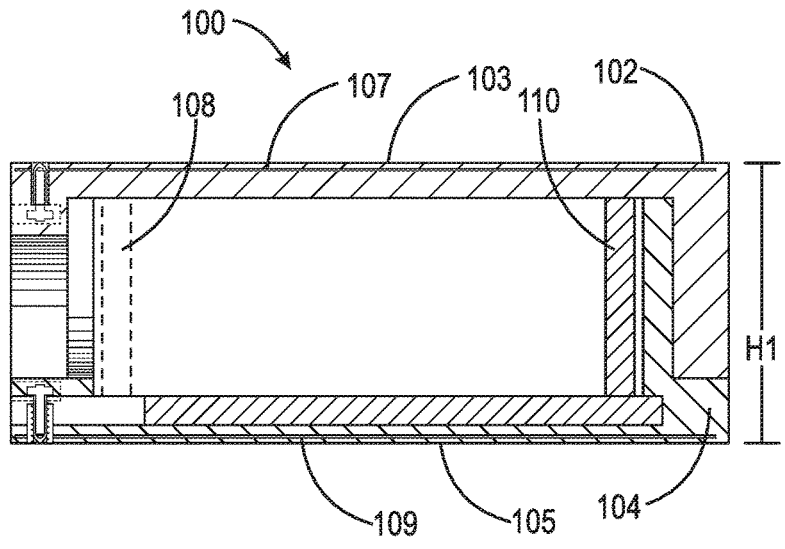
FIG. 13 is a cross-sectional view of a first embodiment of the stand-alone expandable interbody spinal fusion device, in an unexpanded state, taken generally along line 13-13 in FIG. 12.
Figure 14:
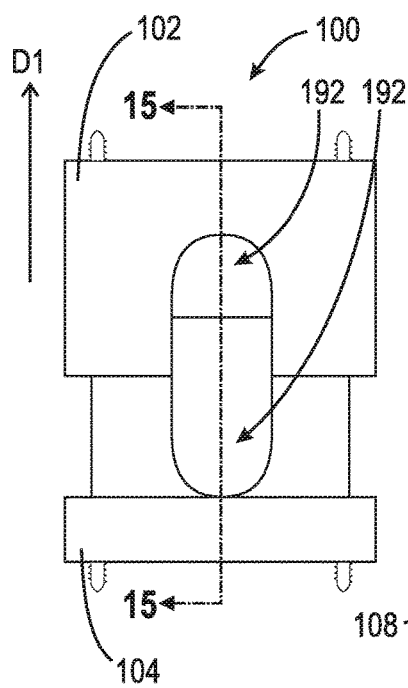
FIG. 14 is a front view of a first embodiment of the stand-alone expandable interbody spinal fusion device, in an expanded state.
Figure 15:
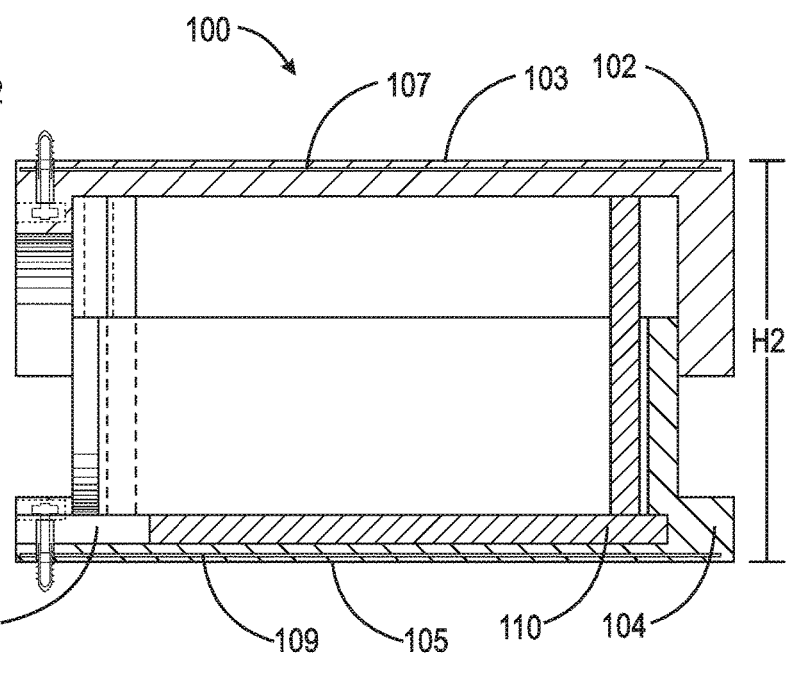
FIG. 15 is a cross-sectional view of a first embodiment of the stand-alone expandable interbody spinal fusion device, in an expanded state, taken generally along line 15-15 in FIG. 14.

FIG. 12 is a front view of stand-alone expandable interbody spinal fusion device 100, in an unexpanded state having an unexpanded height $H_1$. FIG. 13 is a cross-sectional view of stand-alone expandable interbody spinal fusion device 100, in an unexpanded state having an unexpanded height $H_1$. FIG. 14 is a front view stand-alone expandable interbody spinal fusion device 100, in an expanded state having an expanded height $H_2$, greater than $H_1$. FIG. 15 is a cross-sectional view stand-alone expandable interbody spinal fusion device 100, in an expanded state having an expanded height $H_2$, greater than $H_1$.

Figure 16:
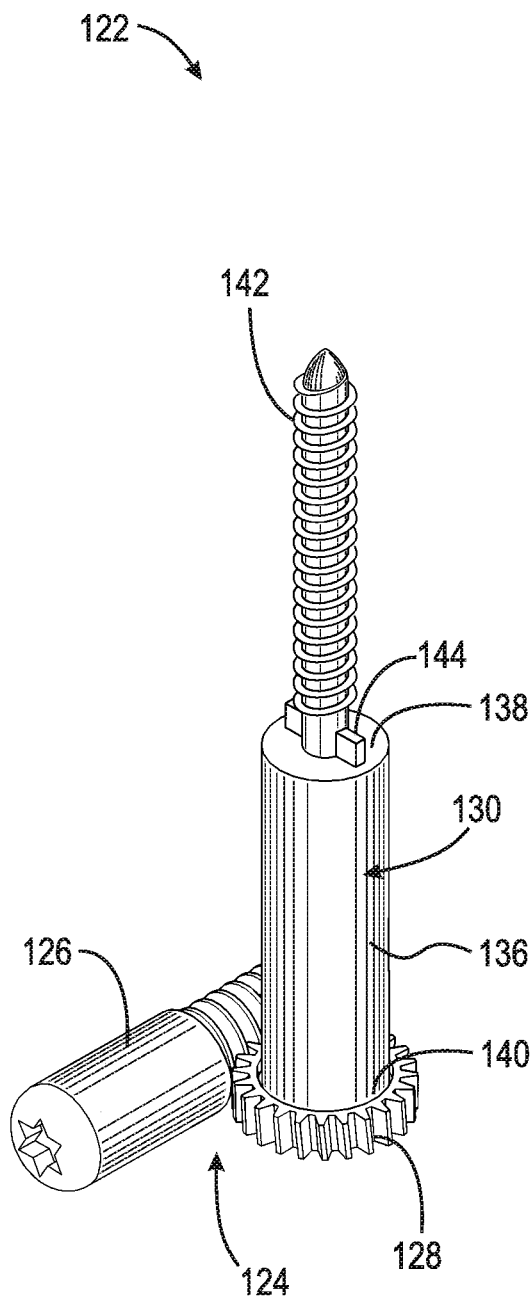
FIG. 16 is a perspective view of a first embodiment of a self-piercing screw mechanism in an unexpanded state.

FIG. 16 is a perspective view of a self-piercing screw mechanism 122 in an unexpanded state. Self-piercing screw mechanism 122 comprises a worm drive 124 having a worm 126 and a gear 128; a drive casing 130 having an inner radial surface 132 that has a keyed shaft 134 (not shown in this figure), an outer radial surface 136, a first end 138, and a second end 140; and, self-piercing screw body 142 having tab 144. The second end 140 is fixedly secured to gear 128. During surgery and after device 100 is implanted in disc space 12, a surgeon can apply torque to worm drive 124 via any device that imparts rotational force upon worm 126 (e.g., a screw driver or impact driver). Torque is transferred 90 degrees through worm drive 124, via worm 126 and gear 128. Rotation of gear 128 causes drive casing 130 to rotate. As drive casing 130 rotates, keyed shaft 134 engages tab 144 and imparts rotational force to self-piercing screw body 142. It should be appreciated that worm drive 124 could be arranged to transfer torque in other arrangements, i.e., 180 degrees, 270 degrees, or any desirable angle required by the arrangement of worm 126 and gear 128. It should further be appreciated that, although gear 128 is depicted in the figures as a spur gear, other suitable gears may be selected, i.e., a bevel gear, a hypoid gear, a spiral gear, or a face gear. Additionally, self-piercing screw body 142 may have more than one tab 144.

Figure 17:
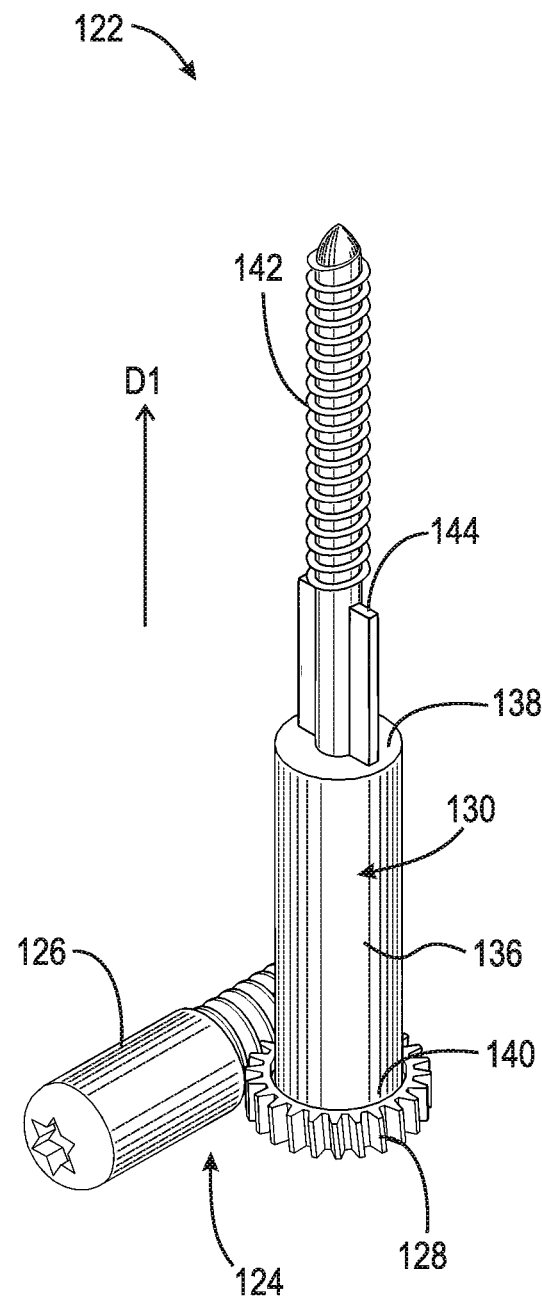
FIG. 17 is a perspective view of a first embodiment of a self-piercing screw mechanism in an expanded state.

FIG. 17 is a perspective view of self-piercing screw mechanism 122 in an expanded state. As discussed above, as drive casing 130 rotates, keyed shaft 134 engages tab 144 and imparts rotational force to self-piercing screw body 142. Self-piercing screw body 142 rotates it engages with either anchor layer 107, if self-piercing screw body 142 is embedded within superior component 102; or, anchor layer 109, if self-piercing screw body 142 is embedded within inferior component 104. As self-piercing screw body 142 engages either anchor layer 107 or anchor layer 109, the self-piercing screw body further engages the bone material of the adjacent vertebra (e.g., L3 or L4). As self-piercing screw body 142 engages bone material, tab 144 continues to transfer torque to the screw body and slides along keyed shaft 134. When the screw body is at its maximum expansion, tab 144 abuts either anchor layer 107 or anchor layer 109 and can no longer screw deeper into the bone material of the adjacent vertebra.

Figure 18:
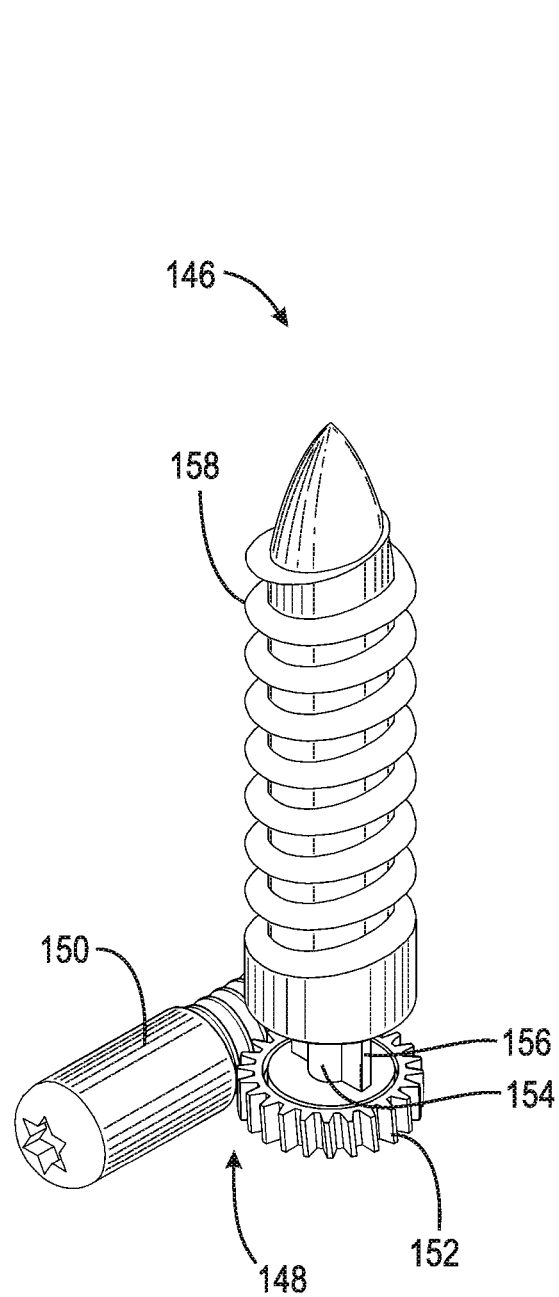
FIG. 18 is a perspective view of a second embodiment of a self-piercing screw mechanism in an unexpanded state.

FIG. 18 is a perspective view of self-piercing screw mechanism 146 in an unexpanded state. Self-piercing screw mechanism 146 comprises a worm drive 148 having a worm 150 and a gear 152. Gear 152 is fixedly secured to rod 154. Rod 154 has a tab 156 and a flange 157 (not shown in FIG. 18). Self-piercing screw mechanism 146 further comprises a self-piercing screw body 158 having a partial through bore 160 with an inner radial surface 162 that has a keyed shaft 164 (not depicted in FIG. 18), arranged to slidingly engage tab 156, and a retention shoulder 159 (not depicted in FIG. 18). During surgery and after device 100 is implanted in disc space 12, a surgeon can apply torque to worm drive 148 via any device that imparts rotational force upon worm 150 (e.g., a screw driver or impact driver). Torque is transferred 90 degrees through worm drive 148, via worm 150 and gear 152. Rotation of gear 152 causes rod 154 to rotate. As rod 154 rotates, tab 156 engages keyed shaft 164 within the partial through bore 160 of self-piercing screw body 158 and imparts rotational force to self-piercing screw body 158. It should be appreciated that worm drive 148 could be arranged to transfer torque in other arrangements, i.e., 180 degrees, 270 degrees, or any desirable angle required by the arrangement of worm 150 and gear 152. It should further be appreciated that although a gear 158 is depicted in the figures as a spur gear, other suitable gears may be selected, i.e., a bevel gear, a hypoid gear, a spiral gear, or a face gear.

Figure 19:
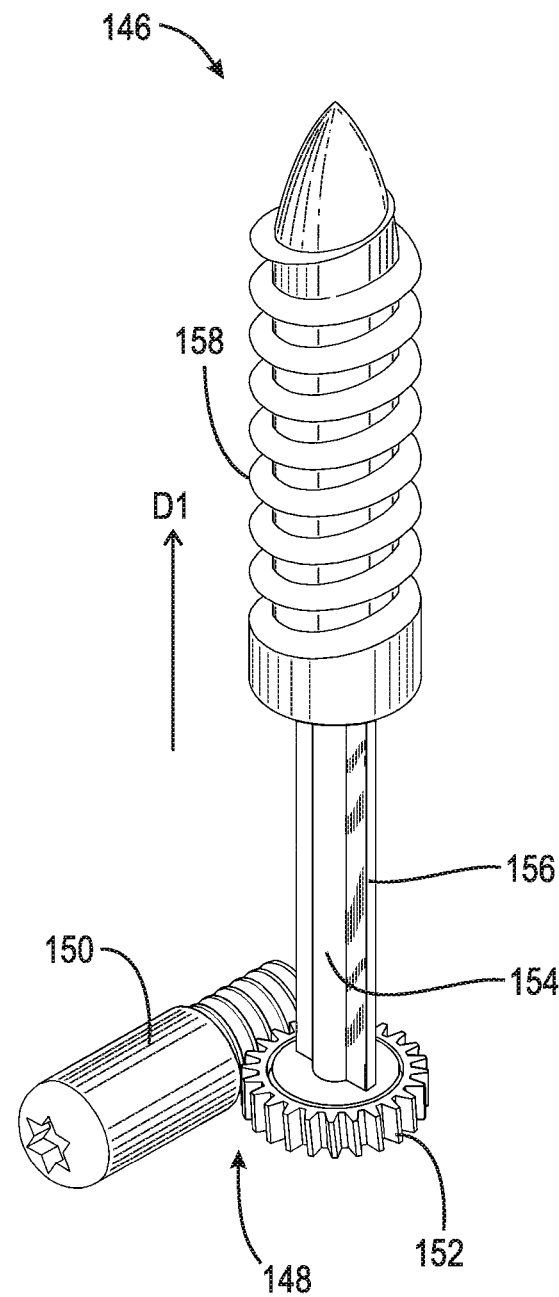
FIG. 19 is a perspective view of a second embodiment of a self-piercing screw mechanism in an expanded state.

FIG. 19 is a perspective view of self-piercing screw mechanism 146 in an expanded state. As discussed above, as rod 154 rotates, tab 156 engages keyed shaft 164 within the partial through bore 160 (depicted in FIG. 31) of self-piercing screw body 158 and imparts rotational force to self-piercing screw body 158. As self-piercing screw body 158 rotates it engages with either anchor layer 107, if self-piercing screw body 158 is embedded within superior component 102; or, anchor layer 109, if self-piercing screw body 158 is embedded within inferior component 104. As self-piercing screw body 158 engages either anchor layer 107 or anchor layer 109, the self-piercing screw body is drawn deeper into, and further engages, the bone material of the adjacent vertebra (e.g., L3 or L4). As self-piercing screw body 158 engages bone material, tab 156 continues to transfer torque to the screw body and slides along keyed shaft 164 with inner radial surface 162 of partial through bore 160. When the screw body is at its maximum expansion flange 157 abuts retention shoulder 159 preventing the screw body from moving deeper into the bone material of the adjacent vertebra.

FIG. 20 is a side view self-piercing screw mechanism 122 in an unexpanded state. FIG. 21 is a side view of self-piercing screw mechanism 122 in an unexpanded state rotated 90 degrees. FIG. 22 is a cross-sectional view of self-piercing screw mechanism 122 in an unexpanded state, taken generally along line 22-22 in FIG. 21.

Figure 23:
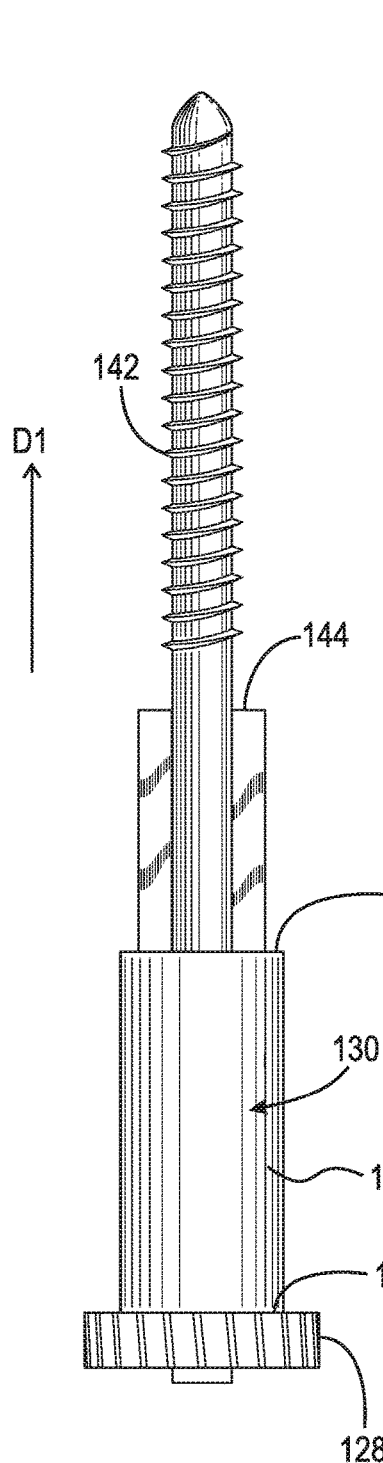
FIG. 23 is a side view of a first embodiment of a self-piercing screw mechanism in an expanded state.
Figure 24:
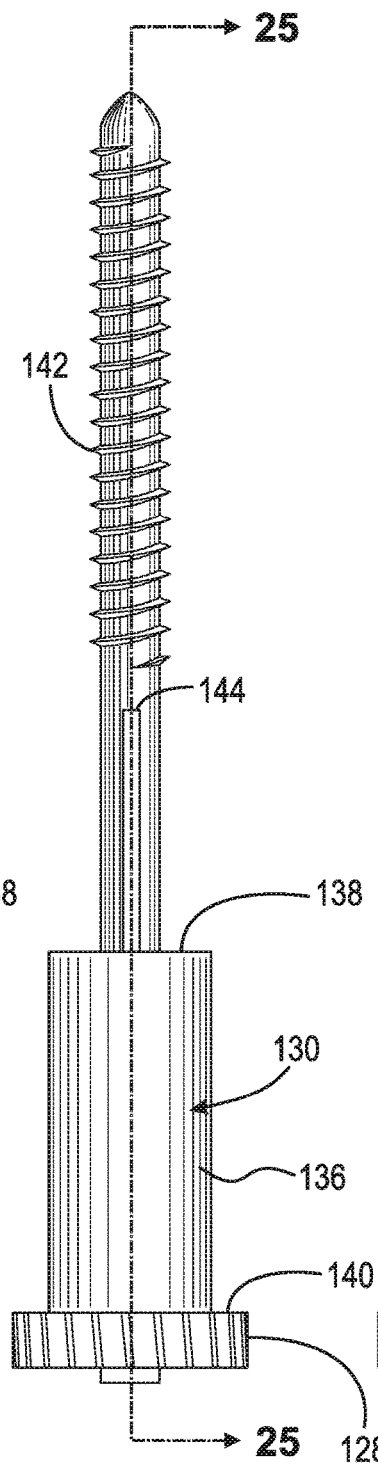
FIG. 24 is a side view of a first embodiment of a self-piercing screw mechanism in an expanded state.
Figure 25:
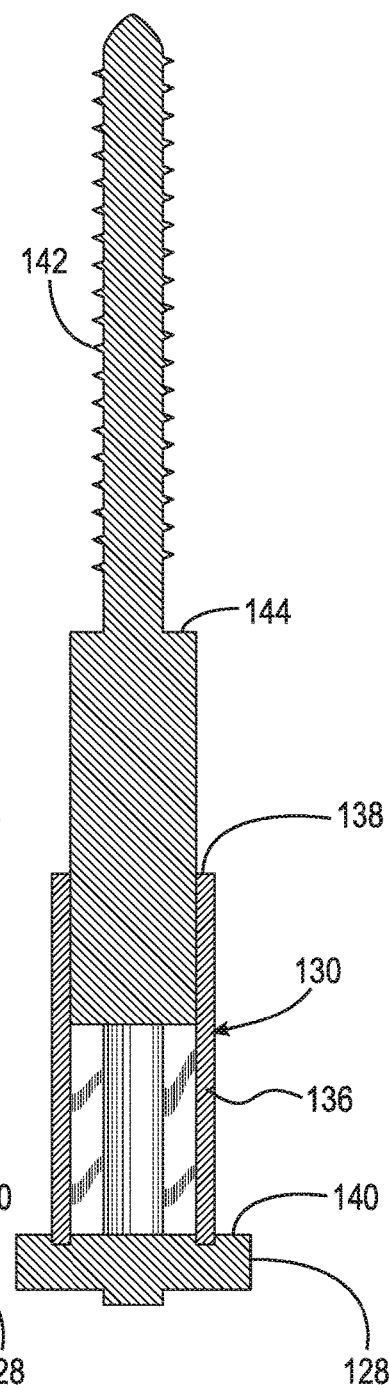
FIG. 25 is a cross-sectional view of a first embodiment of a self-piercing screw mechanism is an expanded state, taken generally along line 25-25 in FIG. 24.

FIG. 23 is a side view self-piercing screw mechanism 122 in an expanded state. FIG. 24 is a side view of self-piercing screw mechanism 122 in an expanded state rotated 90 degrees. FIG. 25 is a cross-sectional view of self-piercing screw mechanism 122 in an expanded state, taken generally along line 25-25 in FIG. 24.

Figure 26:
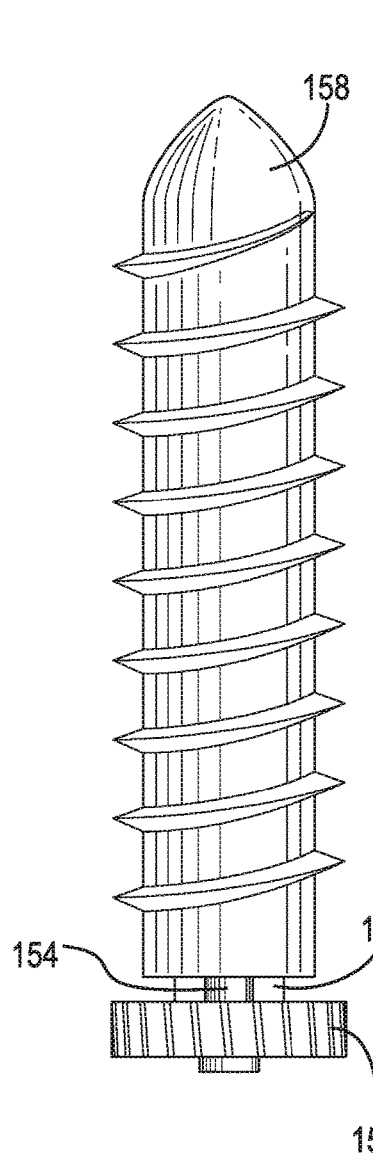
FIG. 26 is a side view of a second embodiment of a self-piercing screw mechanism in an unexpanded state.
Figure 27:
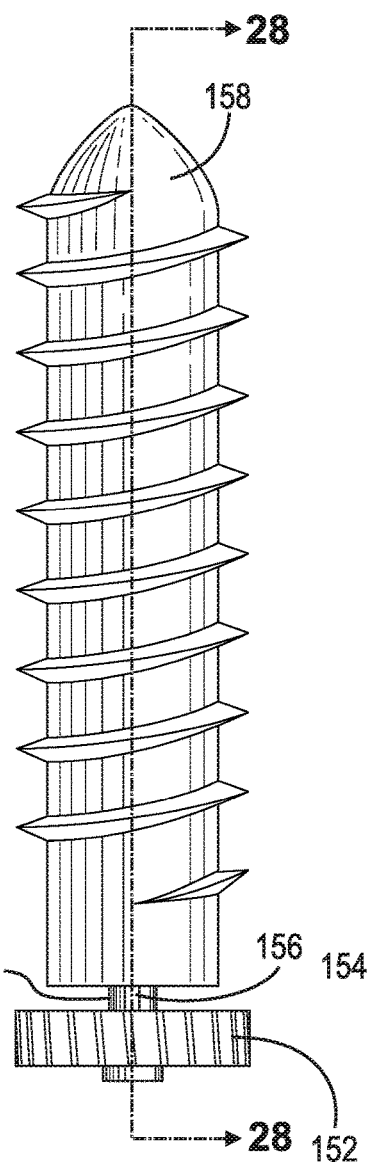
FIG. 27 is a side view of a second embodiment of a self-piercing screw mechanism in an unexpanded state.
Figure 28:
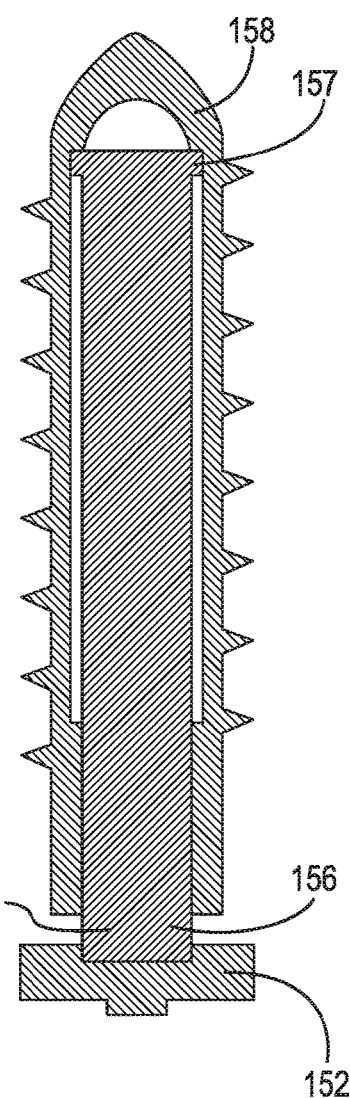
FIG. 28 is a cross-sectional view of a second embodiment of a self-piercing screw mechanism is an unexpanded state, taken generally along line 28-28 in FIG. 27.

FIG. 26 is a side view self-piercing screw mechanism 146 in an unexpanded state. FIG. 27 is a side view of self-piercing screw mechanism 146 in an unexpanded state rotated 90 degrees. FIG. 28 is a cross-sectional view of self-piercing screw mechanism 146 in an unexpanded state, taken generally along line 28-28 in FIG. 27.

Figure 29:
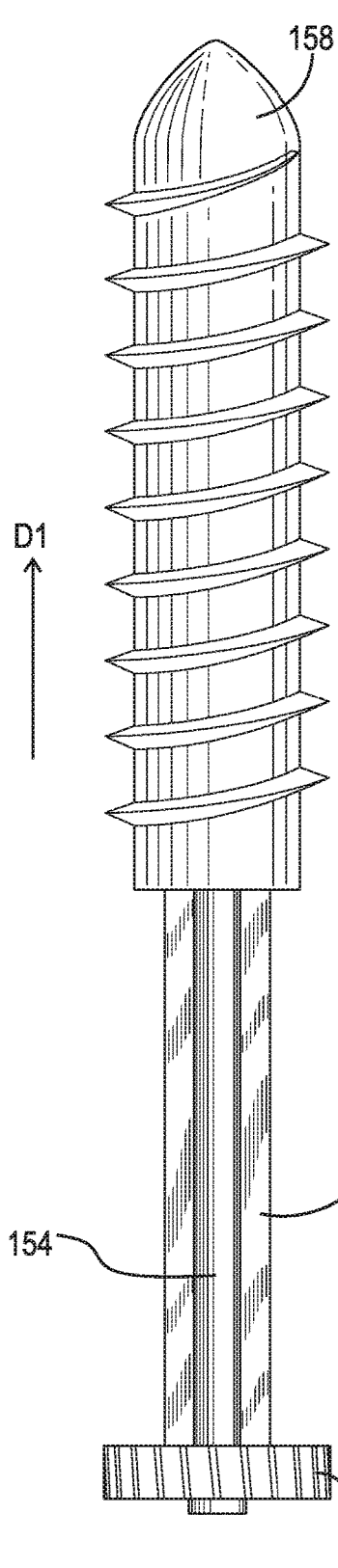
FIG. 29 is a side view of a second embodiment of a self-piercing screw mechanism in an expanded state.
Figure 30:
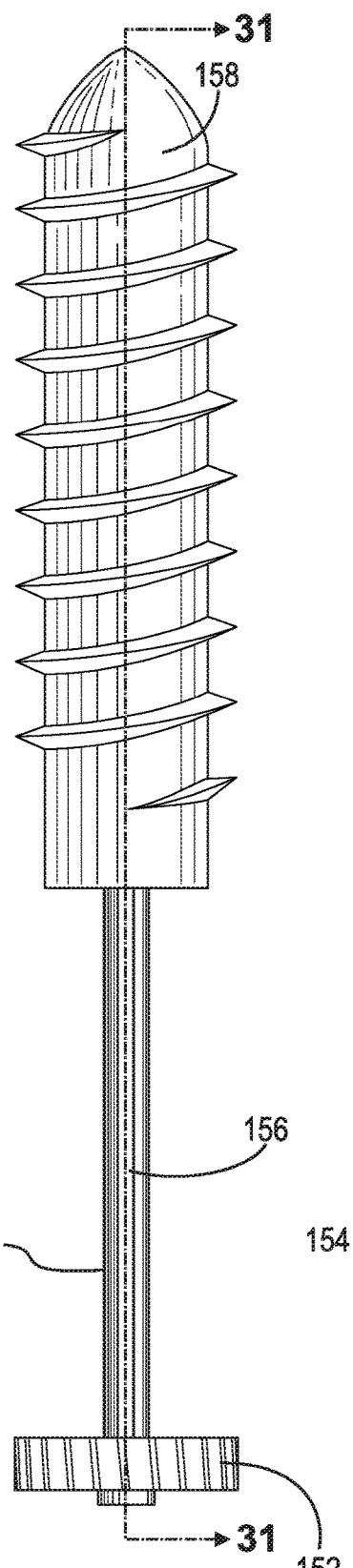
FIG. 30 is a side view of a second embodiment of a self-piercing screw mechanism in an expanded state.
Figure 31:
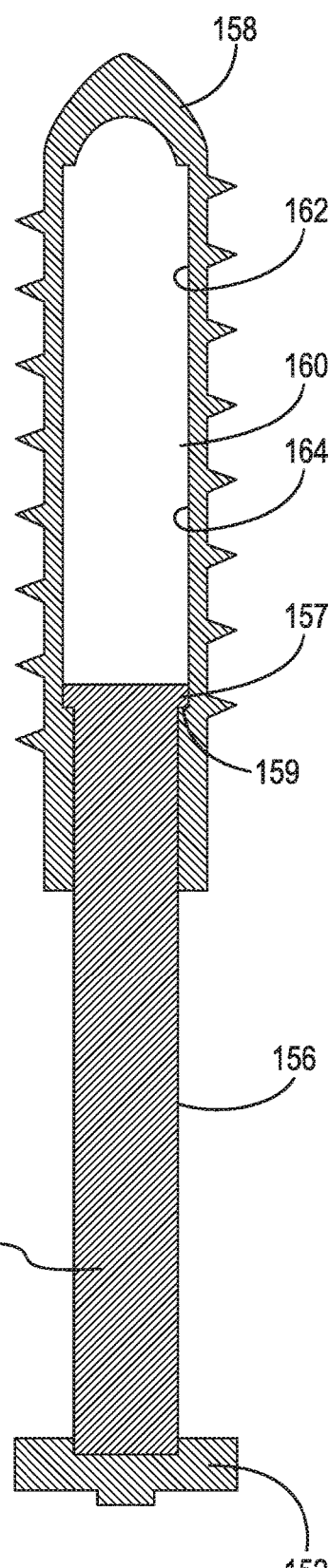
FIG. 31 is a cross-sectional view of a second embodiment of a self-piercing screw mechanism is an expanded state, taken generally along line 31-31 in FIG. 30.

FIG. 29 is a side view self-piercing screw mechanism 146 in an expanded state. FIG. 30 is a side view of self-piercing screw mechanism 146 in an expanded state rotated 90 degrees. FIG. 31 is a cross-sectional view of self-piercing screw mechanism 146 in an expanded state, taken generally along line 31-31 in FIG. 30.

Figures 32, 33:
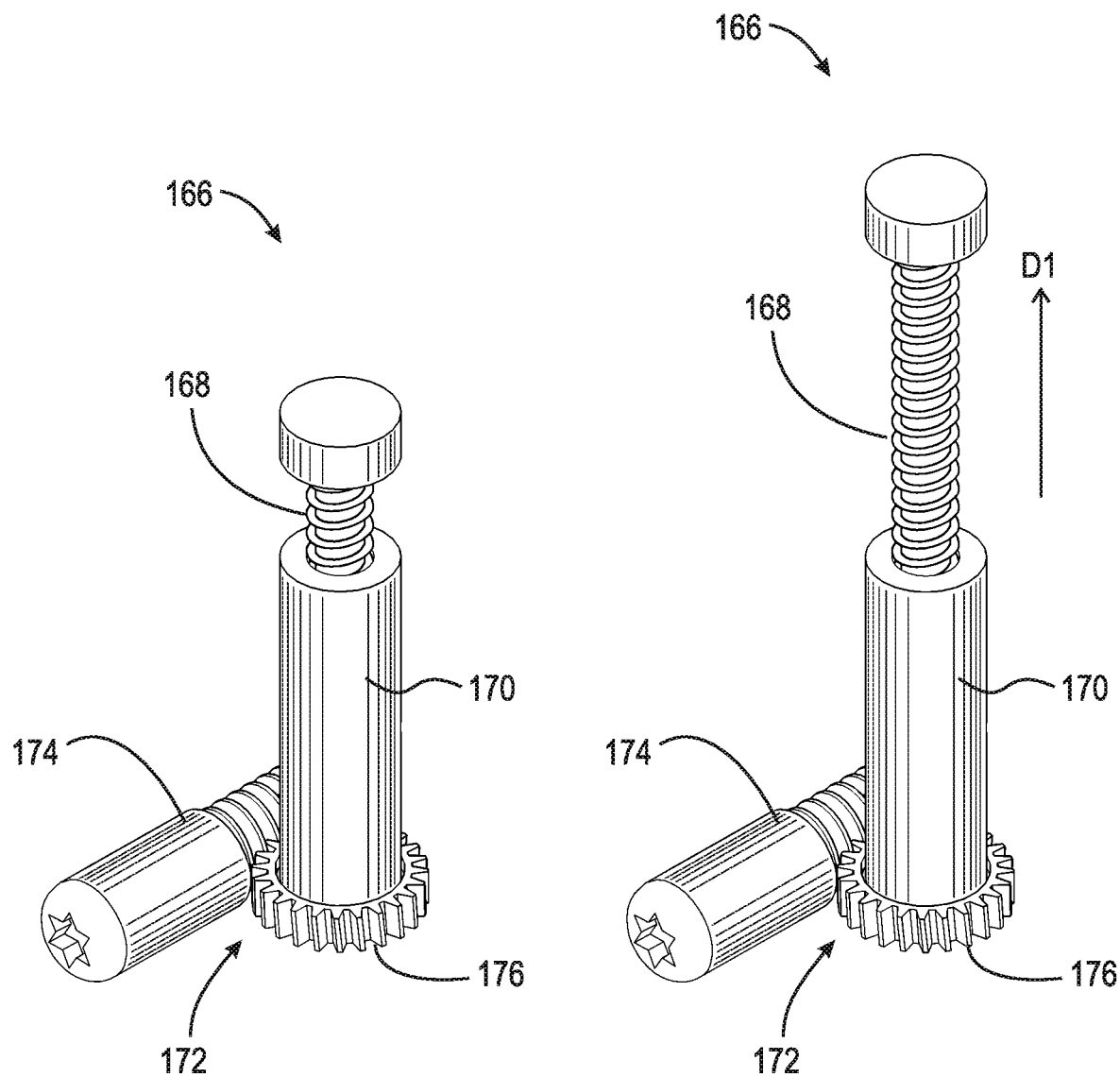
FIG. 32 is a perspective view of a first embodiment of an expansion mechanism in an unexpanded state.
FIG. 33 is a perspective view of a first embodiment of an expansion mechanism in an expanded state.

FIG. 32 is a perspective view of an expansion mechanism 166 in an unexpanded state. Expansion mechanism 166 comprises threaded rod 168, threaded sleeve 170, a worm drive 172 having a worm 174 and a gear 176. A portion of threaded rod 168 can be embedded within superior component 102 such that it is rotationally fixed. It should be appreciated that although expansion mechanism 166 is depicted within inferior component 104, expansion mechanism could be arranged within superior component 102. During surgery and after device 100 is implanted in disc space 12, a surgeon can apply torque to worm drive 172 via any device that imparts rotational force upon worm 174 (e.g., a screw driver or impact driver). Torque is transferred 90 degrees through worm drive 172, via worm 174 and gear 176. Rotation of gear 176 causes threaded sleeve 170 to rotate. As threaded sleeve 170 rotates, threaded rod remains rotationally locked due to the portion embedded within superior component 102. As threaded sleeve 170 rotates, the threads of the rotationally locked threaded rod 168 ride upward along the threads within threaded sleeve 170, this displaces threaded rod, and subsequently superior component 102 in direction D1. Threaded rod 168 includes a stopping feature to prevent threaded rod 168 from being ejected from threaded sleeve 170. For example, the lower portion of threaded rod 168 could be threadless (shown in FIG. 36), and therefore prevent threaded rod 168 from being ejected from threaded sleeve 170. When threaded rod 168 reaches its maximum expansion, the unthreaded portion of rod 168 remains within threaded sleeve 170, preventing threaded rod 168 from being pushed out of threaded sleeve 170. Alternatively, the stopping feature could be a flange on the recessed portion of threaded rod 168 arranged to engage with a retention shoulder within threaded sleeve 170 in a fully expanded state (not shown in the Figures). It should be appreciated that worm drive 172 could be arranged to transfer torque in other arrangements, i.e., 180 degrees, 270 degrees, or any desirable angle required by the arrangement of worm 174 and gear 176. It should further be appreciated that although a gear 176 is depicted in the figures as a spur gear, other suitable gears may be selected, i.e., a bevel gear, a hypoid gear, a spiral gear, or a face gear. FIG. 33 is a perspective view of an expansion mechanism 166 in an expanded state.

Figures 34, 35, 36:
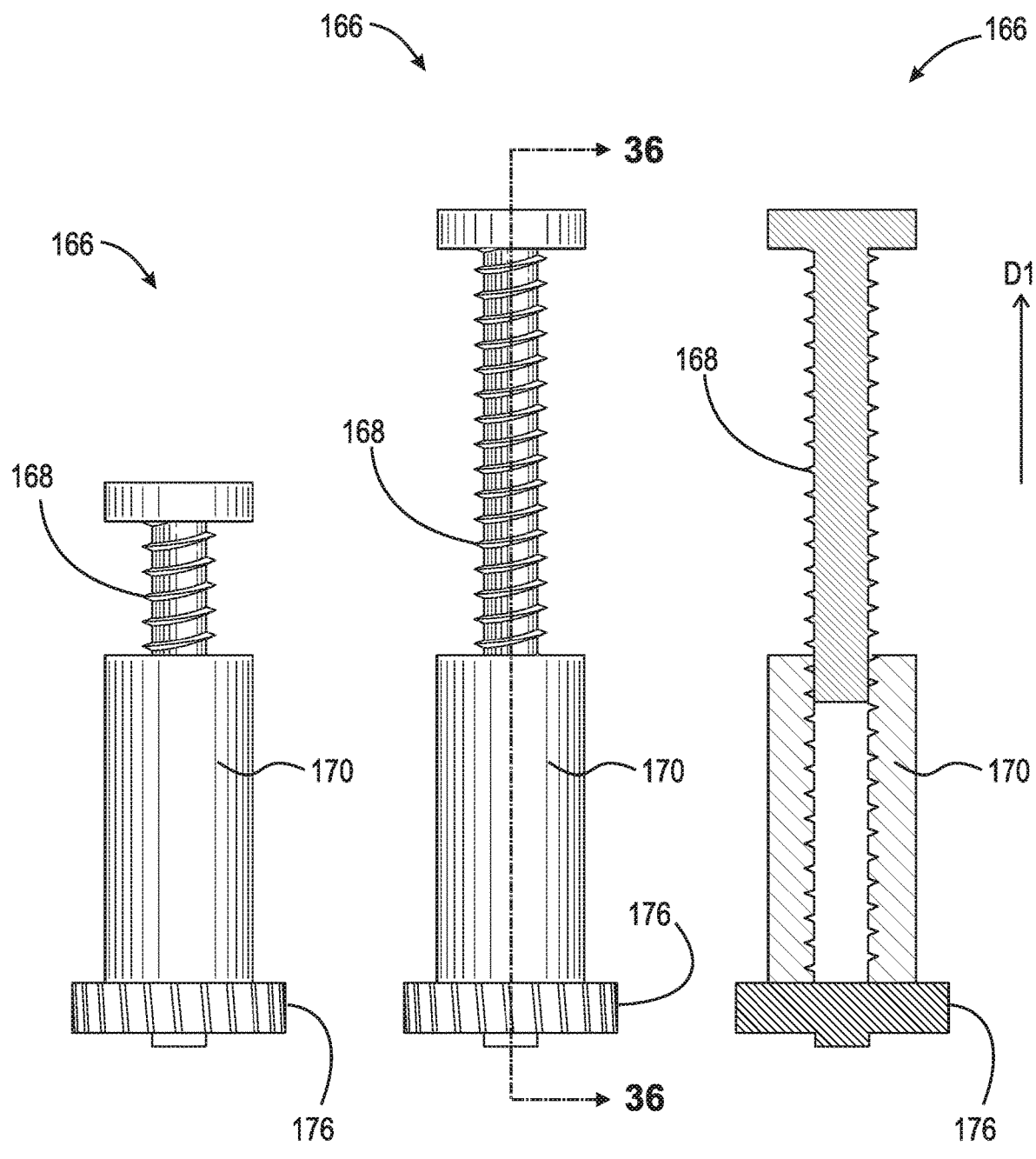
FIG. 34 is a side view of a first embodiment of an expansion mechanism in an unexpanded state.
FIG. 35 is a side view of a first embodiment of an expansion mechanism in an expanded state.
FIG. 36 is a cross-sectional view of a first embodiment of an expansion mechanism in an expanded state taken generally along line 36-36 in FIG. 35.

FIG. 34 is a side view of expansion mechanism 166 in an unexpanded state. FIG. 35 is a side view of expansion mechanism 166 rotated 90 degrees in an expanded state. FIG. 36 is a cross-sectional view of expansion mechanism 166, taken generally along line 36-36 in FIG. 35.

Figure 37:
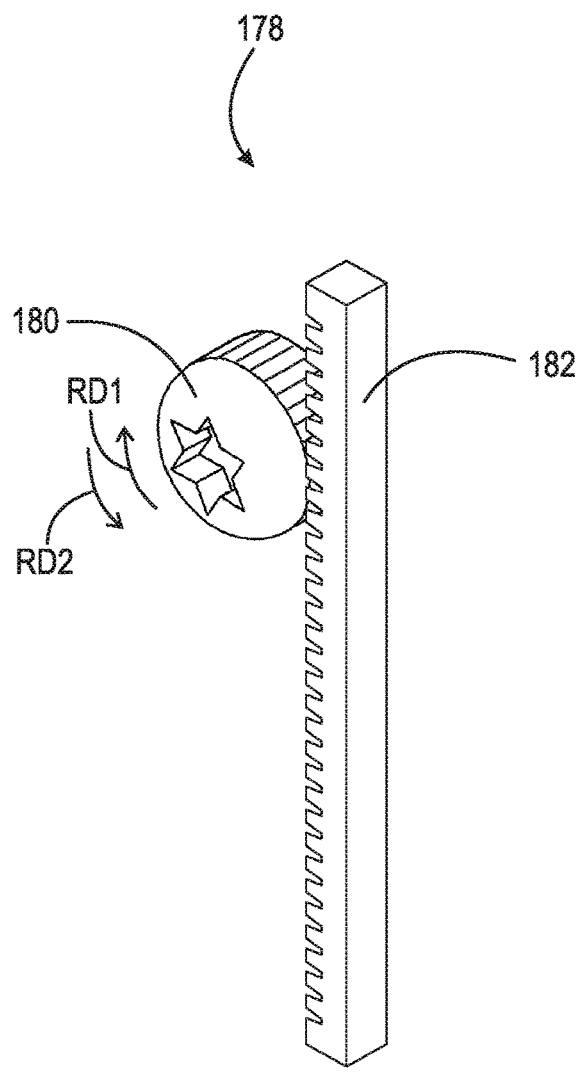
FIG. 37 is a perspective view of a second embodiment of an expansion mechanism in an unexpanded state.
Figure 38:
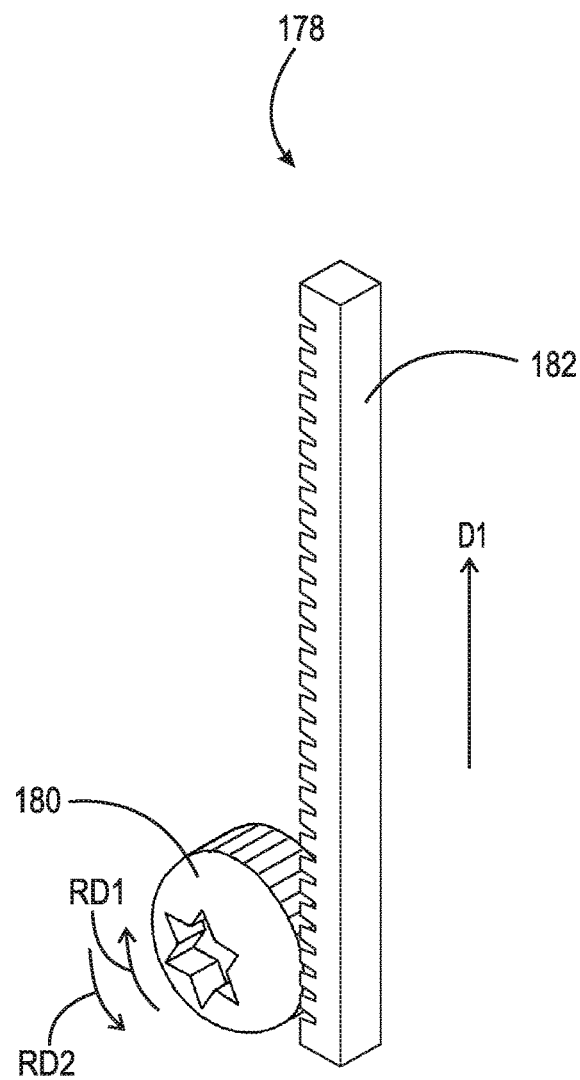
FIG. 38 is a perspective view of a second embodiment of an expansion mechanism in an expanded state.
Figures 39, 40:
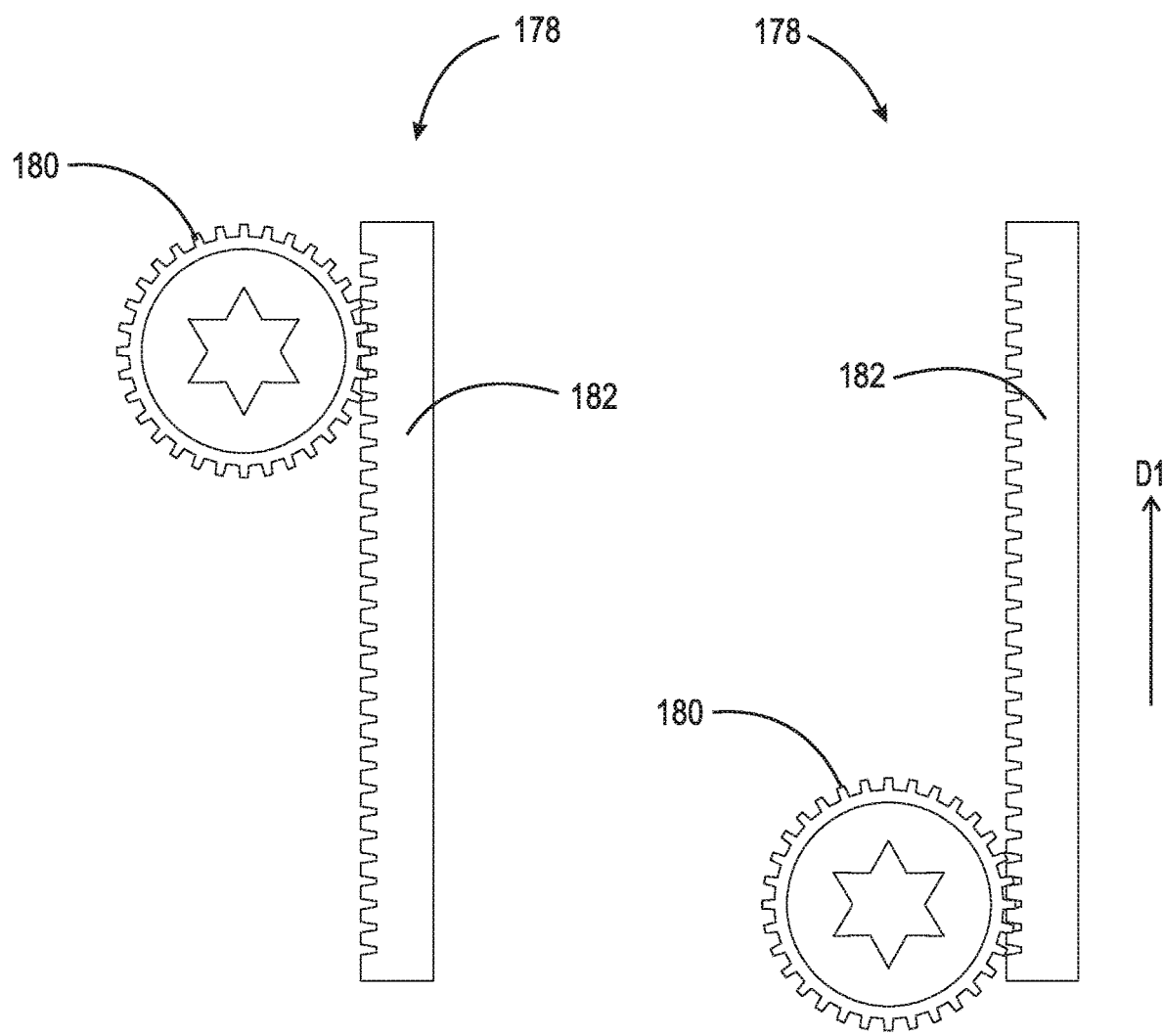
FIG. 39 is a side view of a second embodiment of an expansion mechanism in an unexpanded state.
FIG. 40 is a side view of a second embodiment of an expansion mechanism in an expanded state.

FIG. 37 is a perspective view of expansion mechanism 178 in an unexpanded state. Expansion mechanism 178 comprises a gear 180 and a toothed shaft 182. Gear 180 and toothed shaft 182 are arranged within inferior component 104; however, they could be arranged within superior component 102 (not shown). During surgery and after device 100 is implanted in disc space 12, a surgeon can apply torque to gear 180 via any device that imparts rotational force (e.g., a screw driver or impact driver). Torque is transferred 90 degrees through gear 180 to toothed shaft 182. When gear 180 is rotated in rotational direction RD2 opposite RD1, superior component 102 is displace in direction D1. FIG. 38 is a perspective view of expansion mechanism 178 in an expanded state after rotation of gear 180 in direction RD2. It should be appreciated that although a gear 180 is depicted in the figures as a spur gear, other suitable gears may be selected, i.e., a bevel gear, a hypoid gear, a spiral gear, or a face gear. FIG. 39 is a side view of expansion mechanism 178 in an unexpanded state. FIG. 40 is a side view of expansion mechanism 178 is an expanded state.

Figure 41:
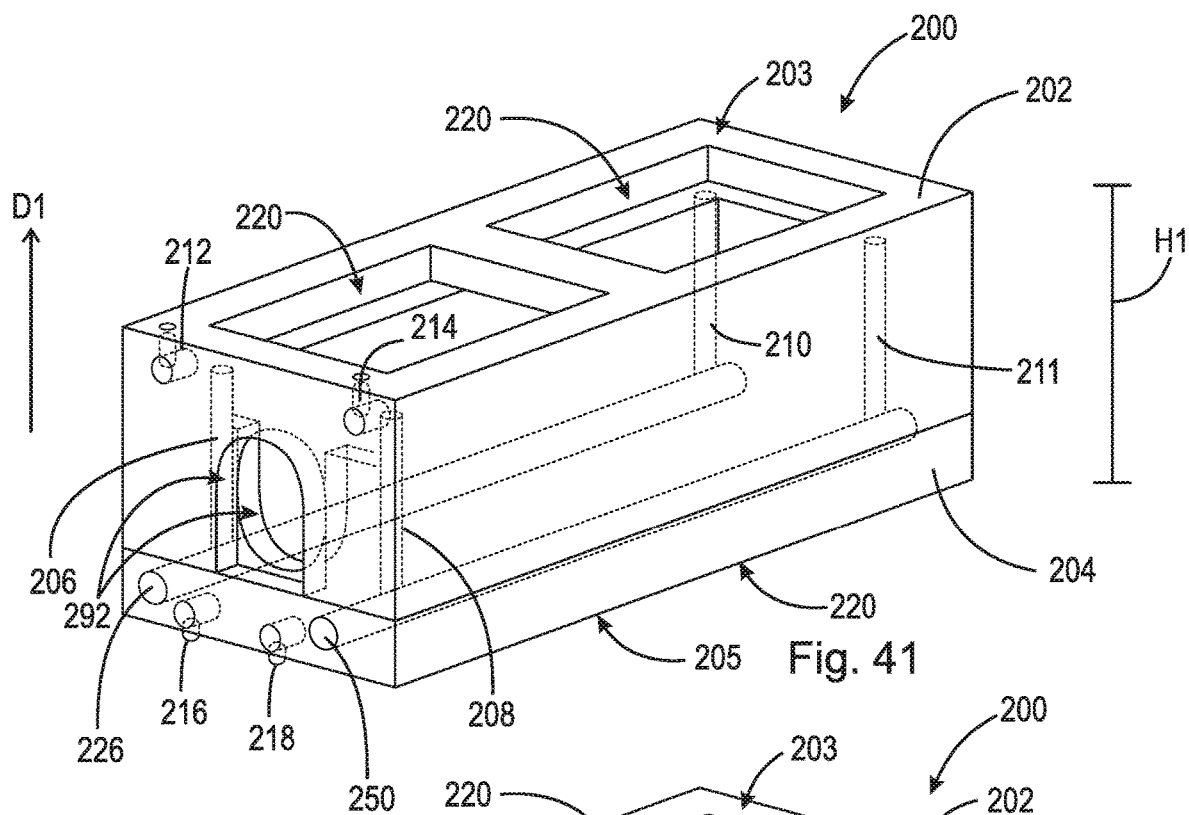
FIG. 41 is a perspective view of a second embodiment of the stand-alone expandable interbody spinal fusion device, in an unexpanded state.

FIG. 41 is a perspective view of stand-alone expandable interbody spinal fusion device 200 in an unexpanded state. Device 200 comprises superior component 202, inferior component 204, and expansion mechanisms 206, 208, 210, and 211, arranged to displace superior component 202 in a first direction D1 relative to inferior component 204 giving device 200 an expanded height $H_2$ greater than unexpanded height $H_1$, self-piercing screw mechanisms 212, 214, 216, and 218, arranged to engage the bone material of the surrounding vertebra (i.e., L3 and L4). Superior component 202 and inferior component 204 further comprise at least one first aperture 220 arranged to allow fusion between bone fusing material and the adjacent vertebra, and a second aperture 292 located on the front face of device 200 arranged to allow the introduction of bone fusing material into device 200. Second aperture 292 is illustrated as an arched slot as a non-limiting example, however, it should be appreciated that second aperture 292 could be any suitable aperture that would allow for the introduction of bone fusing material into device 200. Superior component 202 has a first surface 203 and inferior component 204 has a first surface 205. Embedded within the superior component, beneath surface 203, or above surface 203 (not depicted in FIG. 41), there is an anchor layer 207. Embedded within the inferior component, beneath surface 205, or above surface 205 (not depicted in FIG. 41), there is an anchor layer 209. Self-piercing screw mechanisms 212, 214, 216, and 218 can comprise the embodiment of either self-piercing screw mechanism 122 (as described supra) or self-piercing screw mechanism 146 (as described supra). Expansion mechanisms 206, 208, 210, and 211 can comprise the embodiment of either expansion mechanism 166 or 178 (as described infra).

Figure 42:
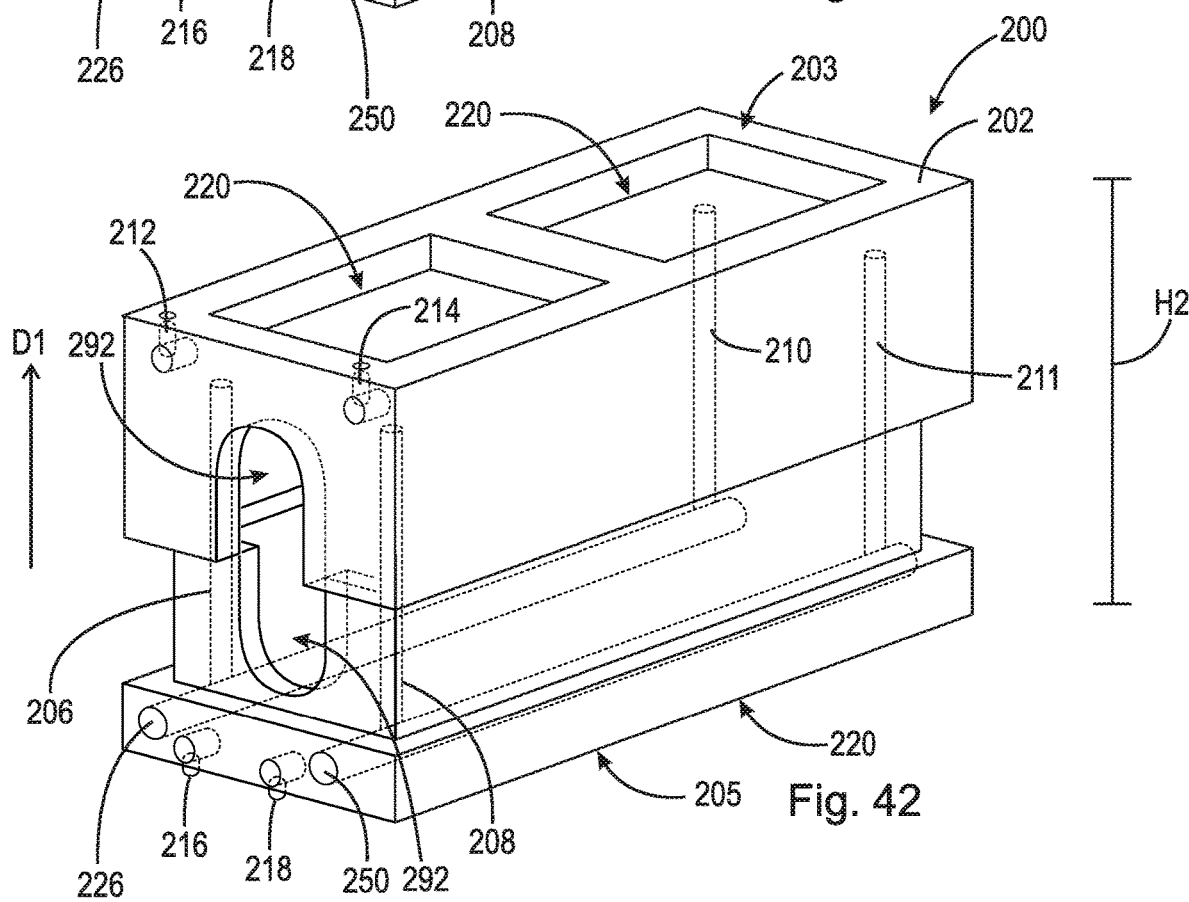
FIG. 42 is a perspective view of a second embodiment of the stand-alone expandable interbody spinal fusion device, in an expanded state.

FIG. 42 is a perspective view of stand-alone expandable interbody spinal fusion device 200, in an expanded state. During surgery and after device 200 is implanted into disc space 12, a surgeon can apply torque to expansion mechanisms 206, 208, 210 and 211 via any device that imparts rotational force (e.g., a screw driver or impact driver). The rotational force causes expansion mechanisms 206, 208, 210 and 211 to displace superior component 202 in direction D1 relative to inferior component 204, giving device 200 an expanded height $H_2$ greater than $H_1$. This embodiment of the implant differs from stand-alone expandable interbody spinal fusion device 100, as illustrated in FIGS. 10 and 11, in that it has an additional expansion mechanism, and there are two gear shafts 226 and 250 in place of individual worms 126 or 150. Gear shaft 226 is arranged to engage expansion mechanisms 206 and 210, and gear shaft 250 is arranged to engage expansion mechanisms 208 and 211. Although not shown in FIG. 41 or 42 it is possible to vary the thread ratio of each expansion mechanism allowing for an uneven expansion of superior component 202.

Figure 43:
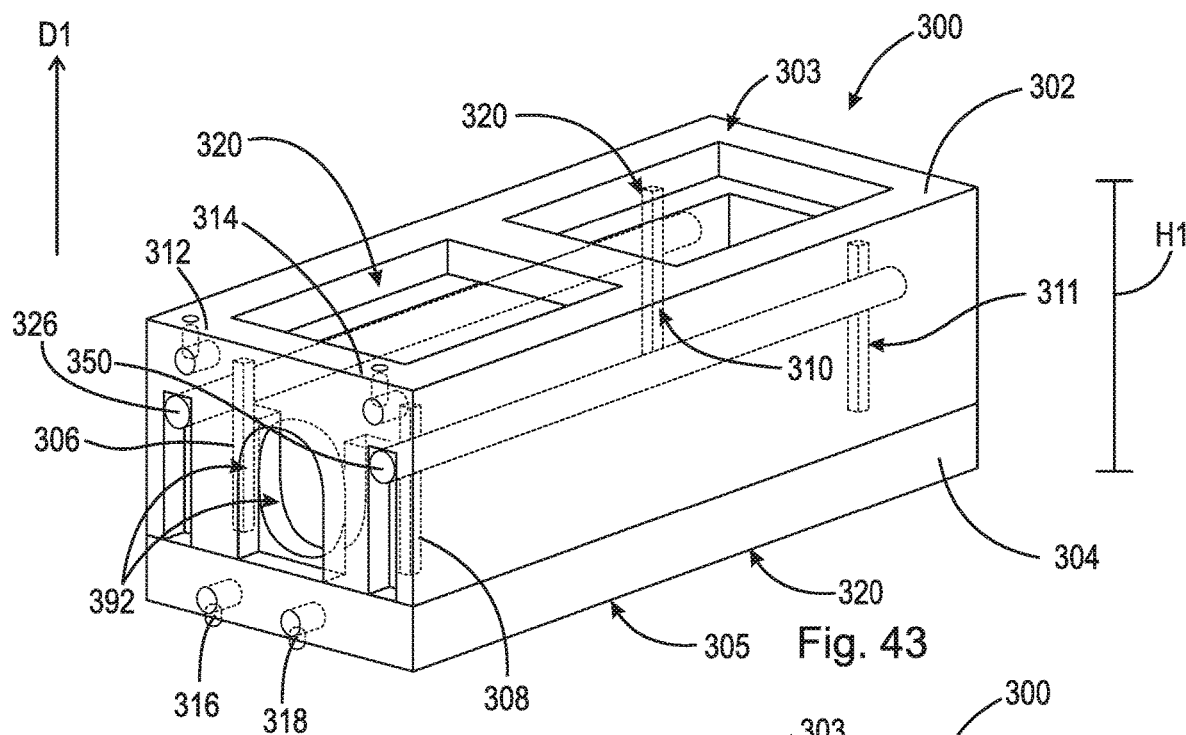
FIG. 43 is a perspective view of a third embodiment of the stand-alone expandable interbody spinal fusion device, in an unexpanded state.

FIG. 43 is a perspective view of stand-alone expandable interbody spinal fusion device 300 in an unexpanded state. Device 300 comprises superior component 302, inferior component 304, and expansion mechanisms 306, 308, 310, and 311, arranged to displace superior component 302 in a first direction D1 relative to inferior component 304 giving device 300 an expanded height $H_2$ greater than unexpanded height $H_1$, self-piercing screw mechanisms 312, 314, 316, and 318, arranged to engage the bone material of the surrounding vertebra (i.e., L3 and L4). Superior component 302 and inferior component 304 comprise at least one first aperture 320 arranged to allow fusion between bone fusing material and the adjacent vertebra, and a second aperture 392 located on the front face of device 300 and arranged to allow the introduction of bone fusing material into device 300. Second aperture 392 is illustrated as an arched slot as a non-limiting example, however, it should be appreciated that second aperture 392 could be any suitable aperture that would allow for the introduction of bone fusing material into device 300. Superior component 302 has a first surface 303 and inferior component 304 has a first surface 305. Embedded within the superior component, beneath surface 303, or above surface 303 (not depicted in FIG. 43), there is an anchor layer 307. Embedded within the inferior component, beneath surface 305, or above surface 305 (not depicted in FIG. 43), there is an anchor layer 309. Self-piercing screw mechanisms 312, 314, 316, and 318 can comprise the embodiment of either self-piercing screw mechanism 122 (as described supra) or self-piercing screw mechanism 146 (as described supra).

Figure 44:
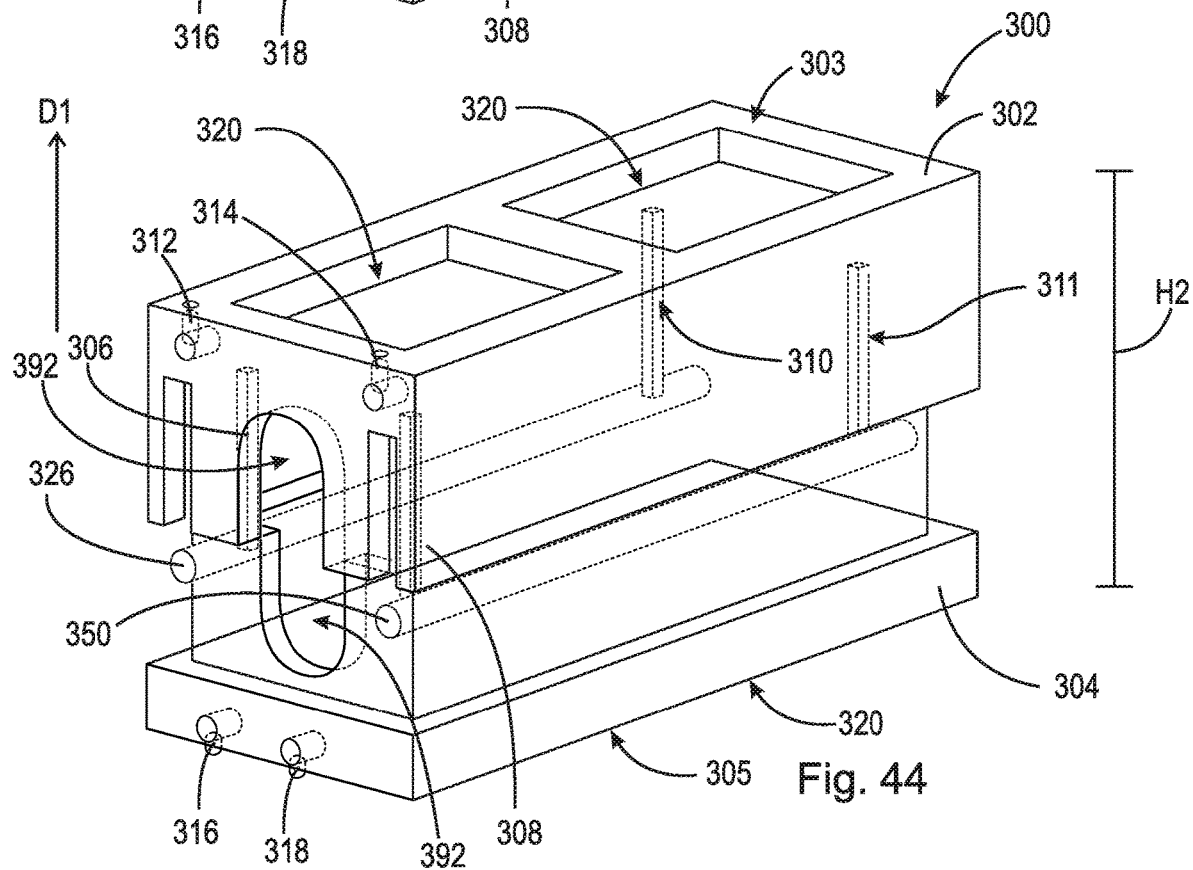
FIG. 44 is a perspective view of a third embodiment of the stand-alone expandable interbody spinal fusion device, in an expanded state.

FIG. 44 is a perspective view of stand-alone expandable interbody spinal fusion device 300, in an expanded state. Expansion mechanisms 306, 308, 310 and 311, are fully extended giving device 300 an expanded height $H_2$, greater than $H_1$. This embodiment of the implant differs from stand-alone expandable interbody spinal fusion device 200, as illustrated in FIGS. 41 and 42, in that expansion mechanisms 306, 308, 310, and 311, comprise the embodiment of expansion mechanism 178 illustrated in FIGS. 37-40. Additionally gear shaft 326 is arranged to engage expansion mechanisms 306 and 310, and gear shaft 350 is arranged to engage expansion mechanisms 308 and 311. Due to the gear shafts needing to start in a position closer to superior component 302, as illustrated in previous embodiments, cutouts are shown on the proximate surface of superior component 302, so that the gears of the expansion mechanisms can be accessed when device 300 is in an unexpanded state.

Figure 45:
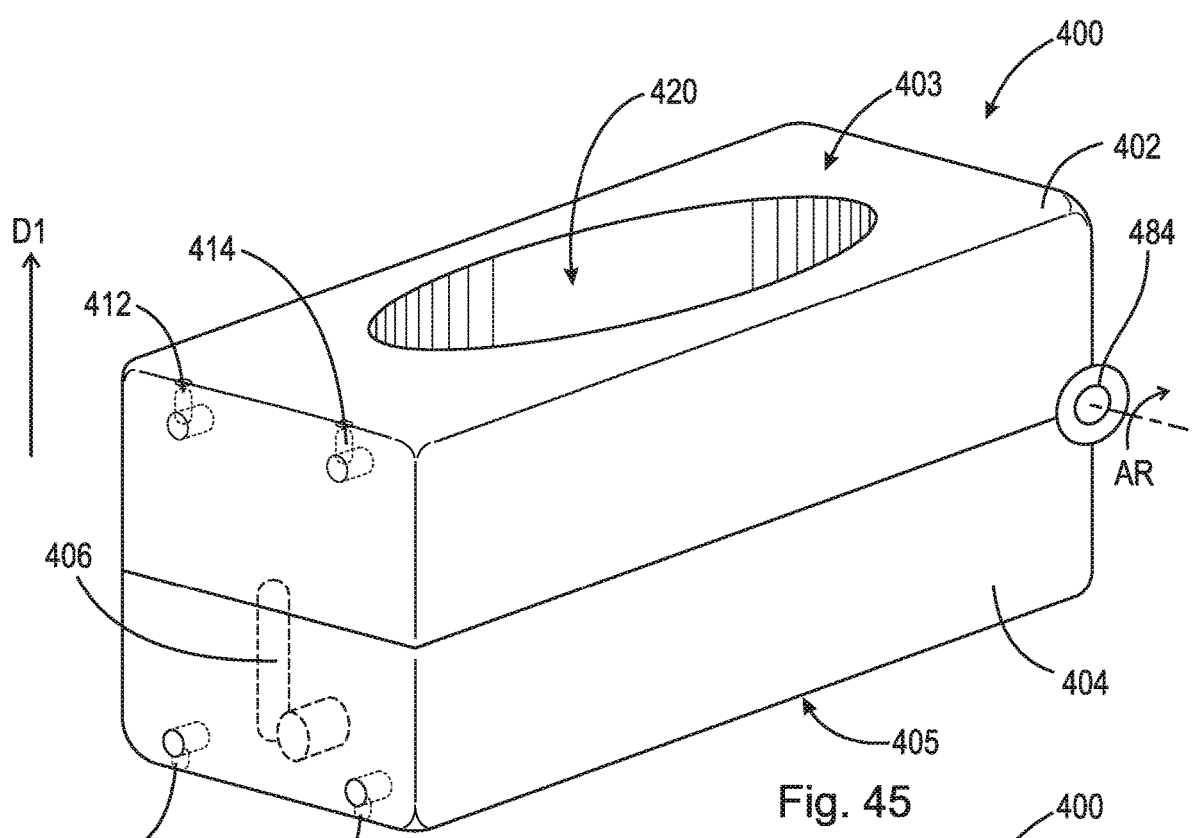
FIG. 45 is a perspective view of a fourth embodiment of the stand-alone expandable interbody spinal fusion device, in an unexpanded state.

FIG. 45 is a perspective view of stand-alone expandable interbody spinal fusion device 400 in an unexpanded state. Device 400 comprises superior component 402, inferior component 404, expansion mechanism 406 arranged to displace superior component 402 in a first direction D1 relative to inferior component 404, self-piercing screw mechanisms 412, 414, 416, and 418, arranged to engage the bone material of the surrounding vertebra (i.e., L3 and L4). Superior component 402 and inferior component 404 further comprise at least one first aperture 420 arranged to allow fusion between bone fusing material and the adjacent vertebra. Superior component 402 has a first surface 403 and inferior component 404 has a first surface 405. Embedded within the superior component, beneath surface 403, or above surface 403 (not depicted in FIG. 45), there is an anchor layer 407. Embedded within the inferior component, beneath surface 405, or above surface 405 (not depicted in FIG. 45), there is an anchor layer 409. Although not illustrated in FIG. 45, it should be appreciated that threaded inserts such as threaded inserts 813, 815, 817, and 819 described infra, can be used in place of anchor layers 407 and 409 to provide sufficient leverage for the screw mechanisms to pierce the bone material of adjacent vertebra. Self-piercing screw mechanisms 412, 414, 416, and 418 can comprise the embodiment of either self-piercing screw mechanism 122 (as described supra) or self-piercing screw mechanism 146 (as described supra). Device 400 further comprises hinge 484 fixedly secured to superior component 402 and inferior component 404 and arranged to rotatably displace the superior component about axis of rotation AR. Expansion mechanism 406 is preferably expansion mechanism 166 described supra.

Figure 46:
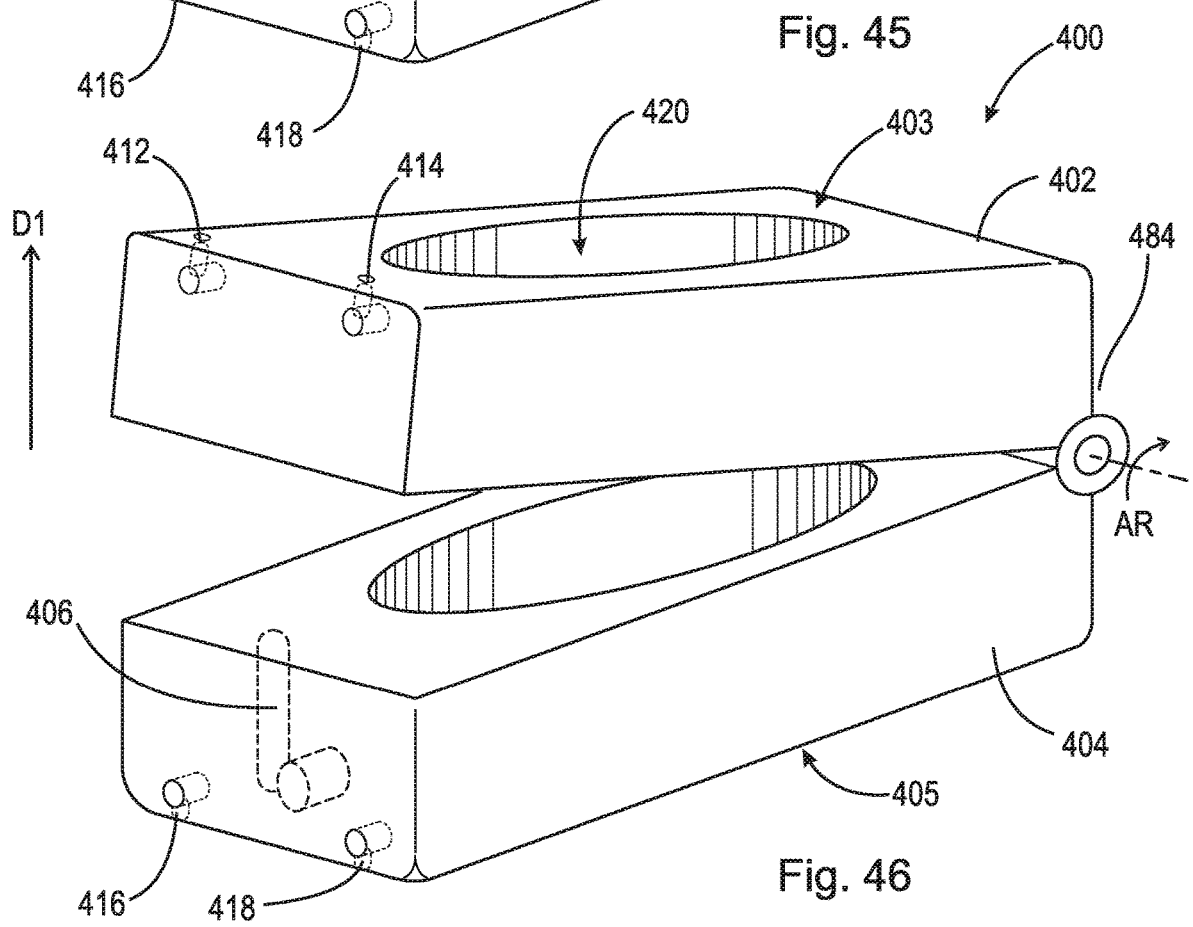
FIG. 46 is a perspective view of a fourth embodiment of the stand-alone expandable interbody spinal fusion device, in an expanded state.

FIG. 46 is a perspective view of stand-alone expandable interbody spinal fusion device 400 in an expanded state. As discussed above, expansion mechanism 406 is arranged to displace superior component in a first direction D1. In this embodiment expansion mechanism 406 is not partially embedded within superior component 402. Instead, expansion mechanism 406 is illustrated with a rounded tip, such that during expansion the rounded tip can slide along the inner surface of the superior component. This allows expansion mechanism 406 to fully expand in direction D1 without binding due to the angular displacement of superior component 402.

Figure 47:
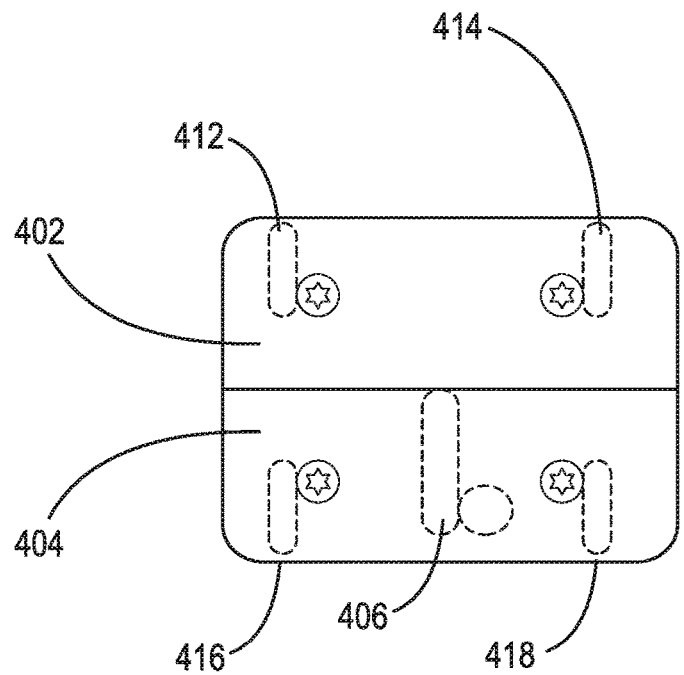
FIG. 47 is a front view of a fourth embodiment of the stand-alone expandable interbody spinal fusion device, in an unexpanded state.
Figure 48:
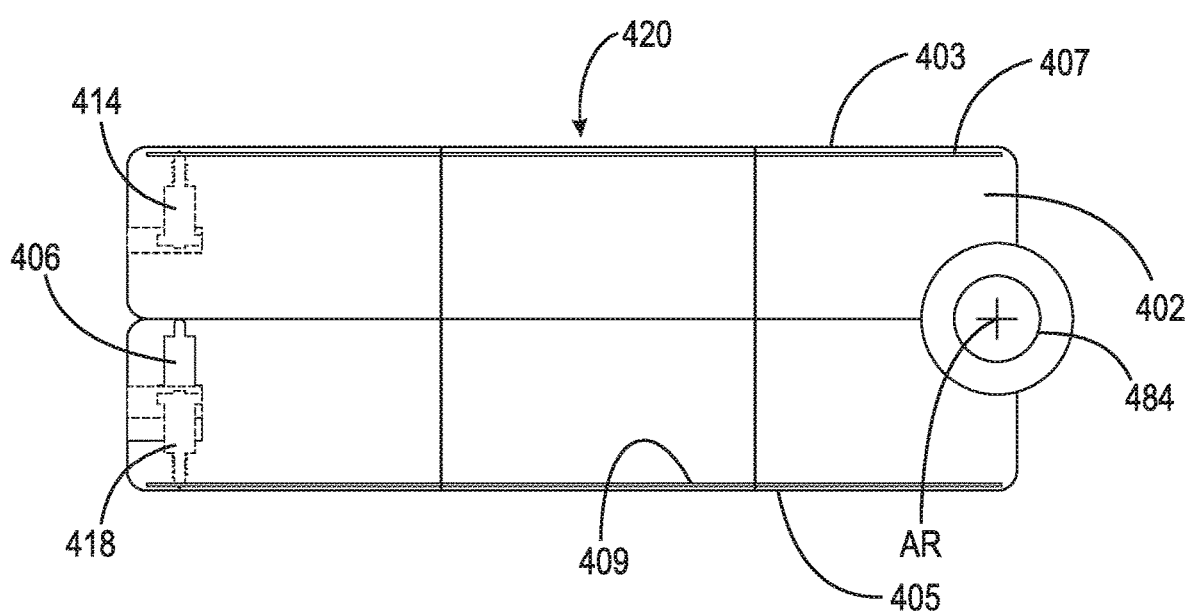
FIG. 48 is a side view of a fourth embodiment of the stand-alone expandable interbody spinal fusion device, in an unexpanded state.
Figure 49:
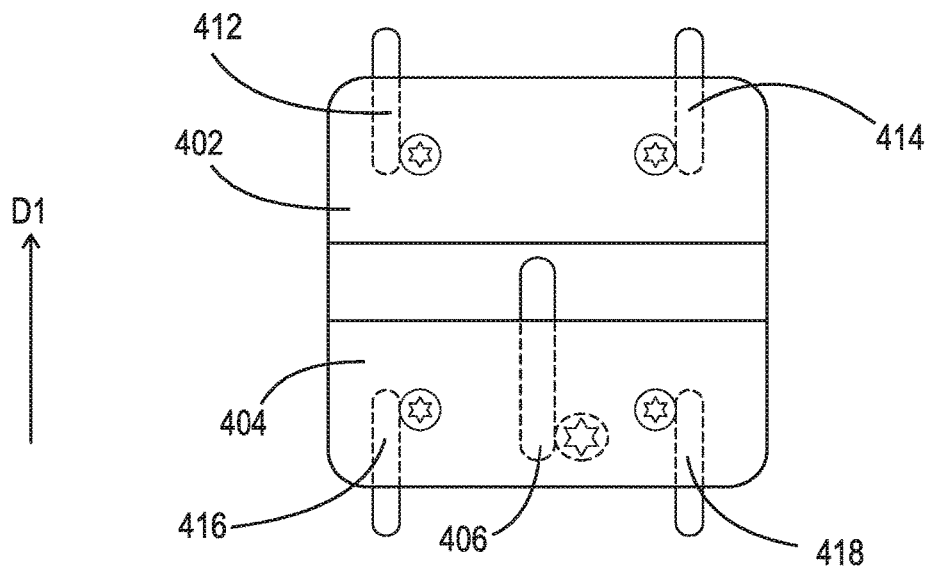
FIG. 49 is a front view of a fourth embodiment of the stand-alone expandable interbody spinal fusion device, in an expanded state.
Figure 50:
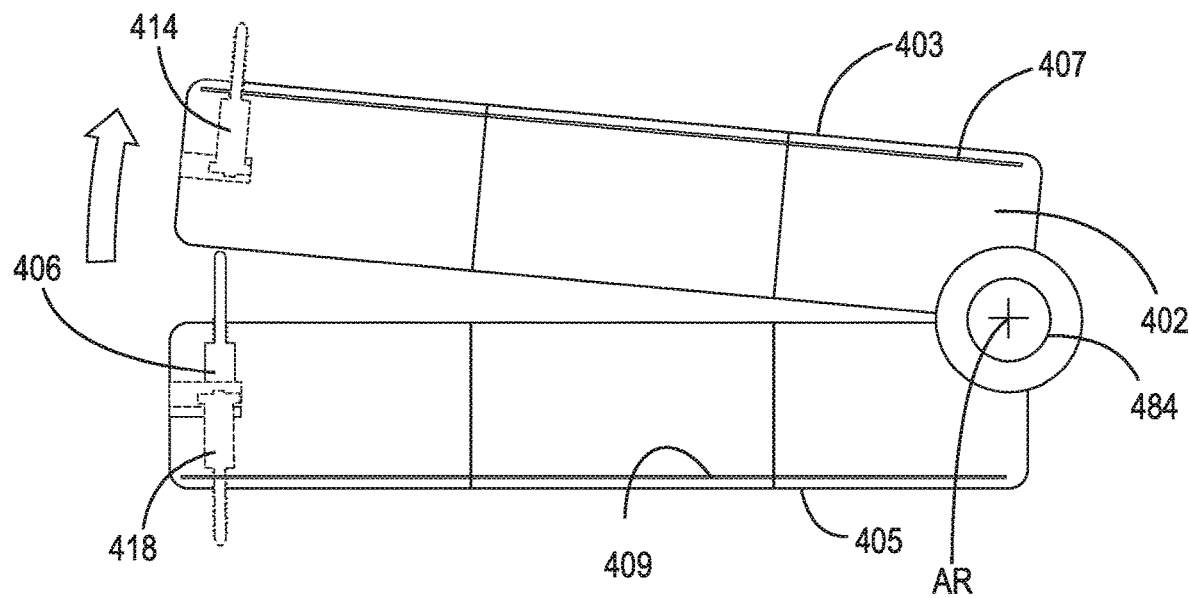
FIG. 50 is a side view of a fourth embodiment of the stand-alone expandable interbody spinal fusion device, in an expanded state.

FIG. 47 is a front view stand-alone expandable interbody spinal fusion device 400, in an unexpanded state. FIG. 48 is a side view of stand-alone expandable interbody spinal fusion device 400, in an unexpanded state. FIG. 49 is a front view stand-alone expandable interbody spinal fusion device 400, in an expanded state. FIG. 50 is a side view of stand-alone expandable interbody spinal fusion device 400, in an expanded state.

Figure 51:
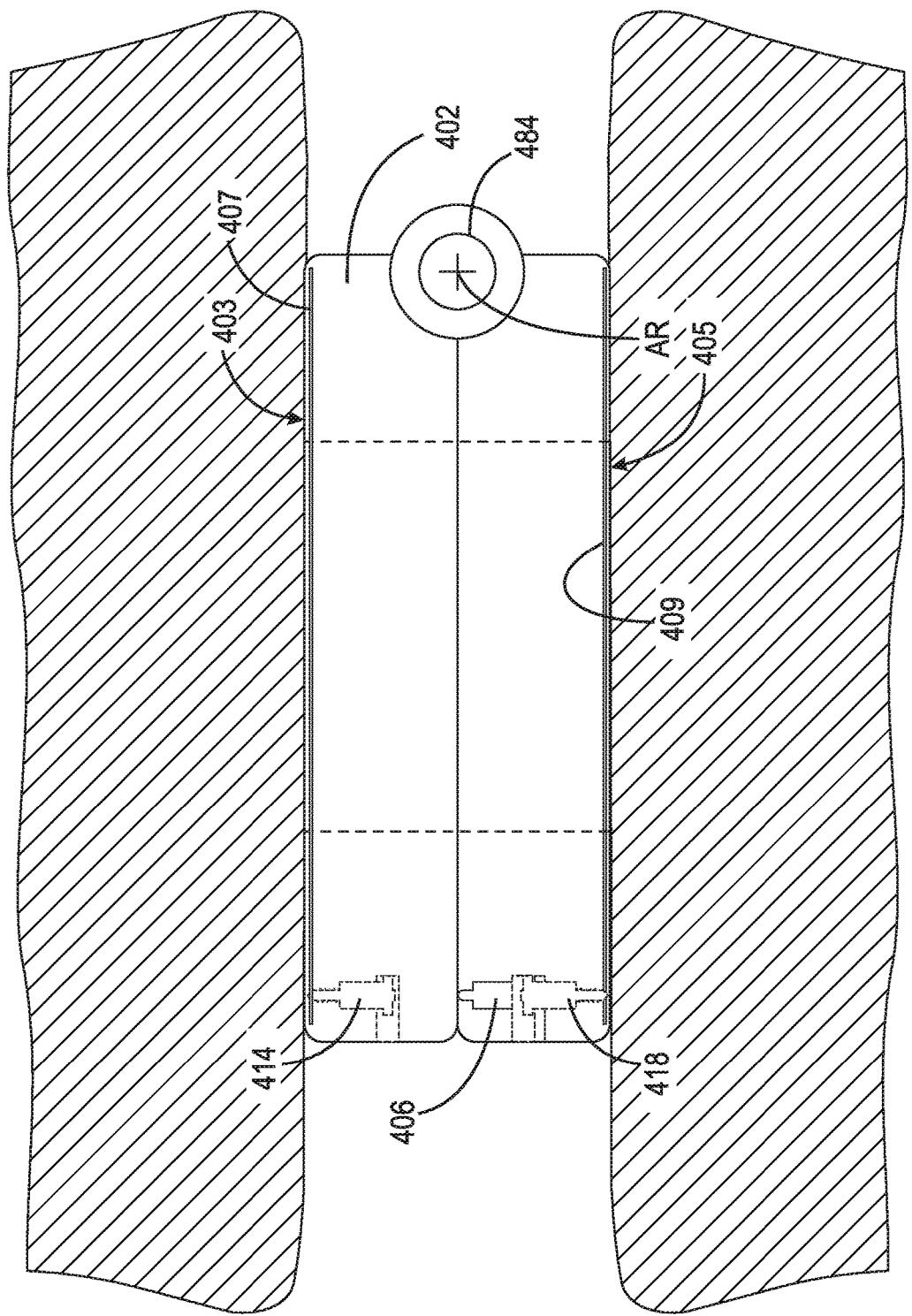
FIG. 51 is a partial cross-sectional view of a fourth embodiment of the stand-alone expandable interbody spinal fusion device, in an unexpanded state.

FIG. 51 is a partial cross-sectional view of stand-alone expandable interbody spinal fusion device 400, in an unexpanded state. The self-piercing screw mechanisms 412, 414, 416, and 418, are engaged first to secure device 400 from shifting in disc space 12. Once self-piercing screw mechanisms 412, 414, 416, and 418 are engaged. Expansion mechanism 406 is utilized to displace superior component 402 in direction D1 and expand device 400.

Figure 52:
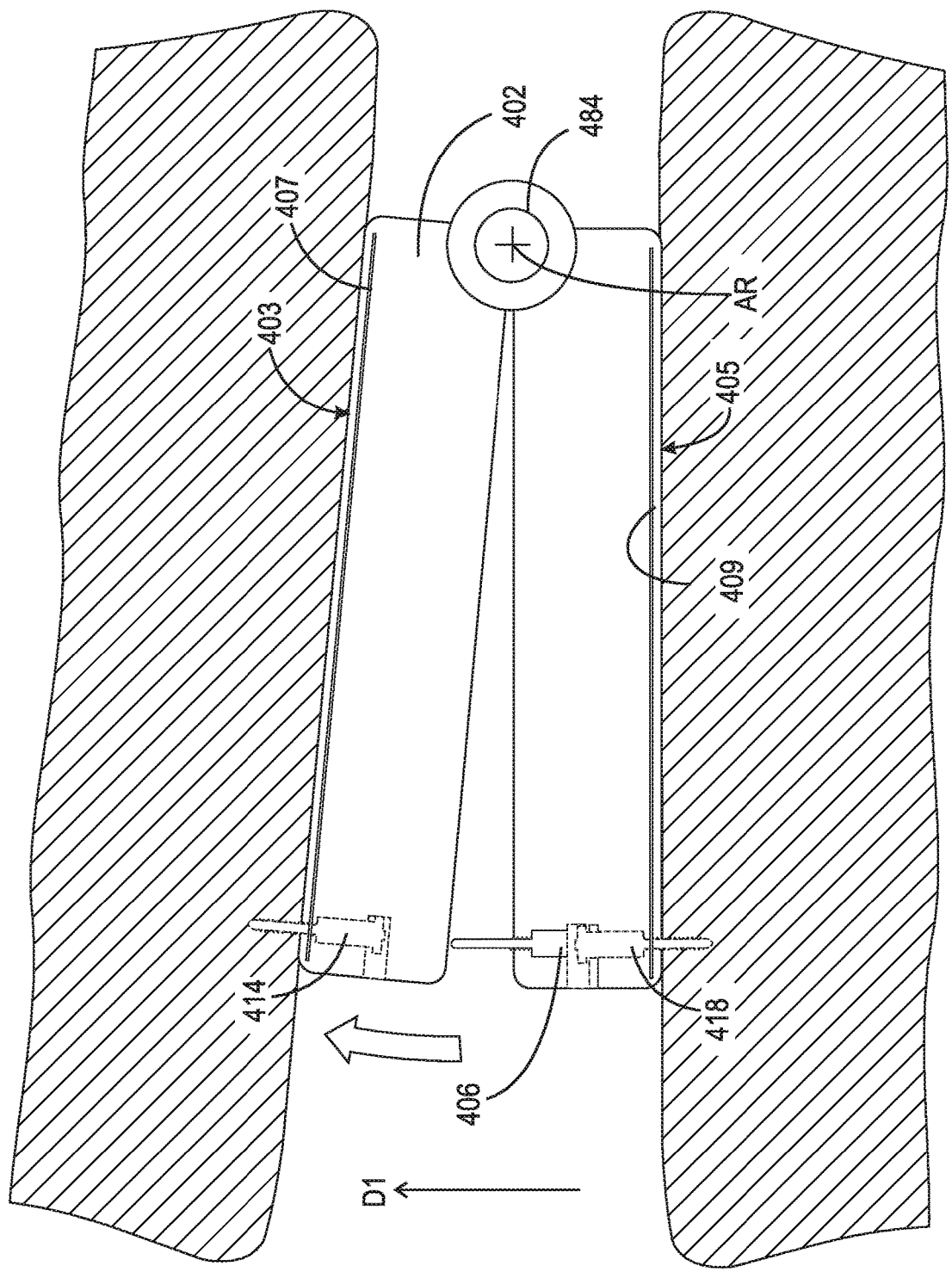
FIG. 52 is a partial cross-sectional view of a fourth embodiment of the stand-alone expandable interbody spinal fusion device, in an expanded state.
Figure 53:
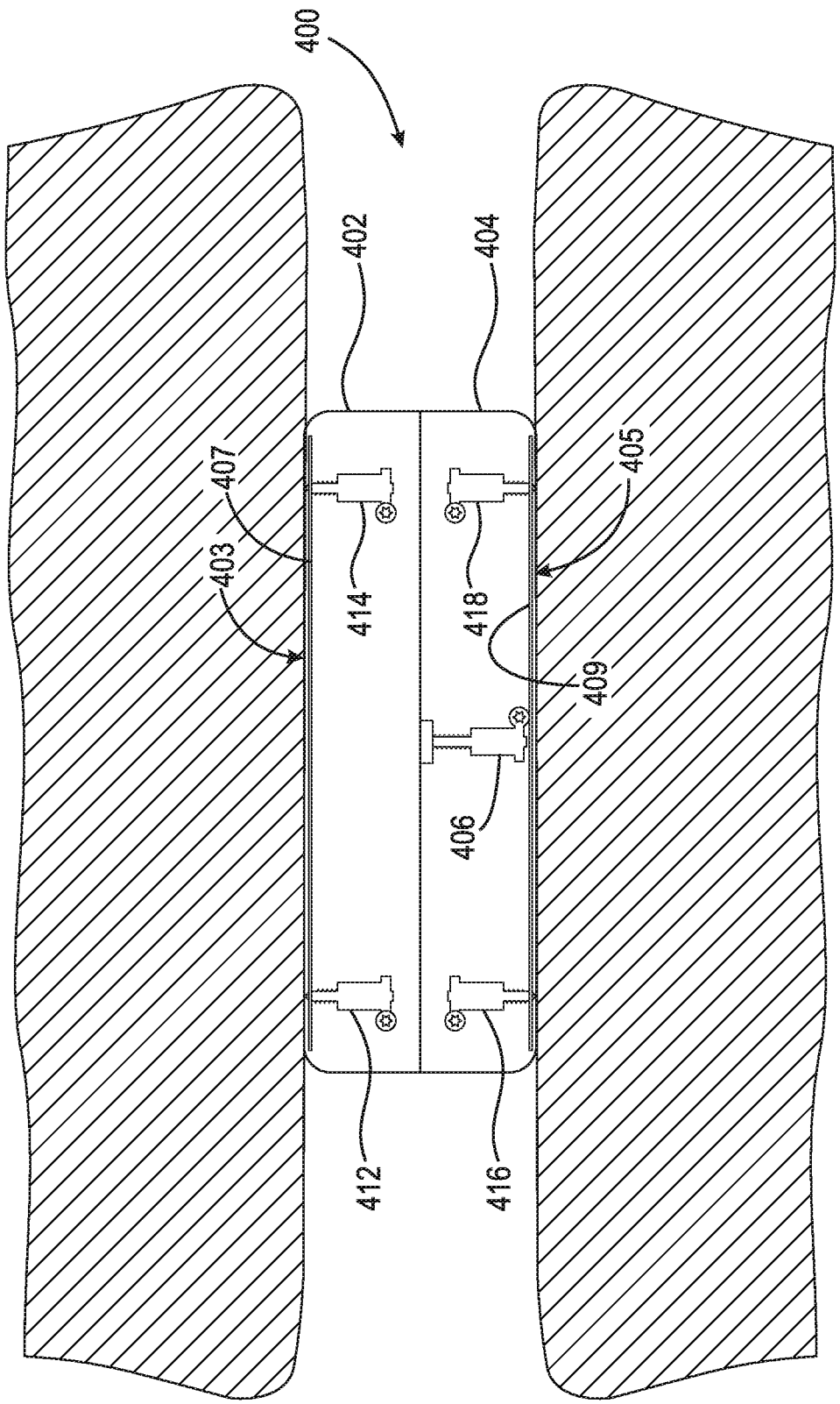
FIG. 53 is a partial cross-sectional front view of a fourth embodiment of the stand-alone expandable interbody spinal fusion device, in an unexpanded state.
Figure 54:
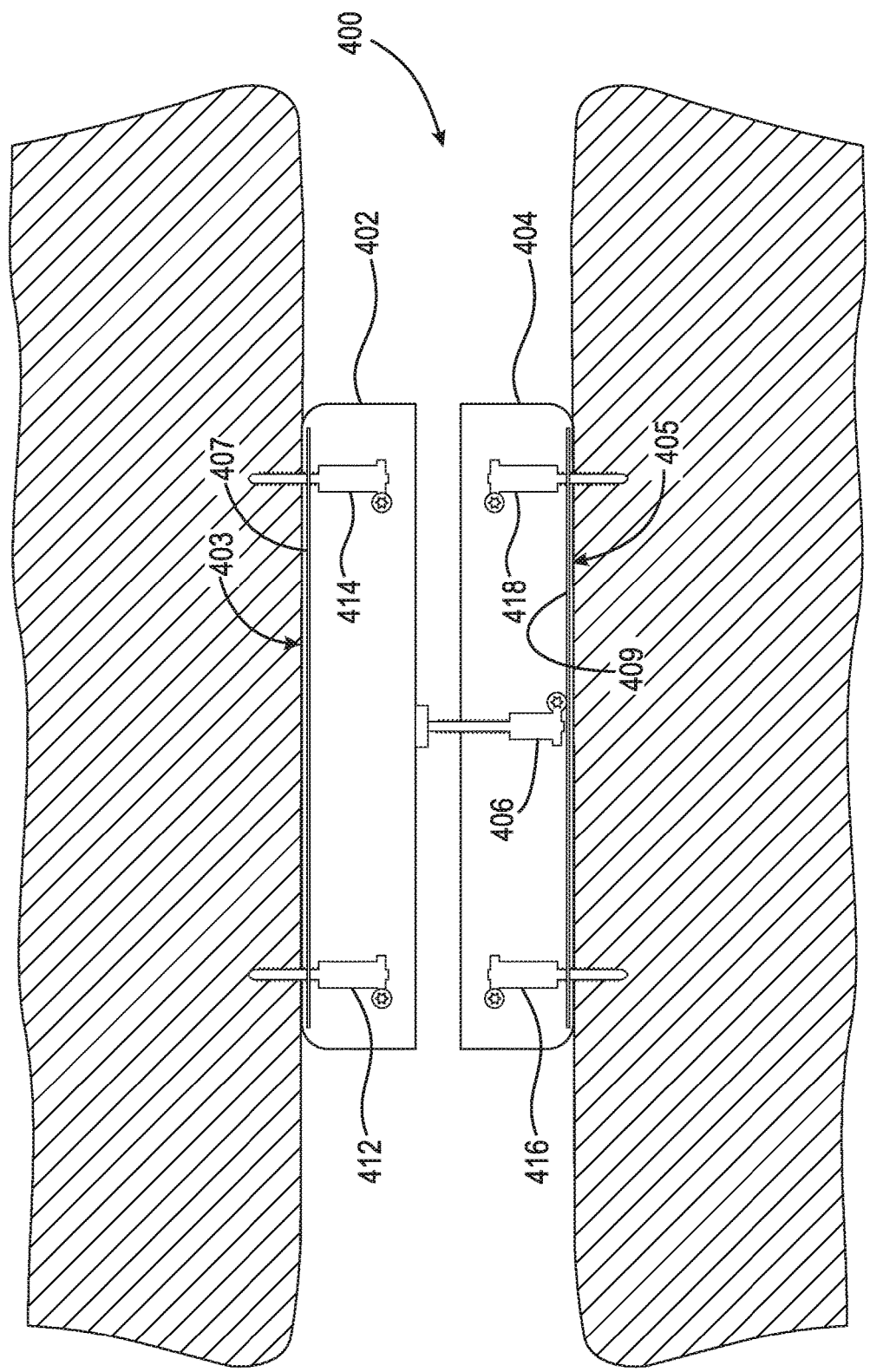
FIG. 54 is a partial cross-sectional front view of a fourth embodiment of the stand-alone expandable interbody spinal fusion device, in an expanded state.

FIG. 52 is a partial cross-sectional view of stand-alone expandable interbody spinal fusion device 400, in an expanded state. FIG. 53 is a partial cross-sectional front view stand-alone expandable interbody spinal fusion device 400, in an unexpanded state. FIG. 54 is a partial cross-sectional front view of stand-alone expandable interbody spinal fusion device 400, in an expanded state.

Figure 55:
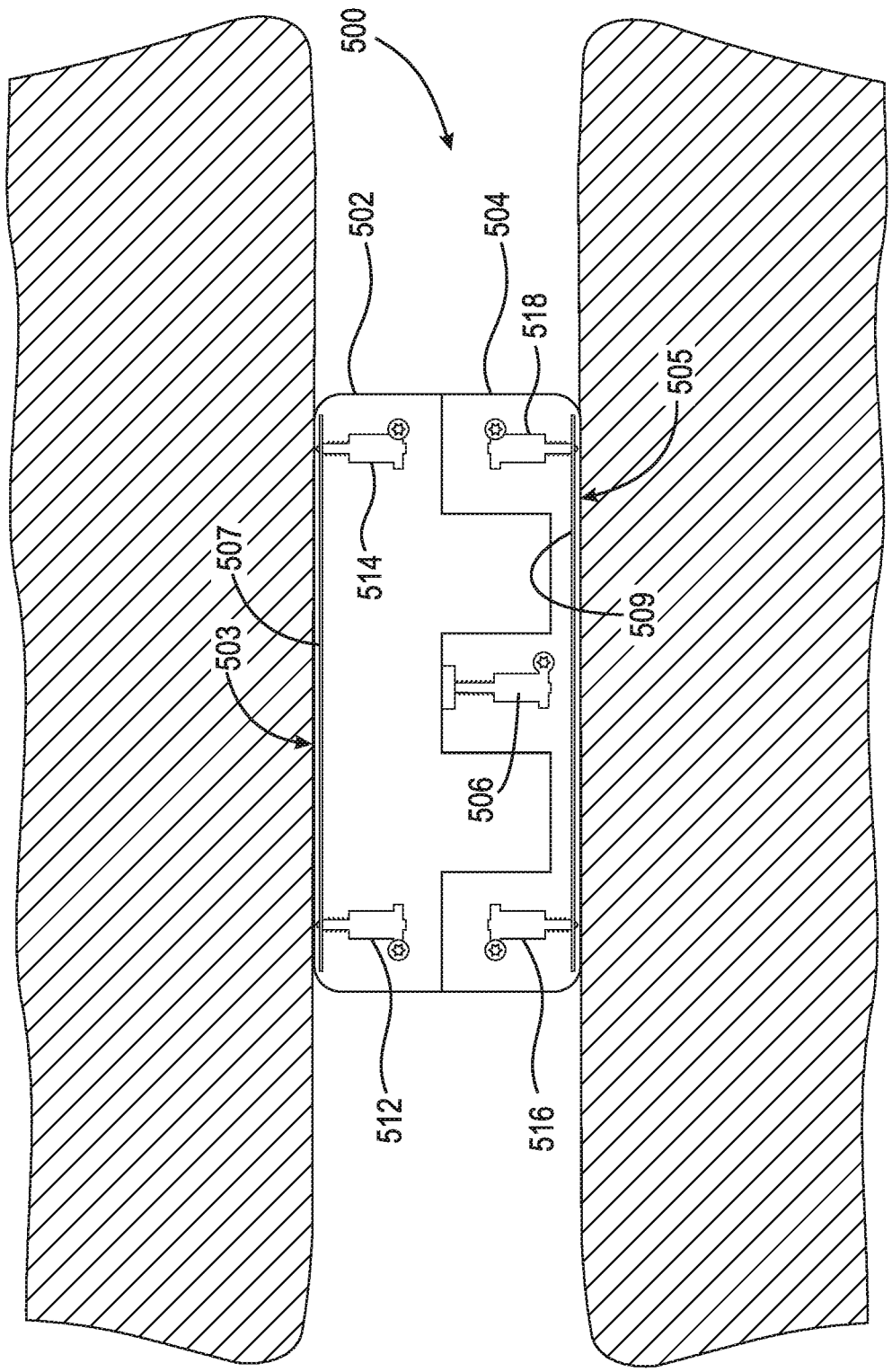
FIG. 55 is a partial cross-sectional front view of a fifth embodiment of the stand-alone expandable interbody spinal fusion device, in an unexpanded state.
Figure 56:
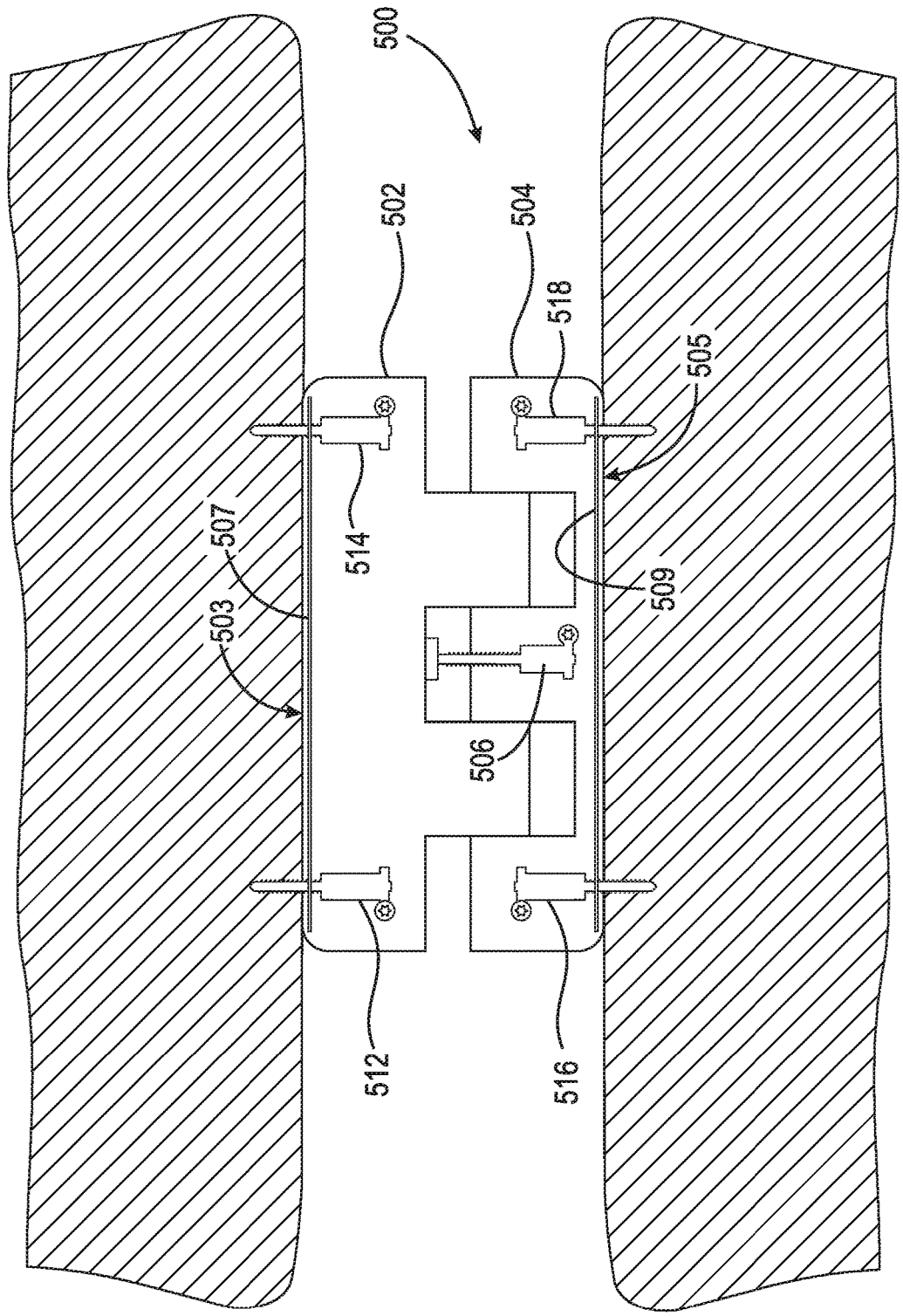
FIG. 56 is a partial cross-sectional front view of a fifth embodiment of the stand-alone expandable interbody spinal fusion device, in an expanded state.

FIG. 55 is a partial cross-sectional front view of stand-alone expandable interbody spinal fusion device 500, in an unexpanded state. Device 500 is comprised of the same elements as device 400. Device 500 comprises superior component 502 and inferior component 504, and expansion mechanism 506. Superior component 502 and inferior component 504 further comprise at least one first aperture 520 (not shown in FIG. 55) arranged to allow fusion between bone fusing material and the adjacent vertebra. Device 500 further comprises self-piercing screw mechanisms 512, 514, 516, and 518. Superior component 502 has a first surface 503 and inferior component 504 has a first surface 505. Embedded within the superior component, beneath surface 503, or above surface 503 (not depicted in FIG. 55), there is an anchor layer 507. Embedded within the inferior component, beneath surface 505, or above surface 505 (not depicted in FIG. 55), there is an anchor layer 509. Although not illustrated in FIG. 55, it should be appreciated that threaded inserts such as threaded inserts 813, 815, 817, and 819 described infra, can be used in place of anchor layers 507 and 509 to provide sufficient leverage for the screw mechanisms to pierce the bone material of adjacent vertebra. Self-piercing screw mechanisms 512, 514, 516, and 518 can comprise the embodiment of either self-piercing screw mechanism 122 (as described supra) or self-piercing screw mechanism 146 (as described supra). Device 500 further comprises hinge 584 (not shown in FIG. 55) fixedly secured to superior component 502 and inferior component 504 and arranged to rotatably displace the superior component about axis of rotation AR. Device 500 differs from device 400 in that the superior component 502 and inferior component 504 each have a have a sinusoidal cross-section, inversely arranged with respect to each other such that in the unexpanded state, superior component 502 and inferior component 504 slidingly engage each other. FIG. 56 is a partial cross-sectional front view of stand-alone expandable interbody spinal fusion device 500, in an expanded state.

Figure 57:
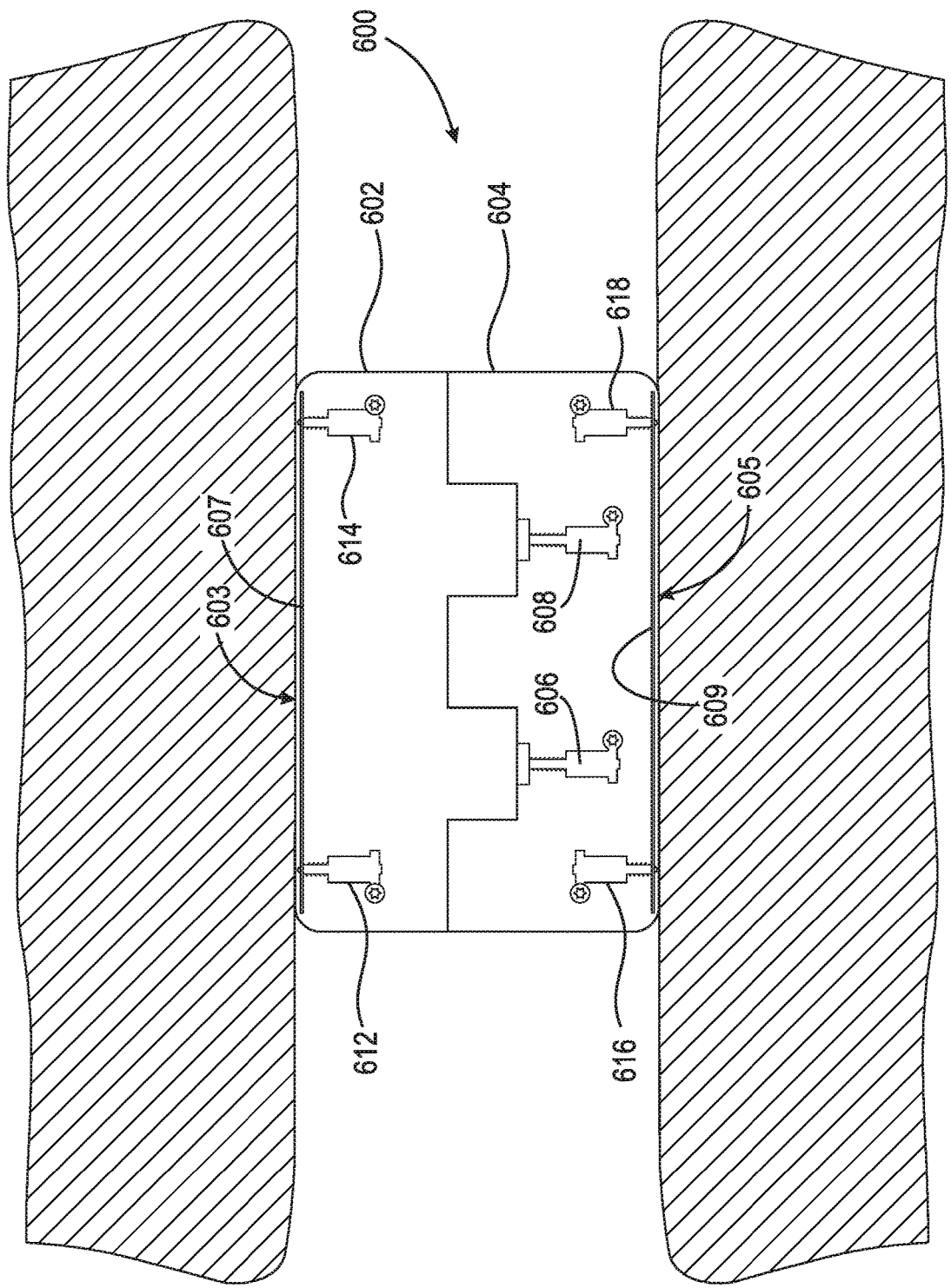
FIG. 57 is a partial cross-sectional front view of a sixth embodiment of the stand-alone expandable interbody spinal fusion device, in an unexpanded state.
Figure 58:
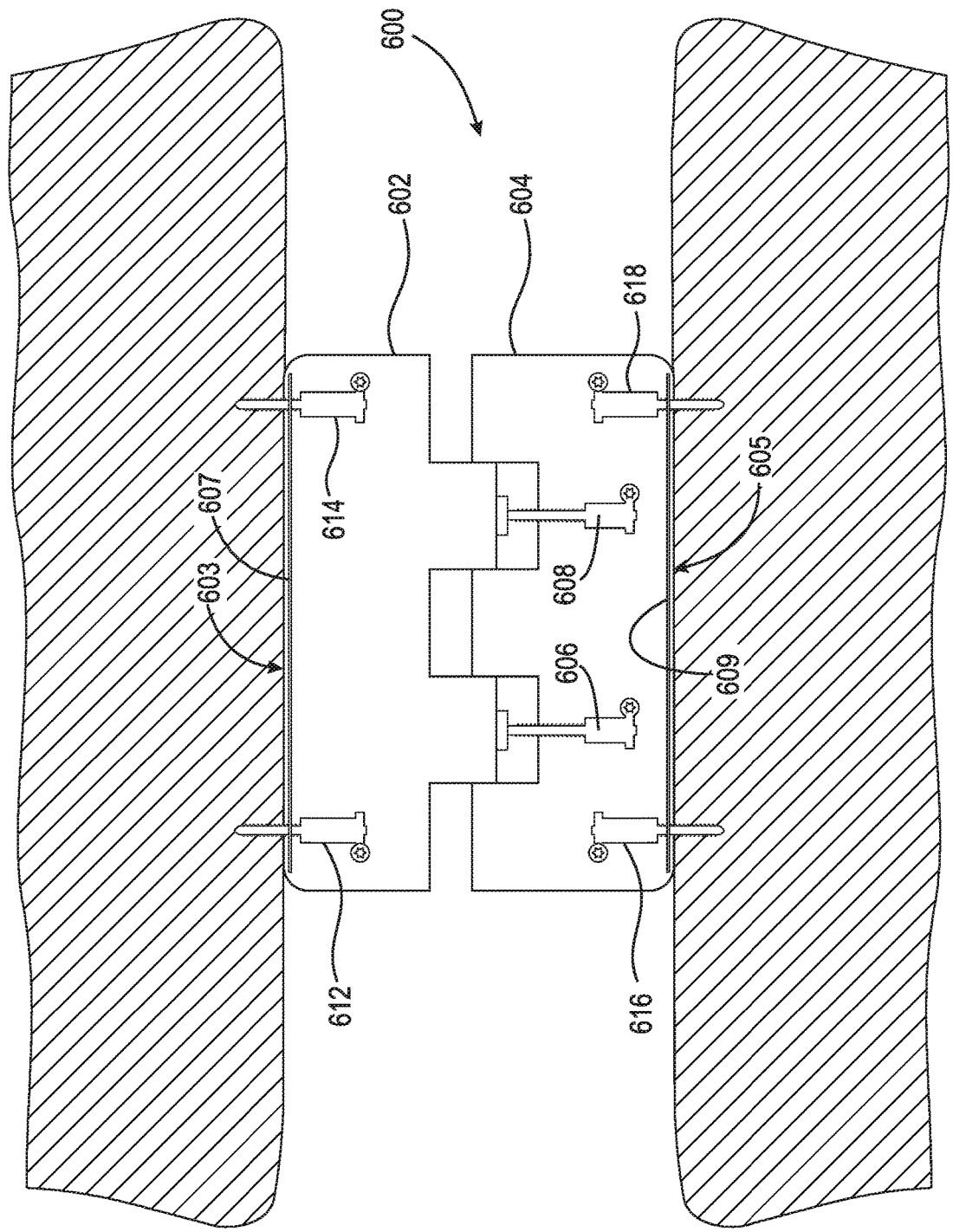
FIG. 58 is a partial cross-sectional front view of a sixth embodiment of the stand-alone expandable interbody spinal fusion device, in an expanded state.

FIG. 57 is a partial cross-sectional front view of stand-alone expandable interbody spinal fusion device 600, in an unexpanded state. Device 600 differs from device 500 as illustrated in FIGS. 55 and 56, in that it has two distinct expansion mechanisms 606, and 608, arranged to displace superior component 602 in direction D1 relative to inferior component 604. Superior component 602 and inferior component 604 further comprise at least one first aperture 620 (not shown in FIG. 57) arranged to allow fusion between bone fusing material and the adjacent vertebra. Device 600 further comprises self-piercing screw mechanisms 612, 614, 616, and 618. Superior component 602 has a first surface 603 and inferior component 604 has a first surface 605. Embedded within the superior component, beneath surface 603, or above surface 603 (not depicted in FIG. 57), there is an anchor layer 607. Embedded within the inferior component, beneath surface 605, or above surface 605 (not depicted in FIG. 57), there is an anchor layer 609. Although not illustrated in FIG. 57 it should be appreciated that threaded inserts such as threaded inserts 813, 815, 817, and 819 described infra, can be used in place of anchor layers 607 and 609 to provide sufficient leverage for the screw mechanisms to pierce the bone material of adjacent vertebra. Self-piercing screw mechanisms 612, 614, 616, and 618 can comprise the embodiment of either self-piercing screw mechanism 122 (as described supra) or self-piercing screw mechanism 146 (as described supra). FIG. 58 is a partial cross-sectional front view of stand-alone expandable interbody spinal fusion device 600, in an expanded state.

Figure 60:
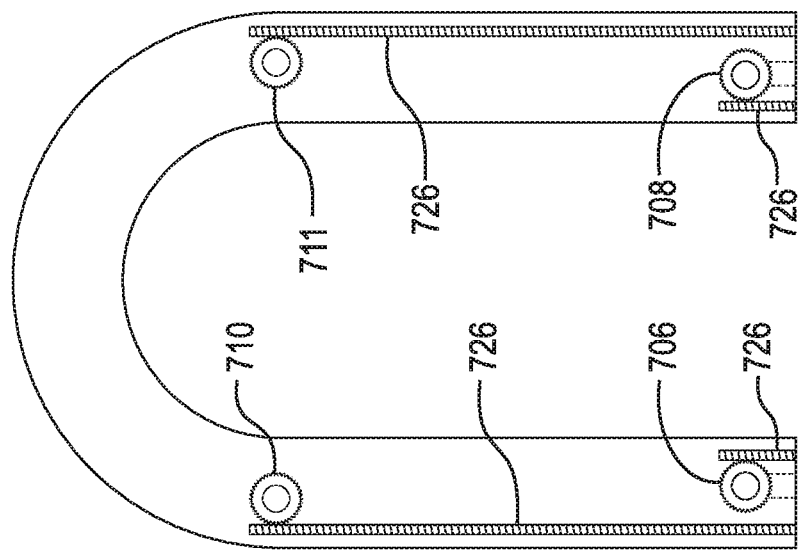
FIG. 60 is a cross-sectional view of a seventh embodiment of the stand-alone expandable interbody spinal fusion device, in an expanded state taken along line 60-60 in FIG. 59.
Figure 59:
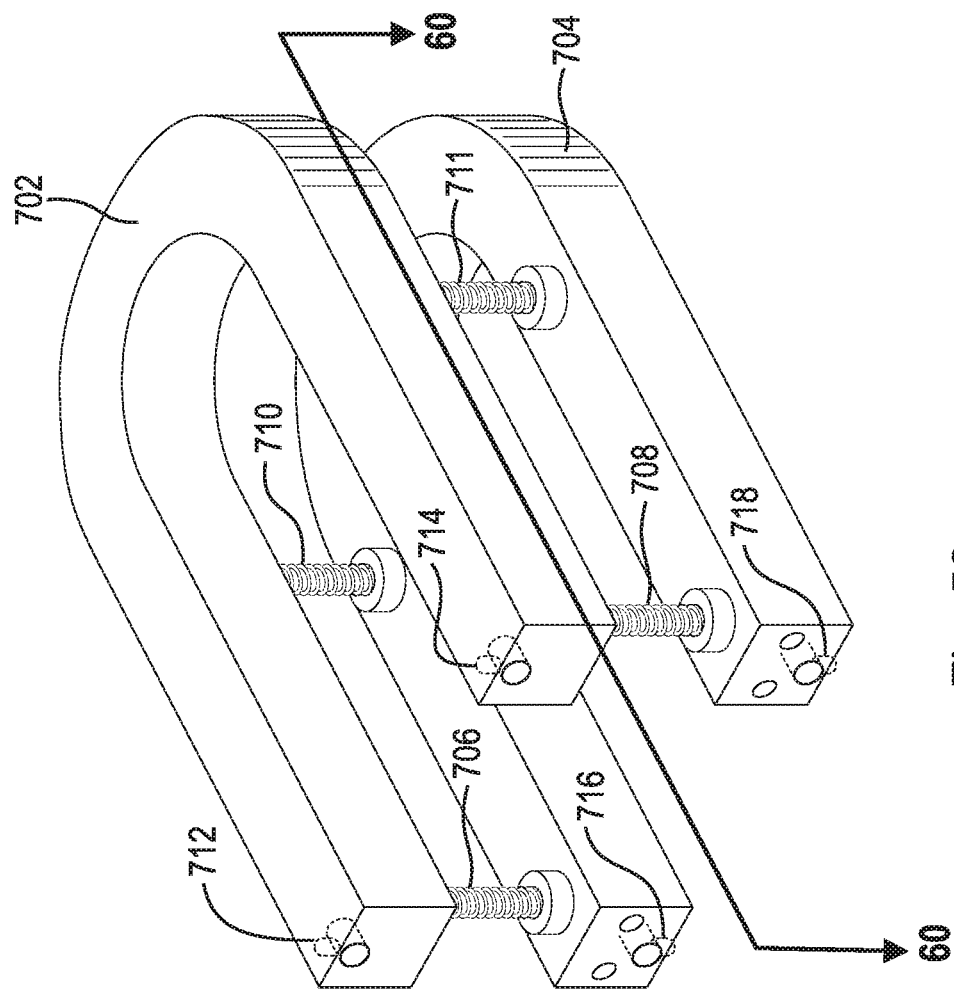
FIG. 59 is a perspective view of a seventh embodiment of the stand-alone expandable interbody spinal fusion device, in an expanded state.

FIG. 59 is a perspective view of a stand-alone expandable interbody spinal fusion device 700, in an expanded state. Device 700 comprises expansion mechanisms 706, 708, 710 and 711 each having a worm 726 and arranged to displace superior component 702 in direction D1 relative to inferior component 704. Device 700 differs from previous embodiments in that the superior component 702 and inferior component 704 are formed in the shape of a horseshoe. Device 700 further comprises self-piercing screw mechanisms 712, 714, 716, and 718. Superior component 702 has a first surface 703 and inferior component 704 has a first surface 705. Embedded within the superior component, beneath surface 703, or above surface 704 (not depicted in FIG. 59), there is an anchor layer 707 (not shown in FIG. 59). Embedded within the inferior component, beneath surface 705, or above surface 705 (not depicted in FIG. 59), there is an anchor layer 709 (not shown in FIG. 59). Although not illustrated in FIG. 59, it should be appreciated that threaded inserts such as threaded inserts 813, 815, 817, and 819 described infra, can be used in place of anchor layers 707 and 709 to provide sufficient leverage for the screw mechanisms to pierce the bone material of adjacent vertebra. Self-piercing screw mechanisms 712, 714, 716, and 718 can comprise the embodiment of either self-piercing screw mechanism 122 (as described supra) or self-piercing screw mechanism 146 (as described supra). FIG. 60 is a cross-sectional view of stand-alone expandable interbody spinal fusion device 700, in an expanded state taken along line 60-60 in FIG. 59.

Figure 61:
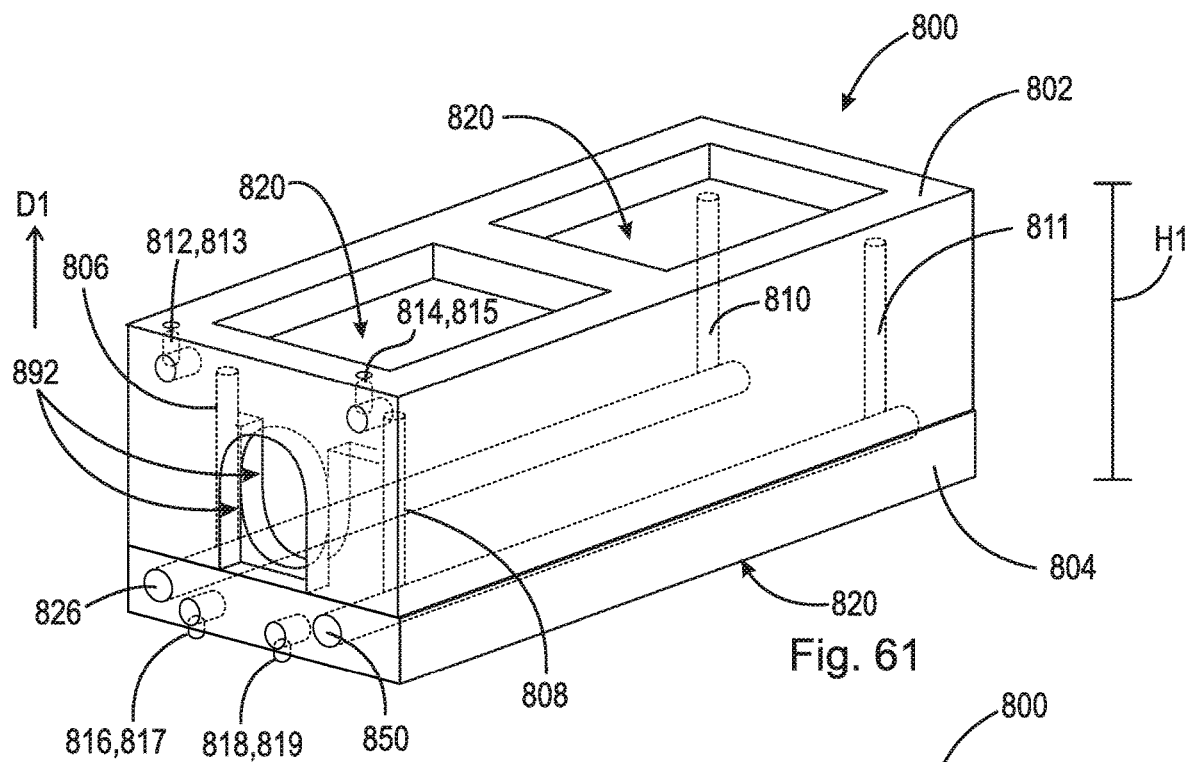
FIG. 61 is a perspective view of an eighth embodiment of the stand-alone expandable interbody spinal fusion device, in an unexpanded state.

FIG. 61 is a perspective view of stand-alone expandable interbody spinal fusion device 800 in an unexpanded state. Device 800 comprises superior component 802, inferior component 804, expansion mechanisms 806, 808, 810, and 811, arranged to displace superior component 802 in a first direction D1 relative to inferior component 804 giving device 800 an expanded height $H_2$ greater than unexpanded height $H_1$, self-piercing screw mechanisms 812, 814, 816, and 818, arranged to engage the bone material of the surrounding vertebra (i.e., L3 and L4). Superior component 802 has a first surface 803 and inferior component 804 has a first surface 805 (shown n FIGS. 64 and 66). Superior component 802 and inferior component 804 further comprise at least one first aperture 820 arranged to allow fusion between bone fusing material and the adjacent vertebra, and a second aperture 892 located on the front face of device 800 and arranged to allow the introduction of bone fusing material into device 800. Second aperture 892 is illustrated as an arched slot as a non-limiting example, however, it should be appreciated that second aperture 892 could be any suitable aperture that would allow for the introduction of bone fusing material into device 800. Superior component 802 further comprises threaded inserts 813, 815, 817, and 819. Threaded inserts 813, and 815 are fixedly secured within superior component 802, and threaded inserts 817 and 819 are fixedly secured within inferior component 804. Self-piercing screw mechanisms 812, 814, 816, and 818 engage with the threads of the threaded inserts giving the self-piercing screw bodies the needed leverage to engage with the bone material of the adjacent vertebra. Threaded inserts 813, 815, 817, and 819 can be made of titanium or other suitable material that is more dense than the metal used in the threading of the self-piercing screws. Self-piercing screw mechanisms 812, 814, 816, and 818 can comprise the embodiment of either self-piercing screw mechanism 122 (as described supra) or self-piercing screw mechanism 146 (as described supra).

Figure 62:
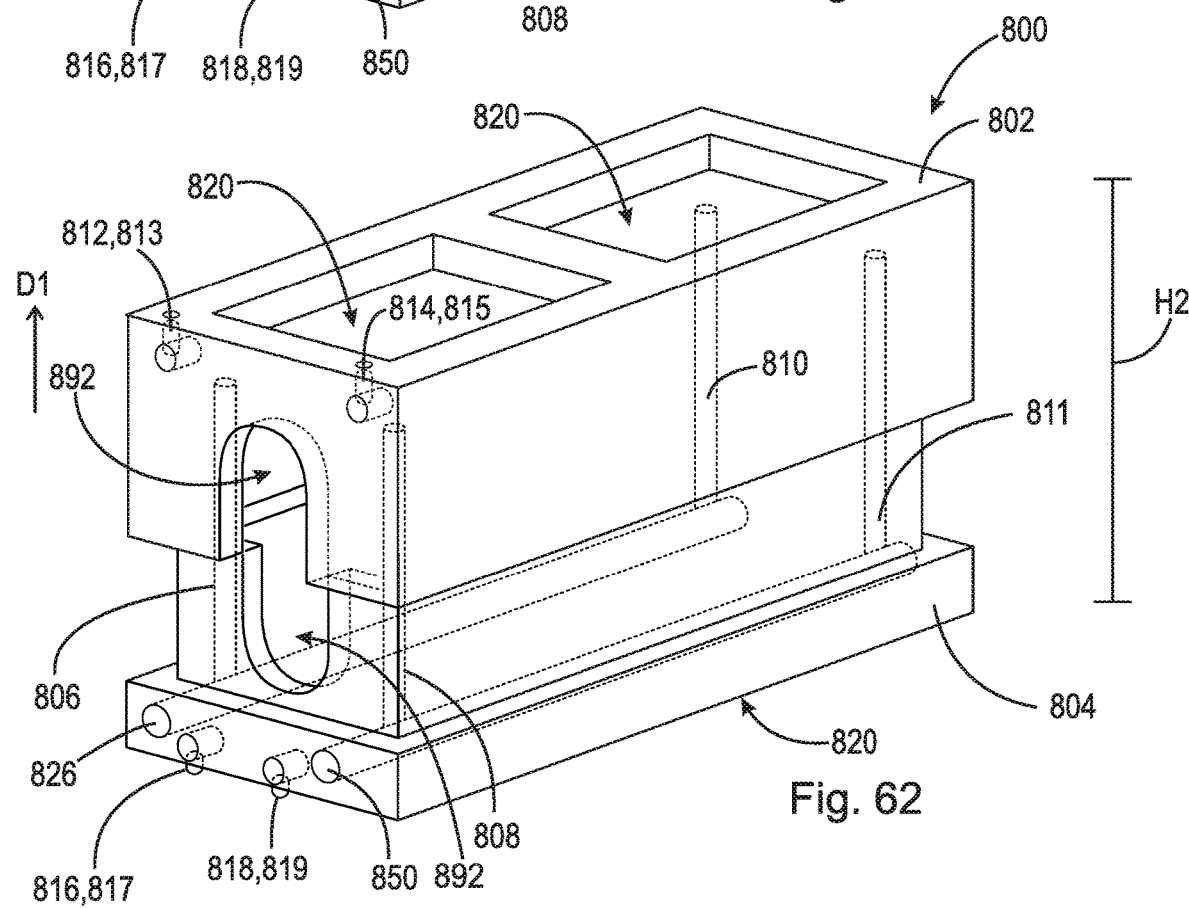
FIG. 62 is a perspective view of an eighth embodiment of the stand-alone expandable interbody spinal fusion device, in an expanded state.

FIG. 62 is a perspective view of stand-alone expandable interbody spinal fusion device 800, in an expanded state. During surgery and after device 800 is implanted into disc space 12, a surgeon can apply torque to expansion mechanisms expansion mechanisms 806, 808, 810 and 811 via any device that imparts rotational force (e.g., a screw driver or impact driver). The rotational force causes expansion mechanisms 806, 808, 810 and 811 to displace superior component 802 in direction D1 relative to inferior component 804 giving device 200 an expanded height $H_2$ greater than $H_1$. This embodiment of the implant differs from stand-alone expandable interbody spinal fusion device 200, as illustrated in FIGS. 41 and 42, in that instead of anchor layers 207 and 209, each screw mechanism threads itself through threaded inserts 813, 815, 817, and 819. Although not shown in FIG. 61 or 62 it is possible to vary the thread ratio of each expansion mechanism allowing for an uneven expansion of superior component 802.

Figures 63, 64:
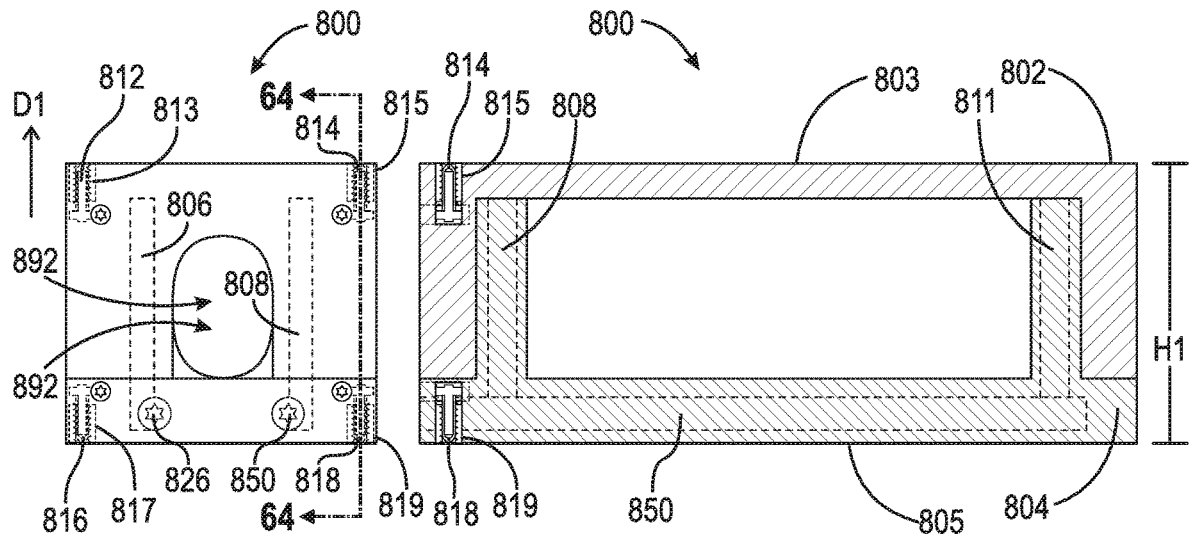
FIG. 63 is a front view of an eighth embodiment of the stand-alone expandable interbody spinal fusion device, in an unexpanded state.
FIG. 64 is a cross-sectional view of an eighth embodiment of the stand-alone expandable interbody spinal fusion device, in an unexpanded state taken generally along line 64-64 in FIG. 63.

FIG. 63 is a front view of stand-alone expandable interbody spinal fusion device 800, in an unexpanded state having an unexpanded height $H_1$. FIG. 64 is a side view stand-alone expandable interbody spinal fusion device 800, in an unexpanded state having an unexpanded height $H_1$. FIG. 64 illustrates the cross section along line 64-64 in FIG. 63. FIG. 64 shows the cross section through self-piercing screw mechanism 814 fixedly secured within superior component 802, and self-piercing screw mechanism 818 fixedly secured within inferior component 804. Further, FIG. 64 illustrates the cross section of threaded inserts 815 operatively arranged to engage self-piercing screw mechanism 814, and threaded insert 819 operatively arranged to engage self-piercing screw mechanism 818.

Figures 65, 66:
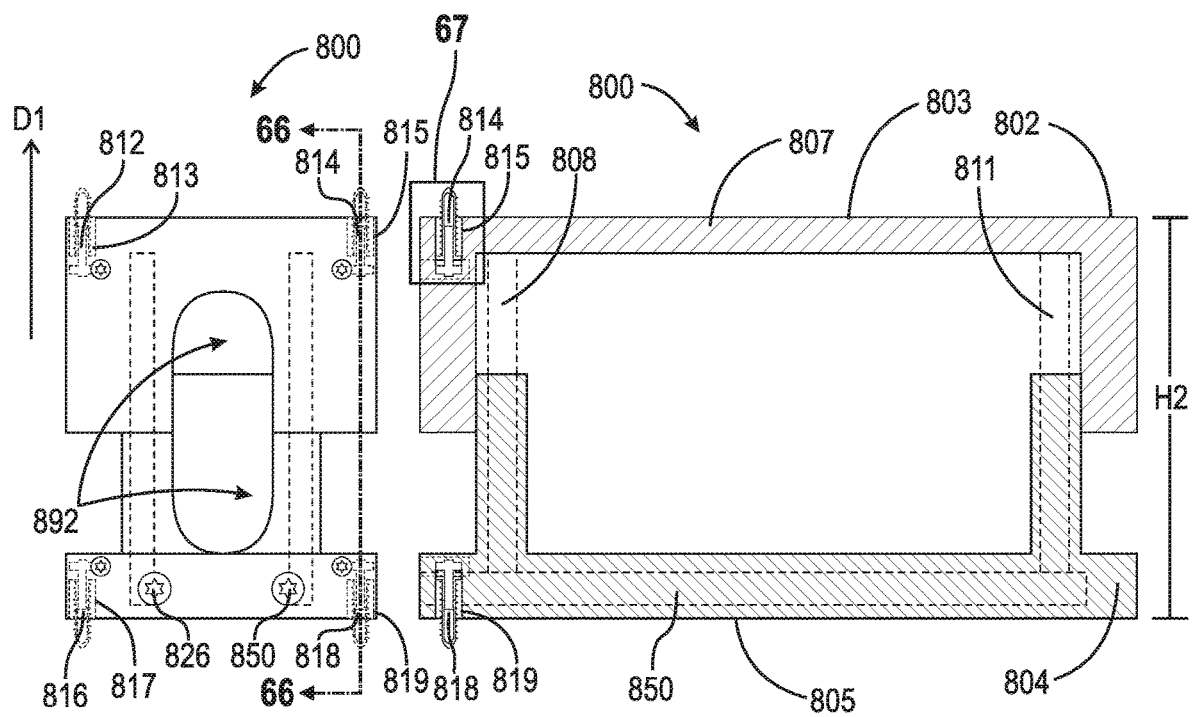
FIG. 65 is a front view of an eighth embodiment of the stand-alone expandable interbody spinal fusion device, in an expanded state.
FIG. 66 is a cross-sectional view of an eighth embodiment of the stand-alone expandable interbody spinal fusion device, in an expanded state taken generally alone line 66-66 in FIG. 65.

FIG. 65 is a front view stand-alone expandable interbody spinal fusion device 800, in an expanded state having an expanded height $H_2$, greater than $H_1$. FIG. 66 is a front view stand-alone expandable interbody spinal fusion device 800, in an expanded state having an expanded height $H_2$, greater than $H_1$. As torque is transferred through self-piercing screw mechanisms 814 and 818, the threads of the self-piercing screw mechanisms engage with the threads on the inner radial surface of threaded inserts 815 and 819. This engagement provides the self-piercing screw bodies the necessary leverage to engage with the adjacent vertebra.

Figure 67:
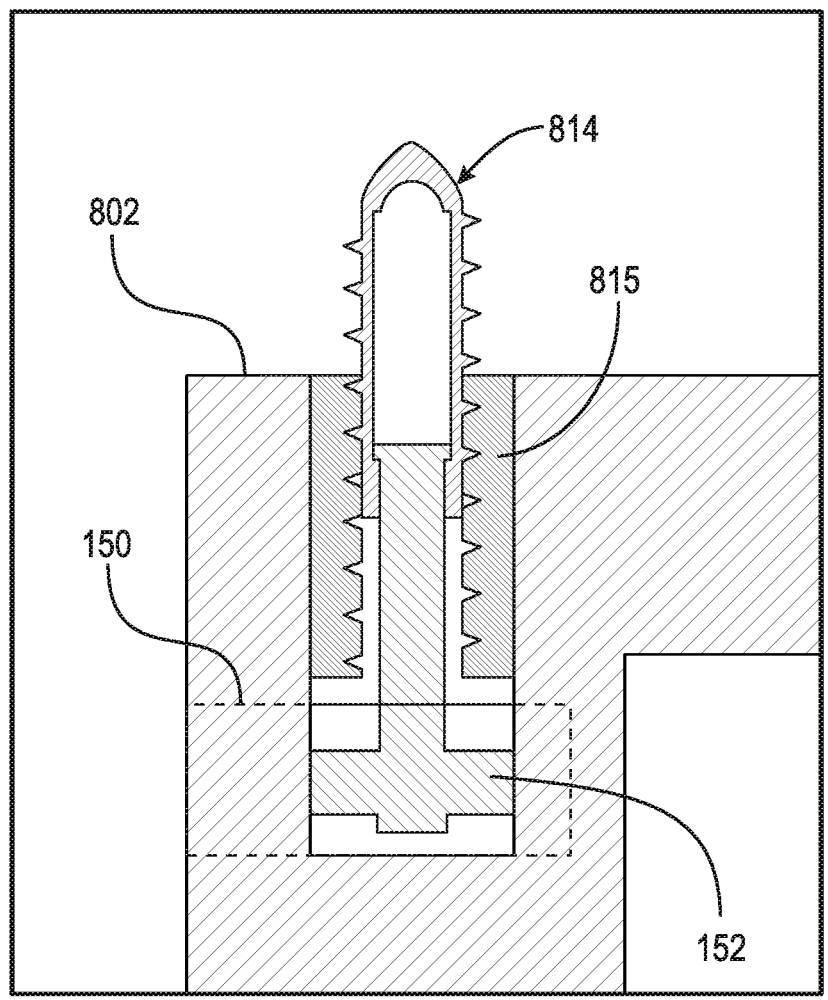
FIG. 67 is an enlarged view of area 67 in FIG. 66.

FIG. 67 is an expanded view of area 67 in FIG. 66. FIG. 67 shows self-piercing screw mechanism 814 within superior component 802, of stand-alone expandable interbody spinal fusion device 800. Threaded insert 815 is shown fixedly secured within superior component 802, and arranged to engage with the threads of self-piercing screw mechanism 814. Threaded insert 815 acts as a leverage point for self-piercing screw mechanism 814, providing the force necessary for self-piercing screw mechanism 814 to engage with adjacent vertebra.

Figure 68:
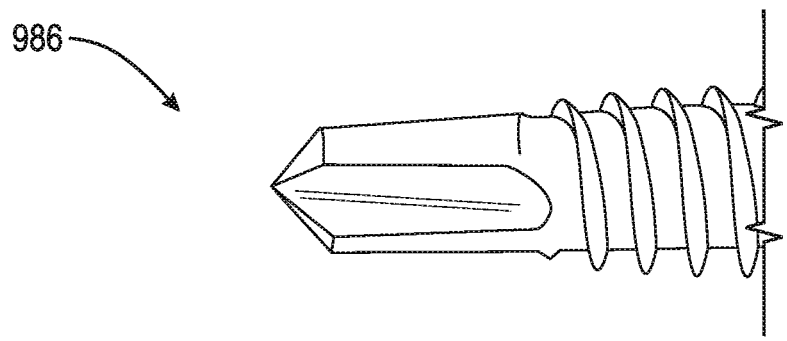
FIG. 68 is a side view of a self-drilling screw body tip.
Figure 69:
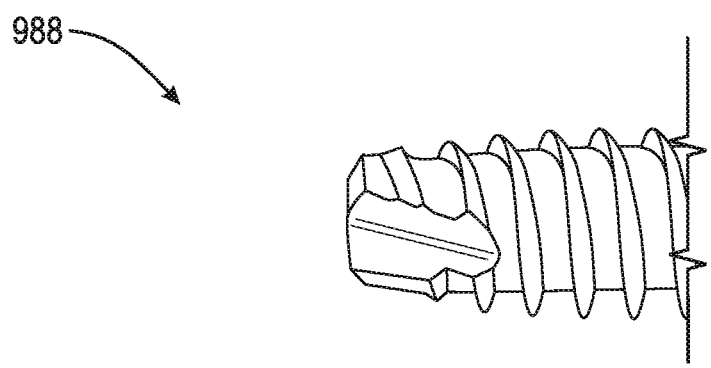
FIG. 69 is a side view of a self-tapping screw body tip.
Figure 70:
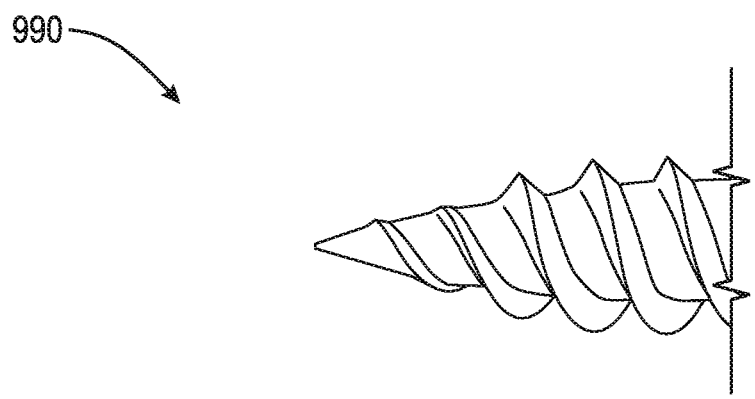
FIG. 70 is a side view of a self-piercing screw body tip.

FIG. 68 illustrates a non-limiting example of self-driving screw body tip 986 that can be used as the tip of the various screw mechanisms illustrated in this disclosure. FIG. 69 illustrates a non-limiting example of self-tapping screw body tip 988 that can be used as the tip of the various screw mechanisms illustrated in this disclosure. FIG. 70 illustrates a non-limiting example of self-piercing body tip 990 that can be used as the tip of the various screw mechanisms illustrated in this disclosure.

Figure 71A:
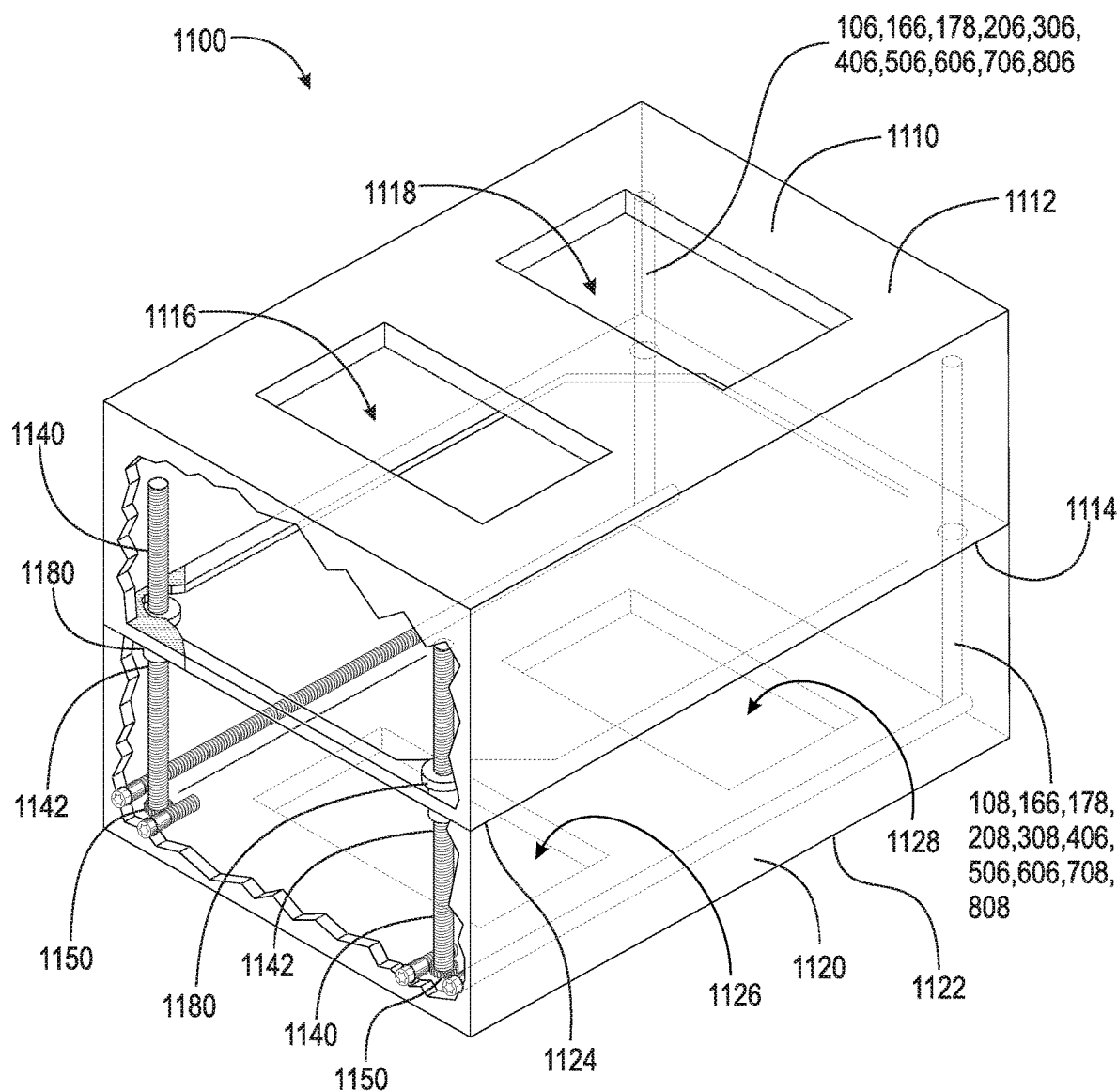
FIG. 71A is a perspective view of a stand-alone expandable interbody spinal fusion device, in an unexpanded state.

FIG. 71A is a perspective view of stand-alone expandable interbody spinal fusion device 1100, in an unexpanded state.

Figure 71B:
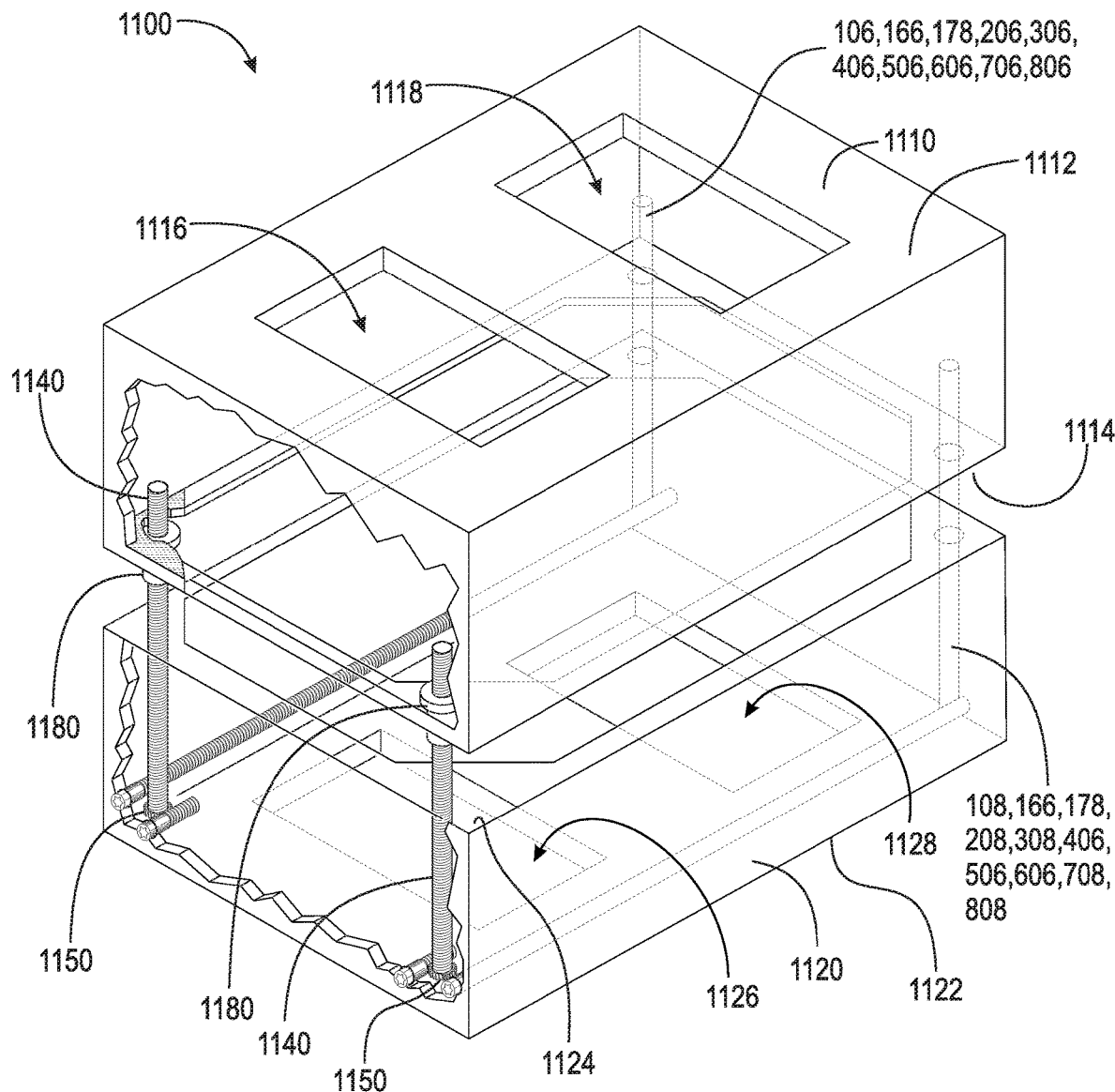
FIG. 71B is a perspective view of the stand-alone expandable interbody spinal fusion device shown in FIG. 71A, in an expanded state.

FIG. 71B is a perspective view of stand-alone expandable interbody spinal fusion device 1100, in an expanded state. Stand-alone expandable interbody spinal fusion device 1100 comprises superior component 1110, inferior component 1120, and at least one expansion mechanism, for example, expansion mechanism 1140, 106, 108, 166, 178, 206, 208, 306, 308, 406, 506, 606, 706, 708, 806, 808. It should be appreciated that any of the expansion mechanisms disclosed in FIGS. 1-72B may be used as the expansion mechanism of stand-alone expandable interbody spinal fusion device 1100. Additionally, although not shown in FIGS. 71A-B, stand-alone expandable interbody spinal fusion device 1100 may further comprise one or more screw mechanism. For example, any of the screw mechanisms disclosed in FIGS. 1-72B may be used in stand-alone expandable interbody spinal fusion device 1100 to fixedly secure superior component 1110 and/or inferior component 1120 to an adjacent vertebra.

Superior component 1110 comprises outermost surface 1112 operatively arranged to engage a vertebra and innermost surface 1114. Superior component 1110 further comprises at least one aperture, for example apertures 1116 and 1118, which extends from innermost surface 1114 to outermost surface 1112. In some embodiments, superior component 1110 further comprises holes extending from surface 1114 in which expansion mechanisms 1140 engage. In some embodiments, superior component 1110 further comprises holes that engage threaded rods 1142, such holes having a counterbore that at least partially engages collar 1180 (i.e., collar 1180 is at least partially embedded in superior component 1110). In some embodiments, and as previously described, superior component 1110 comprises at least one screw mechanism that is operatively arranged to protrude out through outer surface 1112 and engage an adjacent vertebra to fixedly secure stand-alone expandable interbody spinal fusion device 1100 to that vertebra.

Inferior component 1120 comprises outermost surface 1122 operatively arranged to engage a vertebra and innermost surface 1124. Inferior component 1120 further comprises at least one aperture, for example apertures 1126 and 1128, which extends from innermost surface 1124 to outermost surface 1122. In some embodiments, inferior component 1120 further comprises holes extending from surface 1124 in which expansion mechanisms 1140 engage. In some embodiments, and as previously described, inferior component 1120 comprises at least one screw mechanism that is operatively arranged to protrude out through outer surface 1122 and engage an adjacent vertebra to fixedly secure stand-alone expandable interbody spinal fusion device 1100 to that vertebra.

In some embodiments, and as shown, stand-alone expandable interbody spinal fusion device 1100 comprises four expansion mechanisms 1140 arranged approximately at four corners of the implant. Each expansion mechanism 1140 comprises its own worm 1160. Such embodiments enable the doctor to selectively expand stand-alone expandable interbody spinal fusion device 1100. For example, stand-alone expandable interbody spinal fusion device 1100 may be expanded such that surface 1112 is non-parallel (or parallel) to surface 1122. In some embodiments, one worm 1160 may engage two or more expansion mechanisms 1140, for example, as shown in FIGS. 41-44.

Figures 72A, 72B:
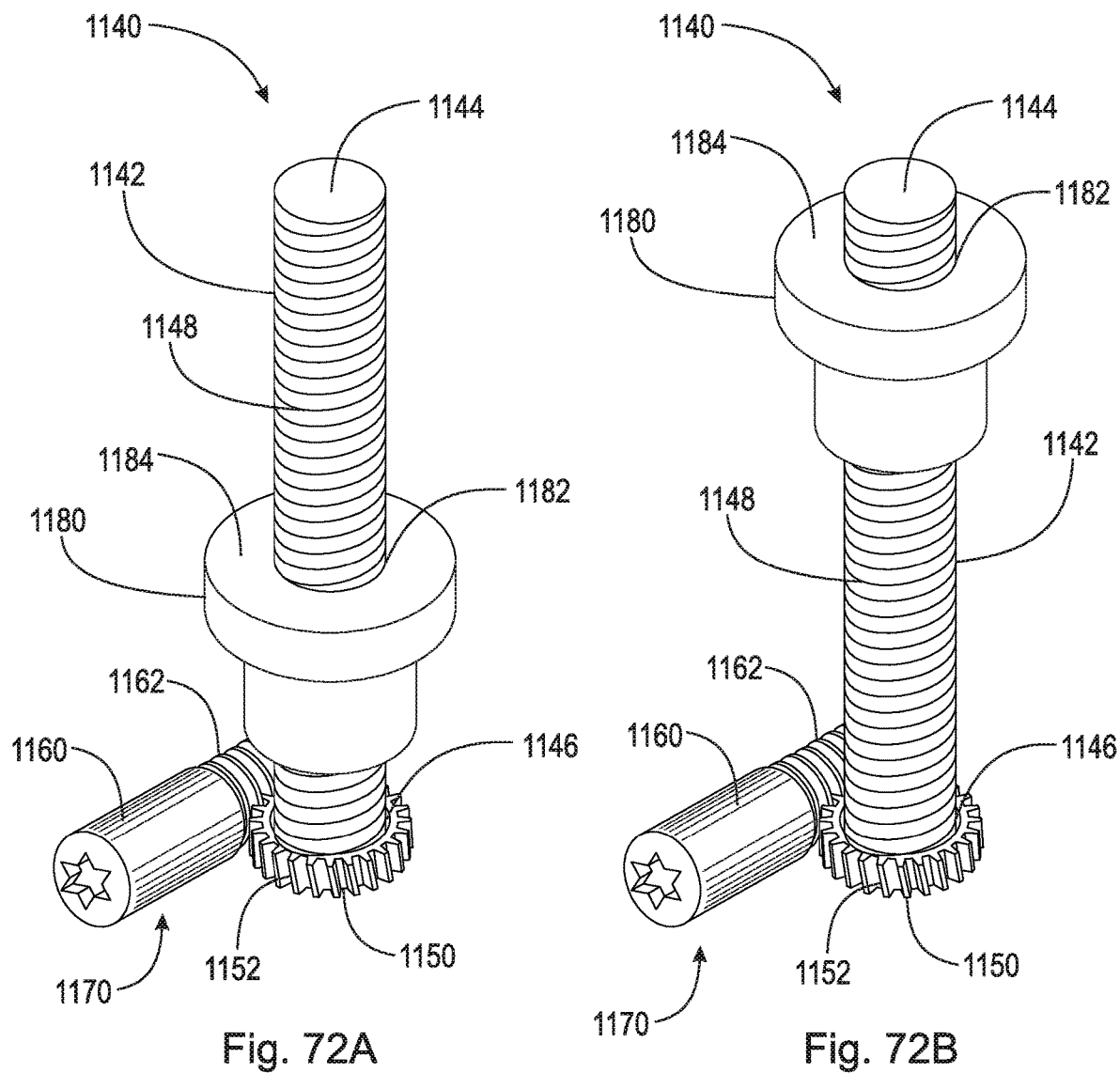
FIG. 72A is a perspective view of the expansion mechanism in FIG. 71A.
FIG. 72B is a perspective view of the expansion mechanism in FIG. 71B.

FIG. 72A is a perspective view of expansion mechanism 1140 in an unexpanded state (i.e., stand-alone expandable interbody spinal fusion device 1100 is unexpanded as shown in FIG. 71A). FIG. 72B is a perspective view of expansion mechanism 1140 in an expanded state (i.e., stand-alone expandable interbody spinal fusion device 1100 is unexpanded as shown in FIG. 71B). Expansion mechanism 1140 comprises threaded rod 1142, gear 1150, collar 1180, and worm 1160. Threaded rod 1142 comprises first end 1144, second end 1146, and threading 1148. First end 1144 is arranged to engage superior component 1110. Second end 1146 is fixedly secured to gear 1150. Gear 1152 is arranged generally perpendicular to threaded rod 1142 and comprises teeth 1152. Gear 1152 is rotatably connected to inferior component 1120. Worm 1160 comprises threading 1162 that engages teeth 1152 such that, as worm 1160 is rotated in a first circumferential direction, gear 1150 rotates in a second circumferential direction. It should be appreciated that worm 1160 and gear 1150 together form worm drive 1170. Worm 1160 is rotatably connected to inferior component 1120 and may be at least partially embedded therein. Collar 1180 is threadably engaged with threaded rod 1142. Collar 1180 comprises threaded hole 1182 and surface 1184 engaged with superior component 1110. In some embodiments, surface 1184 is engaged with surface 1114. In some embodiments, collar 1180 is at least partially embedded in superior component 1110. As gear 1150 and threaded rod 1142 rotate, collar 1180 (being non-rotatably engaged with superior component 1110) is displaced axially up and down along threaded rod 1142 thereby expanding and contracting stand-alone expandable interbody spinal fusion device 1100. Thus, by use of a tool (e.g., screw driver), a doctor can expand and contract stand-alone expandable interbody spinal fusion device 1100 by turning worm 1160. Additionally, the use of multiple expansion mechanisms arranged at various locations within stand-alone expandable interbody spinal fusion device 1100 enables the doctor to expand stand-alone expandable interbody spinal fusion device 1100 at various heights (i.e., such that superior component 1110 is not necessarily parallel to inferior component 1120).

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

LIST OF REFERENCE NUMERALS

10 Spinal column
C1-C7 Cervical vertebrae
T1-T9 Thoracic vertebrae
L1-L5 Lumbar vertebrae
S Sacrum
C Coccyx
D1 Direction
$D_{L1-L2}$ Disc
$D_{L2-L3}$ Disc
$D_{L3-L4}$ Disc
$D_{L4-L5}$ Disc
F Facet
FJ Facet joint
$h_1$ Collapsed height
$h_2$ Expanded height
SP Spinous process
TP Transverse process
IF Intervertebral foramen
A Annulus
AR Axis of rotation
N Nucleus
NC Neural canal
$H_1$ Unexpanded height
$H_2$ Expanded height
RD1 Rotational direction 1
RD2 Rotational direction 2
12 Disc space
100 Stand-alone expandable interbody spinal fusion device
102 Superior component
103 Superior component surface
104 Inferior component
105 Inferior component surface
106 First expansion mechanism
107 Anchor layer
108 Second expansion mechanism
109 Anchor layer
110 Third expansion mechanism
112 First self-piercing screw mechanism
114 Second self-piercing screw mechanism
116 Third self-piercing screw mechanism
118 Fourth self-piercing screw mechanism
120 First aperture
122 Self-piercing screw—first embodiment
124 Worm drive
126 Worm
128 Gear
130 Drive casing
132 Inner radial surface
134 Keyed shaft
136 Outer radial surface
138 First end
140 Second end
142 Self-piercing screw body
144 Tab
146 Self-piercing screw—second embodiment
148 Worm Drive
150 Worm
152 Gear
154 Rod
156 Tab
157 Flange
158 Self-piercing screw body
159 Retention shoulder
160 Partial through bore
162 Inner radial surface
164 Keyed shaft
166 Expansion mechanism—first embodiment
168 Threaded Rod
170 Threaded Sleeve
172 Worm Drive
174 Worm
176 Gear
178 Expansion mechanism—second embodiment
180 Gear
182 Toothed Shaft
192 Second aperture
200 Stand-alone expandable interbody spinal fusion device
202 Superior component
203 Superior component surface
204 Inferior component
205 Inferior component surface
206 First expansion mechanism
207 Anchor layer
208 Second expansion mechanism
209 Anchor layer
210 Third expansion mechanism
211 Fourth expansion mechanism
212 First self-piercing screw mechanism 214 Second self-piercing screw mechanism
216 Third self-piercing screw mechanism
218 Fourth self-piercing screw mechanism
220 First aperture
226 Gear shaft
250 Gear shaft
292 Second Aperture
300 Stand-alone expandable interbody spinal fusion device
302 Superior component
303 Superior component surface
304 Inferior component
305 Inferior component surface
306 First expansion mechanism
307 Anchor layer
308 Second expansion mechanism
309 Anchor layer
310 Third expansion mechanism
311 Fourth expansion mechanism
312 First self-piercing screw mechanism
314 Second self-piercing screw mechanism
316 Third self-piercing screw mechanism
318 Fourth self-piercing screw mechanism
320 First aperture
326 Gear shaft
350 Gear shaft
392 Second aperture
400 Stand-alone expandable interbody spinal fusion device
402 Superior component
403 Superior component surface
404 Inferior component
405 Inferior component surface
406 First expansion mechanism
407 Anchor layer
409 Anchor layer
412 First self-piercing screw mechanism
414 Second self-piercing screw mechanism
416 Third self-piercing screw mechanism
418 Fourth self-piercing screw mechanism
420 First aperture
484 Hinge
492 Second aperture
500 Stand-alone expandable interbody spinal fusion device
502 Superior component
503 Superior component surface
504 Inferior component
505 Inferior component surface
506 First expansion mechanism
507 Anchor layer
509 Anchor layer
512 First self-piercing screw mechanism
514 Second self-piercing screw mechanism
516 Third self-piercing screw mechanism
518 Fourth self-piercing screw mechanism
520 First aperture
584 Hinge
592 Second aperture
600 Stand-alone expandable interbody spinal fusion device
602 Superior component
603 Superior component surface
604 Inferior component
605 Inferior component surface
606 First expansion mechanism
607 Anchor layer
609 Anchor layer
612 First self-piercing screw mechanism
614 Second self-piercing screw mechanism
616 Third self-piercing screw mechanism
618 Fourth self-piercing screw mechanism
620 First aperture
684 Hinge
692 Second aperture
700 Stand-alone expandable interbody spinal fusion device
702 Superior component
703 Superior component surface
704 Inferior component
705 Inferior component surface
706 First expansion mechanism
708 Second expansion mechanism
710 Third expansion mechanism
711 Fourth expansion mechanism
712 First self-piercing screw mechanism
714 Second self-piercing screw mechanism
716 Third self-piercing screw mechanism
718 Fourth self-piercing screw mechanism
726 Gear shaft
800 Stand-alone expandable interbody spinal fusion device
802 Superior component
804 Inferior component
806 First expansion mechanism
808 Second expansion mechanism
810 Third expansion mechanism
811 Fourth expansion mechanism
812 First self-piercing screw mechanism
813 First threaded insert
814 Second self-piercing screw mechanism
815 Second threaded insert
816 Third self-piercing screw mechanism
817 Third threaded insert
818 Fourth self-piercing screw mechanism
819 Fourth threaded insert
820 First aperture
826 Gear shaft
850 Gear shaft
892 Second aperture
986 Self-drilling screw body tip
988 Self-tapping screw body tip
990 Self-piercing screw body tip
1100 Stand-alone expandable interbody spinal fusion device
1110 Superior component
1112 Surface
1114 Surface
1116 Aperture
1118 Aperture
1120 Inferior component
1122 Surface
1124 Surface
1126 Aperture
1128 Aperture
1140 Expansion mechanism
1142 Threaded rod
1144 End
1146 End
1148 Threading
1150 Gear
1152 Teeth
1160 Worm
1162 Threading
1170 Worm drive
1180 Collar
1182 Threaded hole
1184 Surface

What is claimed is:
1. A stand-alone expandable interbody spinal fusion device, comprising:

a superior component;

an inferior component; and, an expansion mechanism operatively arranged to displace the superior component relative to the inferior component, the expansion mechanism including a threaded rod including a first end engaged with the superior component and a second end engaged with the inferior component;

wherein when the threaded rod is rotated in a first circumferential direction, the superior component is displaced in a first direction relative to the inferior component.

2. The stand-alone expandable interbody spinal fusion device as recited in claim 1, wherein:

the expansion mechanism further comprises a gear rotatably connected to the inferior component; and, the second end is fixedly secured to the gear.

3. The stand-alone expandable interbody spinal fusion device as recited in claim 2, wherein the superior component comprises a threaded hole and the threaded rod is threadably engaged with the threaded hole.

4. The stand-alone expandable interbody spinal fusion device as recited in claim 2, wherein the expansion mechanism further comprises a threaded collar threadably engaged with the threaded rod.

5. The stand-alone expandable interbody spinal fusion device as recited in claim 4, wherein the threaded collar abuts against the superior component.

6. The stand-alone expandable interbody spinal fusion device as recited in claim 2, wherein the expansion mechanism further comprises a worm rotatably connected to the inferior component and engaged with the gear.

7. The stand-alone expandable interbody spinal fusion device as recited in claim 1, wherein the superior component comprises at least one aperture and the inferior component comprises at least one aperture.

8. The stand-alone expandable interbody spinal fusion device as recited in claim 1, wherein when the threaded rod is rotated in a second circumferential direction, opposite the first circumferential direction, the superior component is displaced in a second direction relative to the inferior component.

9. A stand-alone expandable interbody spinal fusion device, comprising:

an inferior component including a first inward facing surface and a first outward facing surface;

a superior component including a second inward facing surface and a second outward facing surface; and, an expansion mechanism, including:

a gear rotatably connected to the inferior component; and, a threaded rod including a first end engaged with the superior component and a second end fixedly secured to the gear;

wherein when the threaded rod is rotated in a first circumferential direction, the superior component is displaced in a first direction relative to the inferior component.

10. The stand-alone expandable interbody spinal fusion device as recited in claim 9, wherein the superior component comprises a threaded hole and the threaded rod is threadably engaged with the threaded hole.

11. The stand-alone expandable interbody spinal fusion device as recited in claim 9, wherein the expansion mechanism further comprises a threaded collar threadably engaged with the threaded rod.

12. The stand-alone expandable interbody spinal fusion device as recited in claim 11, wherein the threaded collar abuts against the superior component.

13. The stand-alone expandable interbody spinal fusion device as recited in claim 11, wherein the threaded collar is at least partially embedded in the superior component.

14. The stand-alone expandable interbody spinal fusion device as recited in claim 9, wherein the expansion mechanism further comprises a worm rotatably connected to the inferior component and engaged with the gear.

15. The stand-alone expandable interbody spinal fusion device as recited in claim 9, wherein the inferior component comprises at least one aperture extending from the first inward facing surface to the first outward facing surface and the superior component comprises at least one aperture extending from the second inward facing surface to the second outward facing surface.

16. The stand-alone expandable interbody spinal fusion device as recited in claim 9, wherein when the threaded rod is rotated in a second circumferential direction, opposite the first circumferential direction, the superior component is displaced in a second direction relative to the inferior component.

17. A stand-alone expandable interbody spinal fusion device, comprising:

an inferior component including a first inward facing surface and a first outward facing surface;

a superior component including a second inward facing surface and a second outward facing surface; and, an expansion mechanism, including:

a gear rotatably connected to the inferior component; and, a threaded rod including a first end threadably engaged with the superior component and a second end fixedly secured to the gear;

wherein when the threaded rod is rotated the superior component is displaced relative to the inferior component.

18. The stand-alone expandable interbody spinal fusion device as recited in claim 17, wherein the threaded rod is threadably engaged with the superior component via a threaded collar, the threaded collar operatively arranged to abut against the second inward facing surface.

19. The stand-alone expandable interbody spinal fusion device as recited in claim 17, wherein the expansion mechanism further comprises a worm engaged with the gear.

20. The stand-alone expandable interbody spinal fusion device as recited in claim 17, wherein the superior component comprises a threaded hole extending from the second inward facing surface and the threaded rod is threadably engaged with the threaded hole.

* * * * *